US008524728B2

(12) United States Patent
Verdonck et al.

(10) Patent No.: US 8,524,728 B2
(45) Date of Patent: Sep. 3, 2013

(54) SUBSTITUTED INDOLYL ALKYL AMINO DERIVATIVES AS NOVEL INHIBITORS OF HISTONE DEACETYLASE

(75) Inventors: Marc Gustaaf Celine Verdonck, Gierle (BE); Patrick René Angibaud, Fontaine-Bellenger (FR); Bruno Roux, Saint Leger du Bourg-Denis (FR); Isabelle Noëlle Constance Pilatte, Louviers (FR); Peter Ten Holte, Beerse (BE); Janine Arts, Breda (NL); Kristof Van Emelen, Sint-Niklaas (BE)

(73) Assignee: Janssen Pharmaceutica N.V., Beerse (BE)

( * ) Notice: Subject to any disclaimer, the term of this patent is extended or adjusted under 35 U.S.C. 154(b) by 240 days.

(21) Appl. No.: 13/027,793

(22) Filed: Feb. 15, 2011

(65) Prior Publication Data

US 2011/0136841 A1 Jun. 9, 2011

Related U.S. Application Data

(63) Continuation of application No. 11/572,563, filed as application No. PCT/EP2005/053612 on Jul. 25, 2005, now Pat. No. 8,193,205.

(60) Provisional application No. 60/592,182, filed on Jul. 29, 2004.

(30) Foreign Application Priority Data

Jul. 28, 2004 (EP) ..................................... 04077172

(51) Int. Cl.
*A61K 31/506* (2006.01)
*C07D 401/14* (2006.01)

(52) U.S. Cl.
USPC .......................................... 514/275; 544/331

(58) Field of Classification Search
USPC .......................................... 544/331; 514/275
See application file for complete search history.

(56) References Cited

U.S. PATENT DOCUMENTS

| 3,331,843 | A | 7/1967 | Tomcufcik et al. |
| 3,459,731 | A | 8/1969 | Gramera et al. |
| 3,966,743 | A | 6/1976 | Berger et al. |
| 4,049,811 | A | 9/1977 | Berger et al. |
| 4,348,401 | A | 9/1982 | Friebe et al. |
| 4,455,422 | A | 6/1984 | Banno et al. |
| 5,025,012 | A | 6/1991 | Miura et al. |
| 5,147,876 | A | 9/1992 | Mizuchi et al. |
| 5,338,738 | A | 8/1994 | Matson et al. |
| 5,342,846 | A | 8/1994 | Singh et al. |
| 5,780,454 | A | 7/1998 | Adams et al. |
| 5,789,412 | A | 8/1998 | Halazy et al. |
| 5,952,349 | A | 9/1999 | Asberom et al. |
| 6,066,730 | A | 5/2000 | Adams et al. |
| 6,083,903 | A | 7/2000 | Adams et al. |
| 6,294,538 | B1 | 9/2001 | Mylari |
| 6,518,283 | B1 | 2/2003 | Langham et al. |
| 6,589,950 | B1 | 7/2003 | Collingwood et al. |
| 6,897,307 | B2 | 5/2005 | Ciszewski et al. |
| 7,205,304 | B2 | 4/2007 | Van Emelen et al. |
| 7,446,109 | B2 | 11/2008 | Van Emelen et al. |
| 7,501,417 | B2 | 3/2009 | Van Emelen et al. |
| 7,541,369 | B2 | 6/2009 | Angibaud et al. |
| 7,592,450 | B2 | 9/2009 | Van Emelen |
| 7,615,553 | B2 | 11/2009 | Van Emelen et al. |
| 7,704,998 | B2 | 4/2010 | Van Emelen et al. |
| 7,709,487 | B2 | 5/2010 | Van Emelen et al. |
| 7,767,679 | B2 | 8/2010 | Van Emelen et al. |
| 7,816,363 | B2 | 10/2010 | Angibaud et al. |
| 7,834,011 | B2 | 11/2010 | Roux et al. |
| 7,834,025 | B2 | 11/2010 | Angibaud et al. |
| 7,884,105 | B2 | 2/2011 | Van Emelen |
| 7,888,360 | B2 | 2/2011 | Angibaud et al. |
| 8,193,205 | B2 | 6/2012 | Verdonck et al. |
| 2002/0032195 | A1 | 3/2002 | Breitfelder et al. |
| 2004/0248897 | A1 | 12/2004 | Priepke et al. |
| 2005/0080258 | A1 | 4/2005 | Davis et al. |
| 2005/0096468 | A1 | 5/2005 | Van Emelen et al. |
| 2005/0107384 | A1 | 5/2005 | Angibaud et al. |
| 2005/0171347 | A1 | 8/2005 | Emelen et al. |
| 2005/0197336 | A1 | 9/2005 | Anandan et al. |
| 2005/0222414 | A1 | 10/2005 | Van Emelen et al. |
| 2007/0135424 | A1 | 6/2007 | Van Brandt et al. |
| 2008/0132459 | A1 | 6/2008 | Moradei et al. |
| 2008/0255140 | A1 | 10/2008 | Van Emelen |
| 2009/0005393 | A1 | 1/2009 | Angibaud et al. |
| 2009/0018152 | A1 | 1/2009 | Angibaud et al. |
| 2009/0018153 | A1 | 1/2009 | Angibaud et al. |

(Continued)

FOREIGN PATENT DOCUMENTS

| CA | 2 491 131 | 1/2004 |
| CA | 2 518 950 | 2/2005 |

(Continued)

OTHER PUBLICATIONS

Glaser, HDAC inhibitors: Clinical update and mechanism-based potential, Biochemical Pharmacology, 74, pp. 659-671, 2007.*

(Continued)

*Primary Examiner* — Deepak Rao

(57) ABSTRACT

This invention comprises the novel compounds of formula (I)

(I)

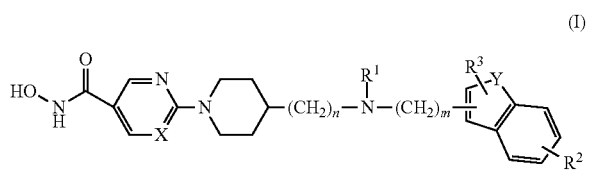

wherein $R^1$, $R^2$, $R^3$, X and Y have defined meanings, having histone deacetylase inhibiting enzymatic activity; their preparation, compositions containing them and their use as a medicine.

19 Claims, No Drawings

(56) References Cited

U.S. PATENT DOCUMENTS

| | | |
|---|---|---|
| 2009/0023726 A1 | 1/2009 | Roux et al. |
| 2009/0036463 A1 | 2/2009 | Angibaud et al. |
| 2009/0042920 A1 | 2/2009 | Van Emelen et al. |
| 2009/0124646 A1 | 5/2009 | Verdonck et al. |
| 2009/0143401 A1 | 6/2009 | Marconnet-Decrane et al. |
| 2009/0170836 A1 | 7/2009 | Angibaud et al. |
| 2009/0170881 A1 | 7/2009 | Angibaud et al. |
| 2009/0221580 A1 | 9/2009 | Angibaud et al. |
| 2009/0227558 A1 | 9/2009 | Angibaud et al. |
| 2009/0270419 A1 | 10/2009 | Arts et al. |
| 2010/0009988 A1 | 1/2010 | Emelen |
| 2010/0048588 A1 | 2/2010 | Van Emelen et al. |
| 2010/0160321 A1 | 6/2010 | Ten Holte et al. |
| 2010/0222574 A1 | 9/2010 | Rombouts et al. |
| 2010/0234353 A1 | 9/2010 | Van Emelen et al. |
| 2010/0240639 A1 | 9/2010 | Van Emelen et al. |

FOREIGN PATENT DOCUMENTS

| | | |
|---|---|---|
| DE | 042 28 792 | 3/1994 |
| DE | 102 33 412 | 2/2004 |
| EP | 0 076 530 | 12/1985 |
| EP | 0 188 094 | 3/1992 |
| EP | 0 827 742 | 3/1998 |
| EP | 1 002 795 | 5/2000 |
| EP | 0 788 360 | 5/2003 |
| EP | 1 472 216 | 11/2004 |
| EP | 1 485 353 | 12/2004 |
| EP | 1 495 002 | 1/2005 |
| EP | 1 523 470 | 4/2005 |
| EP | 1 525 199 | 4/2005 |
| EP | 1 572 626 | 9/2005 |
| EP | 1 583 736 | 10/2005 |
| EP | 1 585 735 | 10/2005 |
| EP | 1 592 667 | 11/2005 |
| EP | 1 312 609 | 12/2005 |
| EP | 1 608 628 | 12/2005 |
| EP | 1 613 622 | 1/2006 |
| EP | 1 663 953 | 6/2006 |
| EP | 1 501 508 | 2/2007 |
| EP | 1 581 484 | 7/2007 |
| EP | 1 592 665 | 7/2007 |
| EP | 1 685 094 | 8/2007 |
| EP | 1 485 354 | 5/2008 |
| EP | 1 485 365 | 5/2008 |
| EP | 1 485 348 | 6/2008 |
| EP | 1 485 378 | 6/2008 |
| EP | 1 492 534 | 6/2008 |
| EP | 1 627 880 | 10/2008 |
| EP | 1 485 364 | 3/2009 |
| EP | 1 485 370 | 3/2009 |
| EP | 1 682 538 | 5/2009 |
| EP | 1 611 088 | 6/2009 |
| EP | 1 590 340 | 4/2010 |
| EP | 1 673 349 | 6/2010 |
| EP | 1 485 099 | 7/2010 |
| ES | 2 104 509 | 10/1997 |
| GB | 0 901 749 | 7/1962 |
| GB | 1 345 872 | 2/1974 |
| WO | WO 94/25437 | 11/1994 |
| WO | WO 96/13266 | 5/1996 |
| WO | WO 97/18839 | 5/1997 |
| WO | WO 97/23216 | 7/1997 |
| WO | WO 98/05335 | 2/1998 |
| WO | WO 98/55449 | 12/1998 |
| WO | WO 99/50250 | 10/1999 |
| WO | WO 00/26203 | 5/2000 |
| WO | WO 00/27825 | 5/2000 |
| WO | WO 00/35855 | 6/2000 |
| WO | WO 00/43394 | 7/2000 |
| WO | WO 00/52001 | 9/2000 |
| WO | WO 00/71516 | 11/2000 |
| WO | WO 01/09134 | 2/2001 |
| WO | WO 01/38322 | 5/2001 |
| WO | WO 01/49688 | 7/2001 |
| WO | WO 01/70675 | 9/2001 |
| WO | WO 02/00651 | 1/2002 |
| WO | WO 02/18335 | 3/2002 |
| WO | WO 02/42271 | 5/2002 |
| WO | WO 03/000653 | 1/2003 |
| WO | WO 03/011851 | 2/2003 |
| WO | WO 03/016306 | 2/2003 |
| WO | WO 03/035855 | 5/2003 |
| WO | WO 03/066579 | 8/2003 |
| WO | WO 03/076395 | 9/2003 |
| WO | WO 03/076400 | 9/2003 |
| WO | WO 03/076401 | 9/2003 |
| WO | WO 03/076421 | 9/2003 |
| WO | WO 03/076422 | 9/2003 |
| WO | WO 03/076430 | 9/2003 |
| WO | WO 03/076438 | 9/2003 |
| WO | WO 03/082288 | 10/2003 |
| WO | WO 03/087057 | 10/2003 |
| WO | WO 03/092686 | 11/2003 |
| WO | WO 2004/009536 | 1/2004 |
| WO | WO 2004/013130 | 2/2004 |
| WO | WO 2004/056748 | 7/2004 |
| WO | WO 2004/063146 | 7/2004 |
| WO | WO 2004/063169 | 7/2004 |
| WO | WO 2004/065354 | 8/2004 |
| WO | WO 2004/069803 | 8/2004 |
| WO | WO 2004/069823 | 8/2004 |
| WO | WO 2004/071400 | 8/2004 |
| WO | WO 2004/072047 | 8/2004 |
| WO | WO 2004/082638 | 9/2004 |
| WO | WO 2004/087693 | 10/2004 |
| WO | WO 2004/092115 | 10/2004 |
| WO | WO 2005/028447 | 3/2005 |
| WO | WO 2005/030704 | 4/2005 |
| WO | WO 2005/030705 | 4/2005 |
| WO | WO 2005/040101 | 5/2005 |
| WO | WO 2005/040161 | 5/2005 |
| WO | WO 2005/075469 | 8/2005 |
| WO | WO 2005/086898 | 9/2005 |
| WO | WO 2005/092899 | 10/2005 |
| WO | WO 2006/010749 | 2/2006 |
| WO | WO 2006/010750 | 2/2006 |
| WO | WO 2006/122926 | 11/2006 |
| WO | WO 2006/136553 | 12/2006 |
| WO | WO 2007/016532 | 2/2007 |
| WO | WO 2007/048767 | 5/2007 |
| WO | WO 2007/082873 | 7/2007 |
| WO | WO 2007/082874 | 7/2007 |
| WO | WO 2007/082876 | 7/2007 |
| WO | WO 2007/082878 | 7/2007 |
| WO | WO 2007/082880 | 7/2007 |
| WO | WO 2007/082882 | 7/2007 |
| WO | WO 2008/031820 | 3/2008 |

OTHER PUBLICATIONS

Simone, Oncology: Introduction, Cecil Textbook of Medicine, 20th Edition, vol. 1, pp. 1004-1010, 1996.*

Gura et al., Systems for identifying new drugs are often faulty, Science, 278:1041-1042, 1997.*

Johnson et al., Relationships between drug activity in NCI preclinical in vitro and in vivo models and early clinical trials, British Journal of Cancer, 84(10):1424-1431, 2001.*

Takai et al., PubMed Abstract (Cancer 101(12):2760-70), Dec. 2004.*

Pearce et al., Failure modes in anticancer drug discovery and development, Cancer Drug Design and Discovery Edited by Stephen Neidle, Chapter 18, pp. 424-435 (2008).*

International Search Report from PCT/EP03/02510 dated May 22, 2003, 2 pages.

International Search Report from PCT/EP03/02511 dated May 22, 2003, 2 pages.

International Search Report from PCT/EP03/02512 dated Jun. 30, 2003, 4 pages.

International Search Report from PCT/EP03/02513 dated May 22, 2003, 2 pages.

International Search Report from PCT/EP03/02514 dated Aug. 13, 2003, 4 pages.

International Search Report from PCT/EP03/02516 dated Aug. 13, 2003, 3 pages.
International Search Report from PCT/EP03/02517 dated May 22, 2003, 2 pages.
International Search Report from PCT/EP05/53611 dated Jan. 17, 2006, 4 pages.
International Search Report from PCT/EP05/53612 dated Jul. 10, 2005, 3 pages.
International Search Report from PCT/EP06/62324 dated Aug. 16, 2006, 4 pages.
International Search Report from PCT/EP06/63351 dated Aug. 11, 2006, 2 pages.
International Search Report from PCT/EP06/67656 dated Feb. 6, 2007, 4 pages.
International Search Report from PCT/EP07/50370 dated Mar. 14, 2007, 3 pages.
International Search Report from PCT/EP07/50371 dated May 8, 2007, 4 pages.
International Search Report from PCT/EP07/50374 dated Mar. 12, 2007, 4 pages.
International Search Resort from PCT/EP07/50376 dated Mar. 28, 2007, 2 pages.
International Search Report from PCT/EP07/50379 dated May 8, 2007, 3 pages.
International Search Report from PCT/EP07/50381 dated Apr. 4, 2007, 2 pages.
International Search Report from PCT/EP07/59523 dated Mar. 20, 2008, 6 pages.
*Internal Medicine*, 4th Edition, Editor-in-Chief Jay Stein, Chapters 71-72, pp. 699-715, (1994).
Acharya et al., "Rational Development of Histone Deacetylase Inhibitors as Anticancer Agents: A Review," *Molecular Pharmacology*, 2005; 68(4):917-932.
Angibaud et al., "Discovery of Pyrimidyl-5-Hydroxamic Acids as New Potent Histone Deacetylase Inhibitors," *European Journal of Medicinal Chemistry*, 2005; 40:597-606.
Archibald et al., "Benzamidopiperidines 3. Carbocyclic Derivatives Related to Indoramin," *Journal of Medicinal Chemistry*, 1974; 17(7):739-744.
Awada et al., "The pipeline of new anticancer agents for breast cancer treatment in 2003," *Oncology Hematology*, 2003: 48:45-63.
Bali et al., "A Combination of Histone Deacetylase Inhibitor LAQ 824 and the FLT-3 Kinase Inhibitor PKC412 is Highly Active Against Human AML Cells with Constitutively Active Mutant FLT-3 Tyrosine Kinase," *Blood*, 2003; 102(11):96a-97b.
Bali et al., "Inhibition of Histone Deacetylase 6 Acetylates and Disrupts the Chaperone Function of Heat Shock Protein 90," *Journal of Biological Chemistry*, 2005; 280(29):26729-26734.
Bali et al., "Mechanisms Underlying Hydroxamic Acid Analogue (HA) Histone Deacetylase (HDAC) Inhibitors (HDIs)—Induced Apoptosis: New Role of HDAC6 Inhibition, Acetylation and Inhibition of hsp90 and Depletion of Pro-Growth and ProSurvival Oncoproteins," *Proceedings of the American Association for Cancer Research Annual Meetings*, 2005; 46(#3268):769770.
Banker et al., "Prodrugs," Modern pharmaceuticals, *Marcel Dekker, Inc.*, 3rd Ed. 1996; p. 596.
Bertino et al., "Principles of Cancer," *Cecil's Textbook of Medicine*, 2000; 21$^{st}$ Edition, vol. 1:1060-1074.
Birch et al., "N-Substituted (2, 3-Dihydro-1, 4-benzodioxin-2-yl)methylamine Derivatives as D2 Antagonists/5-HT1A Partial Agonists with Potential as Atypical Antipsychotic Agents," *J. Med. Chem.*, 1999; 42:3342-3355.
Blagosklonny et al., "Histone Deacetylase Inhibits all Induce P21 but Differentially Cause Tubulin Acetylation, Mitotic Arrest, and Cytotoxicity," *Molecular Cancer Therapeutics*, 2002; 1(11):937-941.
Calabresi P. And Chabner BA, "Section IX Chemotherapy of Neoplastic Diseases—Introduction," Goodmans & Gilman's *The Pharmacological Basis of Therapeutics*, 10th ed., 2001, Hardman JG, Limbird LE, and Gilman AG, Eds, McGraw-Hill, New York 2001, 1381-1388 (1381, 1383-1385, 1388 provided).
Carter et al., *Chemotherapy of Cancer*, Wiley (2nd edition, 1981); 362-365.

Catley et al., "Novel Hydroxamic Acid-Derived HDAC Inhibitor LBH589 Potently Activates Intrinsic and Induces Tubulin Hyperacetylation in Multiple Myeloma," *Blood*, 2005; 106(11):Abstract 1578; p. 435A.
Chen et al., "A Short and General Approach to the Synthesis of Styryllactones: (+)- Goniodiol, its Acetates and β-Trifluoromethyl Derivative, (+)-7-*epi*-Goniodiol and (+)-9- Deoxygoniopypyrone," *Synlett*, 2002; 8:1265-1268.
Chou et al., "Chemotherapeutic Synergism, Potentiation and Antagonism," *Encyclopedia of Human Biology*, 1991; 2:371-379.
Chou et al., "Computerized Quantitation of Synergism and Antagonism of Taxol, Topotecan, and Cisplatin Against Human Teratocarcinoma Cell Growth: A Rational Approach to Clinical Protocol Design," *J. Natl. Cancer Inst.*, 1994; 86(20):1517-1524.
Chou et al., "Quantitative Analysis of Dose-Effect Relationships: The Combined Effects of Multiple Drugs or Enzyme Inhibitors," *Adv. Enzyme Regul.*, 1984; 22: 27-55.
Chou et al., "The Median-Effect Principle and the Combination Index for Quantitation of Synergism and Antagonism," *Synergism and Antagonism in Chemotherapy*, 1991; pp. 60-103.
Dankwardt, et al., "Solid Phase Synthesis of Aryl and Benzylpiperazines and their Applications in Combinatorial Chemistry," *Tetrahedron Letters*, 1995; 36(28):4923-4926.
Dermer et al., "Another Anniversary for the War on Cancer," *BioTechnology*, 1994; 12:320.
Dorwald, Side Reactions in organic Synthesis, 2005, Wiley: VCH, Weinheim pg. IX of Preface.
Finney, D.J., "Probit Analyses,—A Statistical Treatment of the Sigmoid Response Curve," Graded Responses, Cambridge University Press, 1962; 2nd Ed. Chapter 10.
Freshney et al., "Culture of Animal Cells, A Manual of Basic Technique," Alan R Liss, Inc. 1983 New York, p. 1-6.
George et al., "Combination of Histone Deacetylase Inhibitor LBH589 and the hsp90 Inhibitor 17-AAG is Highly Active Against Human CML-BC Cells and AML Cells with Activating Mutation of FLT-3," *Blood*, 2005; 105(4)1 768-1776.
Glaser, "HDAC Inhibitors: Clinical Update and Mechanism-Based Potential," *Biochemical Pharmacology*, 2007; 74(5):659-671.
Golub et al., "Molecular Classification of Cancer: Class Discovery and Class Prediction by Gene Expression Monitoring," *Science*, 1999; 286:531-537.
Gorrod, et al. "The Metabolism of N-Ethyl-N-Methylaniline by Rabbit Liver Microsomes: The Measurement of Metabolites by Gasliquid Chromatography", Xenobiotica, (1975), vol. 5,No. 8, pp. 453-463.
Hideshima et al., "Small-Molecule Inhibition of Proteasome and Aggresome Function Induces Synergistic Antitumor Activity in Multiple Myeloma," *PNAS*, 2005; 102(24):8567-8572.
Horton et al., "Bortezomib Interactions with Chemotherapy Agents in Acute Leukemia In Vitro," *Cancer Chemotherapy and Pharmacology*, 2006; 58(1):13-23.
Irikura et al., "Absorption, Excretion, and Metabolism of 1-(*p*-aminobenzoyl)-4-(3, 4, 5-trimethoxybenzamido)piperidine (KU-55)," *Pharmacometrics*, 1973; 7(7):985-990. (With English-language Abstract).
Kristeleit et al., "Histone Modification Enzymes: Novel Targets for Cancer Drugs," *Expert Opin. Emerg. Drugs*, 2004; 9(1):135-154.
Lentzsch et al., "Combination of Proteasome Inhibitor PS 341 with Histone Acetylase Inhibitor (HDAC) PXD 101 Shows Superior Anti-Myeloma Activity and Inhibits Osteoclastogenesis," *Blood Poster Session*, 2005; 106(Abstract 2488):p. 1.
Mai et al., Histone Deacetylation in Epigenetics: an Attractive Target for Anticancer Therapy, *Medicinal Research Reviews*, 2005; 25(3):261-309.
Mitsiades et al., Transcriptional Signature of Histone Deacetylase Inhibition in Multiple Myeloma: Biological and Clinical Implications, *PNAS*, 2004; 101(2):540-545.
Monneret, "Histone Deacetylase Inhibitors," *European Journal of Medicinal Chemistry*, 2004; 40:1-13.
Nawrocki et al., "Aggresome Disruption: A Novel Strategy to Enhance BortezomibInduced Apoptosis in Pancreatic Cancer Cells," *Cancer Research*, 2006; 66(7):3773-3781.

Pan P.C. et al., "Soluble Polymer-Supported Synthesis of Arylpiperazines," *Tetrahedron Letters*, 1998; 39:9505-9508.

Pasternak et al., "Potent, orally bioavailable somoatostatin agonists; good absorption achieved by urea backbone cyclization," *Bioorganic and Medicinal Chemistry Letters 9*, 1999; 9:491-496.

Patani et al., "Bioisosterism: A Rational Approach in Drug Design," *Chem. Rev.*, 1996; 96: 3147-3176.

Pei Xin-Yan et al., "Synergistic Induction of Oxidative Injury and Apoptosis in Human Multiple Myeloma Cells by the Proteasome Inhibitor Bortezomib and Histone Deacetylase Inhibitors," *Clinical Cancer Research*, 2004; 10:3839-3852.

Sausville et al., "Contributions of Human Tumor Xenografts to Anti-cancer Drug Development," *American Association for Cancer Research*, 2006; 66(7):3351-3354.

Simone, J.V., "Oncology: Introduction," *Cecil's Textbook of Medicine*, 1996; 20$^{th}$ Edition, vol. 1:1004-1010.

Sternson et al., "Synthesis of 7200 Small Molecules Based on a Substructural Analysis of the Histone Deacetylase Inhibitors Trichostatin and Trapoxin," *Organic Letters*, 2001; 3(26):4239-4242.

Sutheesophon et al., "Histone Deacetylase Inhibitor Despsipeptides (FK228) Induces Apoptosis in Leukemic Cells by Facilitating Mitochondrial Translocation of Bax, Which is Enhanced by the Proteasome Inhibitor Bortezomib," *ACTA Haematologica*, 2006; 115:78-90.

Takai et al., "Human Ovarian Carcinoma Cells: Histone Deacetylase Inhibitors Exhibit Antiproliferative Activity and Potently Induce Apoptosis," *American Cancer Society*, 2004; 101(12):2760-2770.

Taylor et al., CAPLUS Abstract 55:33107 (1961).

Van Emelen et al., "Discovery of a Novel Class of Aromatic Hydroxamic Acids as Potent HDAC Inhibitors," *AARC-NCI_Eortc International Conference on Molecular Targets and Cancer Therapeutics*, 2003, XP009095813.

Van Emelen et al., "Synthesis, biological evaluation and structure activity relationships of a novel series of aromatic hydroxamic acids as potent HDAC inhibitors," *European Journal of Cancer Supp.*, 2004; 2(8):40-41[Poster Session 125].

Wolff, Burger's Medicinal Chemistry, 5th Ed. Part 1, pp. 975-977 (1995).

Yokoyama et al., CAPLUS Abstract 105:208919 (1986).

Yokoyama et al., CAPLUS Abstract 105:226622 (1986).

Yu et al., "The Proteasome Inhibitor Bortezomib Interacts Synergistically with Histone Deacetylase Inhibitors to Induce Apoptosis in Bcr/Abl$^+$Cells Sensitive and Resistant to STI571," *Blood*, 2003; 102:3765-3774.

Arts, J., et al., "JNJ-26481585, a Novel "Second-Generation" Oral Histone Deacetylase Inhibitor, Shows Broad-Spectrum Preclinical Antitumoral Activity," *Clin Cancer Res.*, 2009; 15:6841-6851.

Deleu et al., "The effects of JNJ-26481585, a novel hydroxamate-based histone deacetylase inhibitor, on the development of multiple myeloma in the 5T2MM and 5T33MM murine models," *Leukemia*; 2009; 23:1894-1903.

Minamiya et al., "Expression of histone deacetylase 1 correlates with a poor prognosis in patients with adenocarcinoma of the lung," *Lung Cancer*, 2011; 74:300-304.

Nakagawa et al., "Expression profile of class I histone deacetylases in human cancer tissues," *Oncology Reports*; 2007; 18:769-774.

Osada et al., "Reduced Expression of Class II Histone Deacetylase Genes is Associated With Poor Prognosis in Lung Cancer Patients," *Int. J. Cancer*, 2004; 112:26-32.

Sasaki et al., "Histone deacetylase 1 mRNA expression in lung cancer," *Lung Cancer*, 2004; 46:171-178.

Stuhmer et al., "Preclinical anti-myeloma activity of the novel HDAC-inhibitor JNJ26481585," *British Journal of Haematology*; 2010; 149:529-536.

Tong et al., "Preclinical antileukemia activity of JNJ-26481585, a potent second-generation histone deacetylase inhibitor," *Leukemia Research*; 2010; 34:221-228.

\* cited by examiner

```
                        SEQUENCE LISTING

<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 1
gagggcgcgg tgcttgg                                              17

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 2
tgccgccgct ctctcacc                                             18

<210> SEQ ID NO 3
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 3
tcgggtaccg agggcgcggt gcttgg                                    26

<210> SEQ ID NO 4
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 4
atactcgagt gccgccgctc tctcacc                                   27

<210> SEQ ID NO 5
<211> LENGTH: 35
<212> TYPE: DNA
<213> ORGANISM: Artificial Sequence
<220> FEATURE:
<223> OTHER INFORMATION: Oligonucleotide Primer

<400> SEQUENCE: 5
tcgggtaccg gtagatggga gcggatagac acatc                          35

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 6
atactcgagt gccgccgctc tctcacc                                   27
```

SUBSTITUTED INDOLYL ALKYL AMINO DERIVATIVES AS NOVEL INHIBITORS OF HISTONE DEACETYLASE

CROSS REFERENCE TO RELATED APPLICATIONS

This application is a Continuation application of pending U.S. application Ser. No. 11/572,563 filed Jan. 23, 2007, which is a U.S. National Stage Filing under 371 of PCT/EP2005/053612 filed Jul. 25, 2005 and U.S. Patent Application No. 60/592,182 filed Jul. 29, 2004, the entire disclosures of which are hereby incorporated in their entirety.

This invention concerns compounds having histone deacetylase (HDAC) inhibiting enzymatic activity. It further relates to processes for their preparation, to compositions comprising them, as well as their use, both in vitro and in vivo, to inhibit HDAC and as a medicine, for instance as a medicine to inhibit proliferative conditions, such as cancer and psoriasis.

Nuclear histones are known as integral and dynamic components of the machinery responsible for regulating gene transcription and other DNA-templated processes such as replication, repair, recombination, and chromosome segregation. They are the subject of post-translational modifications including acetylation, phosphorylation, methylation, ubiquitination, and ADP-ribosylation.

Histone deacetylase(s), herein referred to as "HDACs", are enzymes that catalyze the removal of the acetyl modification on lysine residues of proteins, including the core nucleosomal histones H2A, H2B, H3 and H4. Together with histone acetyl-transferase(s), herein referred to as "HATs", HDACs regulate the level of acetylation of the histones. The balance of acetylation of nucleosomal histones plays an important role in transcription of many genes. Hypoacetylation of histones is associated with condensed chromatin structure resulting in the repression of gene transcription, whereas acetylated histones are associated with a more open chromatin structure and activation of transcription.

Eleven structurally related HDACs have been described and fall into two classes. Class I HDACs consist of HDAC 1, 2, 3, 8 and 11 whereas class II HDACs consist of HDAC 4, 5, 6, 7, 9 and 10. Members of a third class of HDACs are structurally unrelated to the class I and class II HDACs. Class I/II HDACs operate by zinc-dependent mechanisms, whereas class III HDACs are NAD-dependent.

In addition to histones, other proteins have also been the substrate for acetylation, in particular transcriptionfactors such as p53, GATA-1 and E2F; nuclear receptors such as the glucocorticoid receptor, the thyroid receptors, the estrogen receptors; and cell-cycle regulating proteins such as pRb. Acetylation of proteins has been linked with protein stabilization, such as p53 stabilization, recruitment of cofactors and increased DNA binding. p53 is a tumour suppressor that can induce cell cycle arrest or apoptosis in response to a variety of stress signals, such as DNA damage. The main target for p53-induced cell cycle arrest seems to be the p21 gene. Next to its activation by p53, p21 has been identified by virtue of its association with cyclin/cyclin-dependent kinase complexes resulting in cell cycle arrest at both G1 and G2 phases, its up-regulation during senescence, and its interaction with the proliferating cell nuclear antigen.

The study of inhibitors of HDACs indicates that they play an important role in cell cycle arrest, cellular differentiation, apoptosis and reversal of transformed phenotypes.

The inhibitor Trichostatin A (TSA), for example, causes cell cycle arrest at both G1 and G2 phases, reverts the transformed phenotype of different cell lines, and induces differentiation of Friend leukemia cells and others. TSA (and suberoylanilide hydroxamic acid SAHA) have been reported to inhibit cell growth, induce terminal differentiation, and prevent the formation of tumours in mice (Finnin et al., Nature, 401: 188-193, 1999).

Trichostatin A has also been reported to be useful in the treatment of fibrosis, e.g. liver fibrosis and liver chirrhosis. (Geerts et al., European Patent Application EP 0 827 742, published 11 Mar., 1998).

The pharmacophore for HDAC inhibitors consists of a metal-binding domain, which interacts with the zinc-containing active site of HDACs, a linker domain, and a surface recognition domain or capping region, which interacts with residues on the rim of the active site.

Inhibitors of HDACs have also been reported to induce p21 gene expression. The transcriptional activation of the p21 gene by these inhibitors is promoted by chromatin remodelling, following acetylation of histones H3 and H4 in the p21 promotor region. This activation of p21 occurs in a p53-independent fashion and thus HDAC inhibitors are operative in cells with mutated p53 genes, a hallmark of numerous tumours.

In addition HDAC inhibitors can have indirect activities such as augmentation of the host immune respons and inhibition of tumor angiogenesis and thus can suppress the growth of primary tumors and impede metastasis (Mai et al., Medicinal Research Reviews, 25: 261-309).

In view of the above, HDAC inhibitors can have great potential in the treatment of cell proliferative diseases or conditions, including tumours with mutated p53 genes.

Patent application EP1472216 published on Aug. 14, 2003 discloses bicyclic hydroxamates as inhibitors of histone deacetylase.

Patent applications EP1485099, EP1485348, EP1485353, EP1485354, EP1485364, EP1485365, EP1485370, EP1485378 published on 18 Sep., 2003, amongst others, disclose substituted piperazinylpyrimidinylhydroxamic acids as inhibitors of histone deacetylase furthermore EP1485365 discloses R306465.

Patent application EP1492534 published on 9 Oct., 2003, discloses carbamic acid compounds comprising a piperazine linkage, as HDAC inhibitors.

Patent application EP1495002 published on 23 Oct., 2003, disclose substituted piperazinyl phenyl benzamide compounds, as histone deacetylase inhibitors.

Patent application WO04/009536 published on 29 Jan., 2004, discloses derivatives containing an alkyl linker between the aryl group and the hydroxamate, as histone deacetylase inhibitors.

Patent application EP1525199 published on 12 Feb., 2004, discloses (hetero)arylalkenyl substituted bicyclic hydroxamates, as histone deacetylase inhibitors.

Patent application WO04/063146 published on 29 Jul. 2004, discloses derivatives of N-hydroxy-benzamide derivatives with anti-inflammatory and antitumour activity.

Patent application WO04/063169 published on 29 Jul. 2004, discloses substituted aryl hydroxamate derivatives as histone deacetylase inhibitors.

Patent application WO04/072047 published on 26 Aug. 2004, discloses indoles, benzimidazoles and naphhimidazoles as histone deacetylase inhibitors.

Patent application WO04/082638 published on 30 Sep. 2004, discloses hydroxamates linked to non-aromatic heterocyclic ring systems as histone deacetylase inhibitors.

Patent application WO04/092115 published on 28 Oct. 2004, discloses hydroxamate derivatives as histone deacetylase inhibitors.

Patent application WO05/028447 published on 31 Mar. 2005, discloses benzimidazoles as histone deacetylase inhibitors.

Patent applications WO05/030704 and WO05/030705 published on 7 Apr. 2005, discloses benzamides as histone deacetylase inhibitors.

Patent application WO05/040101 published on 6 May 2005, disloses acylurea connected and sulfonylurea connected hydroxamates as histone deacetylase inhibitors.

Patent application WO05/040161 also published on 6 May 2005, discloses biaryl linked hydroxamates as histone deacetylase inhibitors.

The compounds of the present invention differ from the prior art in structure, in their pharmacological activity and/or pharmacological potency.

The problem to be solved is to provide histone deacetylase inhibitors with high enzymatic and cellular activity that have increased bioavailability and/or in vivo potency.

The novel compounds of the present invention solve the above-described problem. The compounds of the present invention show excellent histone deacetylase inhibiting enzymatic and cellular activity. They have a high capacity to activiate the p21 gene, both at the cellular and the in vivo level. They have a desirable pharmacokinetic profile and low affinity for the P450 enzymes, which reduces the risk of adverse drug-drug interaction allowing also for a wider safety margin.

Advantageous features of the present compounds are metabolic stability, solubility and/or p21 induction capacity. More in particular the compounds of the present invention have increased half-lives in rat hepatocytes, have an increased solubility/stability in aqueous solutions and/or have enhanced in vivo p21 promoter inducing capacities.

This invention concerns compounds of formula (I)

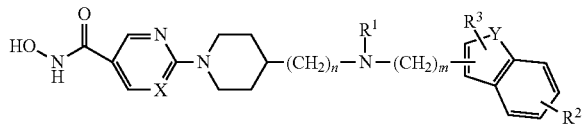

(I)

the N-oxide forms, the pharmaceutically acceptable addition salts and the stereo-chemically isomeric forms thereof, wherein each n is an integer with value 0, 1 or 2 and when n is 0 then a direct bond is intended;

each m is an integer with value 1 or 2;

each X is independently N or CH;

each Y is independently O, S, or $NR^4$; wherein each $R^4$ is hydrogen, $C_{1-6}$alkyl, $C_{1-6}$alkyloxy$C_{1-6}$alkyl, $C_{3-6}$cycloalkyl, $C_{3-6}$cycloalkylmethyl, phenyl$C_{1-6}$alkyl, —C(=O)—CHR$^5$R$^6$ or —S(=O)$_2$—N(CH$_3$)$_2$; wherein each $R^5$ and $R^6$ is independently hydrogen, amino, $C_{1-6}$alkyl or amino$C_{1-6}$alkyl; and when Y is NR$^4$ and R$^2$ is on the 7-position of the indolyl then R$^2$ and R$^4$ together can form the bivalent radical —(CH$_2$)$_2$— (a-1), or —(CH$_2$)$_3$— (a-2);

R$^1$ is hydrogen, $C_{1-6}$alkyl, hydroxy$C_{1-6}$alkyl, $C_{1-6}$alkylsulfonyl, $C_{1-6}$alkylcarbonyl or mono- or di($C_{1-6}$alkyl)aminosulfonyl;

R$^2$ is hydrogen, hydroxy, amino, halo, $C_{1-6}$alkyl, cyano, $C_{2-6}$alkenyl, polyhalo$C_{1-6}$alkyl, nitro, phenyl, $C_{1-6}$alkylcarbonyl, hydroxycarbonyl, $C_{1-6}$alkylcarbonylamino, $C_{1-6}$alkyloxy, or mono- or di($C_{1-6}$alkyl)amino;

R$^3$ is hydrogen, $C_{1-6}$alkyl, or $C_{1-6}$alkyloxy; and when R$^2$ and R$^3$ are on adjacent carbon atoms, they can form the bivalent radical

—O—CH$_2$—O—.

Lines drawn into the bicyclic ring systems from substituents indicate that the bonds may be attached to any of the suitable ring atoms of the bicyclic ring system.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone. Preferably, such inhibition is specific, i.e. the histone deacetylase inhibitor reduces the ability of a histone deacetylase to remove an acetyl group from a histone at a concentration that is lower than the concentration of the inhibitor that is required to produce some other, unrelated biological effect.

As used in the foregoing definitions and hereinafter, halo is generic to fluoro, chloro, bromo and iodo; $C_{1-2}$alkyl straight chain saturated hydrocarbon radicals having 1 or 2 carbon atoms such as, e.g. methyl or ethyl; $C_{1-6}$alkyl defines $C_{1-2}$alkyl and straight and branched chain saturated hydrocarbon radicals having from 3 to 6 carbon atoms such as, e.g. propyl, butyl, 1-methylethyl, 2-methylpropyl, pentyl, 2-methyl-butyl, hexyl, 2-methylpentyl and the like; and polyhalo$C_{1-6}$alkyl defines $C_{1-6}$alkyl containing three identical or different halo substituents for example trifluoromethyl; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; $C_{3-6}$cycloalkyl includes cyclic hydrocarbon groups having from 3 to 6 carbons, such as cyclopropyl, cyclobutyl, cyclopentyl, cyclopentenyl, cyclohexyl, cyclohexenyl, and the like.

Pharmaceutically acceptable addition salts encompass pharmaceutically acceptable acid addition salts and pharmaceutically acceptable base addition salts. The pharmaceutically acceptable acid addition salts as mentioned hereinabove are meant to comprise the therapeutically active non-toxic acid addition salt forms, which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, trifluoroacetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "acid or base addition salts" also comprises the hydrates and the solvent addition forms, which the compounds of formula (I) are able to form. Examples of such forms are e.g. hydrates, alcoholates and the like.

The term "stereochemically isomeric forms of compounds of formula (I)", as used herein, defines all possible compounds made up of the same atoms bonded by the same sequence of bonds but having different three-dimensional structures, which are not interchangeable, which the compounds of formula (I) may possess. Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine-, piperazine or pyridazinyl-nitrogens are N-oxidized.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable addition salts and all stereoisomeric forms.

As used herein, the terms "histone deacetylase" and "HDAC" are intended to refer to any one of a family of enzymes that remove acetyl groups from the ε-amino groups of lysine residues at the N-terminus of a histone. Unless otherwise indicated by context, the term "histone" is meant to refer to any histone protein, including H1, H2A, H2B, H3, H4, and H5, from any species. Human HDAC proteins or gene products, include, but are not limited to, HDAC-1, HDAC-2, HDAC-3, HDAC-4, HDAC-5, HDAC-6, HDAC-7, HDAC-8, HDAC-9 HDAC-10 and HDAC-11. The histone deacetylase can also be derived from a protozoal or fungal source.

A first group of interesting compounds consists of those compounds of formula (I) wherein one or more of the following restrictions apply:
a) each $R^4$ is hydrogen, $C_{1-6}$alkyl, $C_{3-6}$cycloalkyl, $C_{3-6}$cycloalkylmethyl, —C(=O)—CHR$^5$R$^6$ or —S(=O)$_2$—N(CH$_3$)$_2$;
b) $R^1$ is hydrogen, $C_{1-6}$alkyl, hydroxy$C_{1-6}$alkyl, $C_{1-6}$alkylsulfonyl, or mono- or di($C_{1-6}$alkyl)aminosulfonyl; or
c) $R^3$ is hydrogen.

A second group of interesting compounds consists of those compounds of formula (I) wherein one or more of the following restrictions apply:
a) each n is an integer with value 0 or 1;
b) each X is independently N;
c) each $R^4$ is hydrogen or $C_{1-6}$alkyl;
d) $R^1$ is hydrogen, $C_{1-6}$alkyl or hydroxy$C_{1-6}$alkyl; or
e) $R^2$ is hydrogen, halo, $C_{1-6}$alkyl or $C_{1-6}$alkyloxy.

A third group of interesting compounds consists of those compounds of formula (I) wherein one or more of the following restrictions apply:
a) each n is an integer with value 0 or 1;
b) each $R^4$ is hydrogen, $C_{1-6}$alkyl, $C_{1-6}$alkyloxy$C_{1-6}$alkyl, $C_{3-6}$cycloalkyl or phenyl$C_{1-6}$alkyl;
c) $R^1$ is hydrogen, $C_{1-6}$alkyl, hydroxy$C_{1-6}$alkyl, $C_{1-6}$alkylcarbonyl or $C_{1-6}$alkylsulfonyl; or
d) $R^2$ is hydrogen, halo, $C_{1-6}$alkyl, cyano, nitro or $C_{1-6}$alkyloxy.

A fourth group of interesting compounds consists of those compounds of formula (I) wherein one or more of the following restrictions apply:
a) each n is an integer with value 0 or 1;
b) each m is an integer with value 1;
c) each $R^4$ is hydrogen, $C_{1-6}$alkyloxy$C_{1-6}$alkyl, $C_{3-6}$cycloalkyl or phenyl$C_{1-6}$alkyl;
e) $R^1$ is hydrogen, hydroxy$C_{1-6}$alkyl, $C_{1-6}$alkylcarbonyl or $C_{1-6}$alkylsulfonyl;
d) $R^2$ is hydrogen, halo, cyano, nitro or $C_{1-6}$alkyloxy; or
e) $R^3$ is $C_{1-6}$alkyloxy; or
f) when $R^2$ and $R^3$ are on adjacent carbon atoms, they can form the bivalent radical
—O—CH$_2$—O—.

A fifth group of interesting compounds consists of those compounds of formula (I) wherein one or more of the following restrictions apply:

a) each n is an integer with value 1;
b) each m is an integer with value 1;
c) each X is independently N;
d) each Y is independently NR$^4$;
e) each $R^4$ is $C_{1-6}$alkyl;
f) $R^1$ is hydrogen;
g) $R^2$ is hydrogen or halo; or
h) $R^3$ is hydrogen.

A group of preferred compounds consists of those compounds of formula (I) wherein each n is an integer with value 0 or 1; each $R^4$ is hydrogen, $C_{1-6}$alkyl, $C_{1-6}$alkyloxy$C_{1-6}$alkyl, $C_{3-6}$cycloalkyl or phenyl$C_{1-6}$alkyl; $R^1$ is hydrogen, $C_{1-6}$alkyl, hydroxy$C_{1-6}$alkyl, $C_{1-6}$alkylcarbonyl or $C_{1-6}$alkylsulfonyl; and $R^2$ is hydrogen, halo, $C_{1-6}$alkyl, cyano, nitro, polyhalo$C_{1-6}$alkyl or $C_{1-6}$alkyloxy.

A group of more preferred compounds consists of those compounds of formula (I) wherein each n is an integer with value 1; each m is an integer with value 1; each X is independently N; each Y is independently NR$^4$; each $R^4$ is $C_{1-6}$alkyl; $R^1$ is hydrogen; $R^2$ is hydrogen or halo; and $R^3$ is hydrogen.

The most preferred compounds are compound No. 1a, compound No. 30, compound No. 39 and compound No. 50

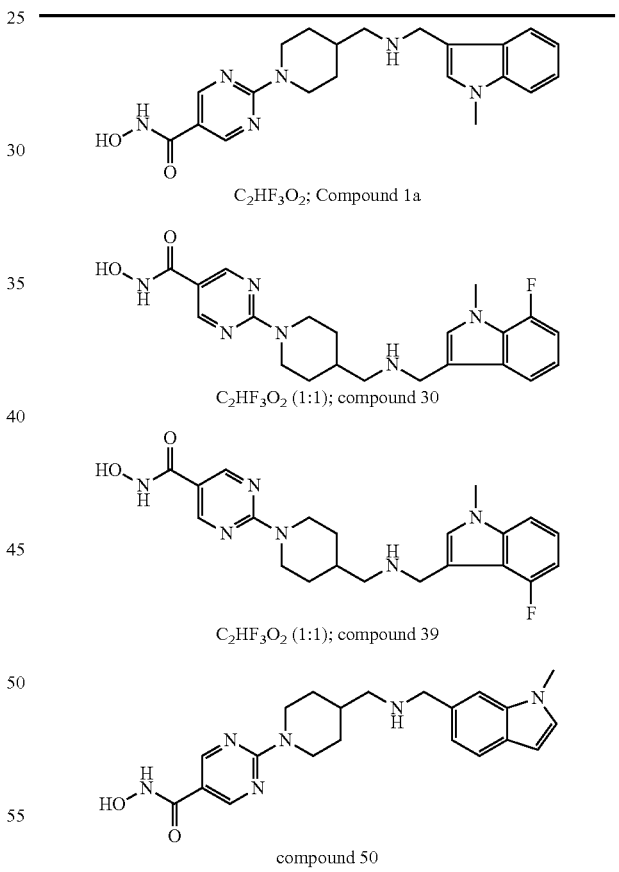

The compounds of formula (I) and (II), their pharmaceutically acceptable salts and N-oxides and stereochemically isomeric forms thereof may be prepared in conventional manner. The starting materials and some of the intermediates are known compounds and are commercially available or may be prepared according to conventional reaction procedures as generally known in the art or as described in patent applications EP1485099, EP1485348, EP1485353, EP1485354, EP1485364, EP1485365, EP1485370, and EP1485378.

Some preparation methods will be described hereinafter in more detail. Other methods for obtaining final compounds of formula (I) are described in the examples.

a) Hydroxamic acids of formula (I) may be prepared by reacting an intermediate of formula (II), wherein Q is tetrahydropyranyloxyaminocarbonyl, herein referred to as intermediates of formula (II-a), with an appropriate acid, such as for example, trifluoro acetic acid. Said reaction is performed in an appropriate solvent, such as, for example, methanol or dichloromethane.

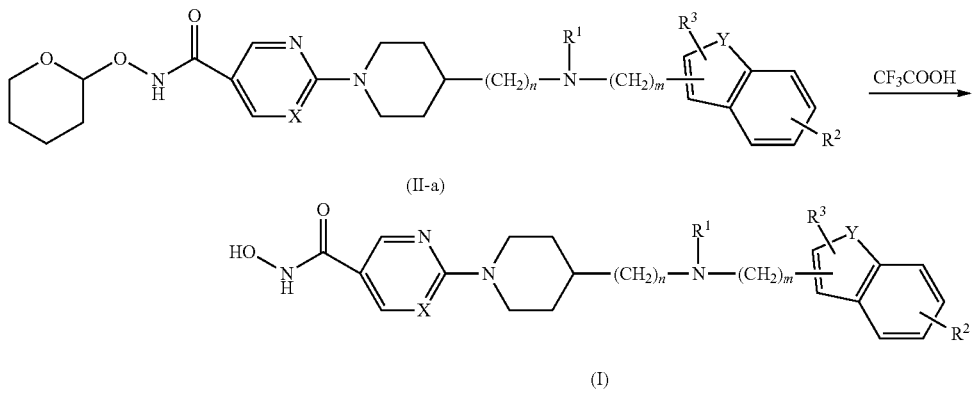

b) Alternatively, hydroxamic acids of formula (I) may be prepared by reacting an intermediate of formula (II), wherein Q is $C_{1-2}$alkyloxycarbonyl, herein referred to as intermediates of formula (II-c), with hydroxylamine, in the presence of a base such as for example sodium hydroxyde. Said reaction is performed in an appropriate solvent, such as, for example, methanol.

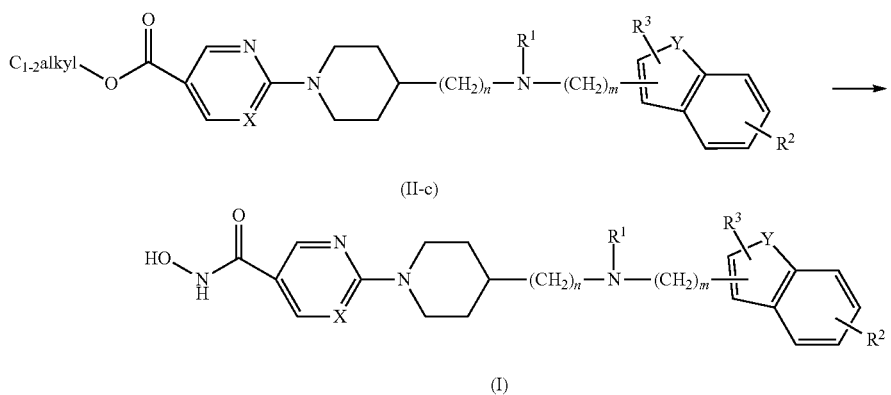

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

The present invention also concerns intermediates of formula (II)

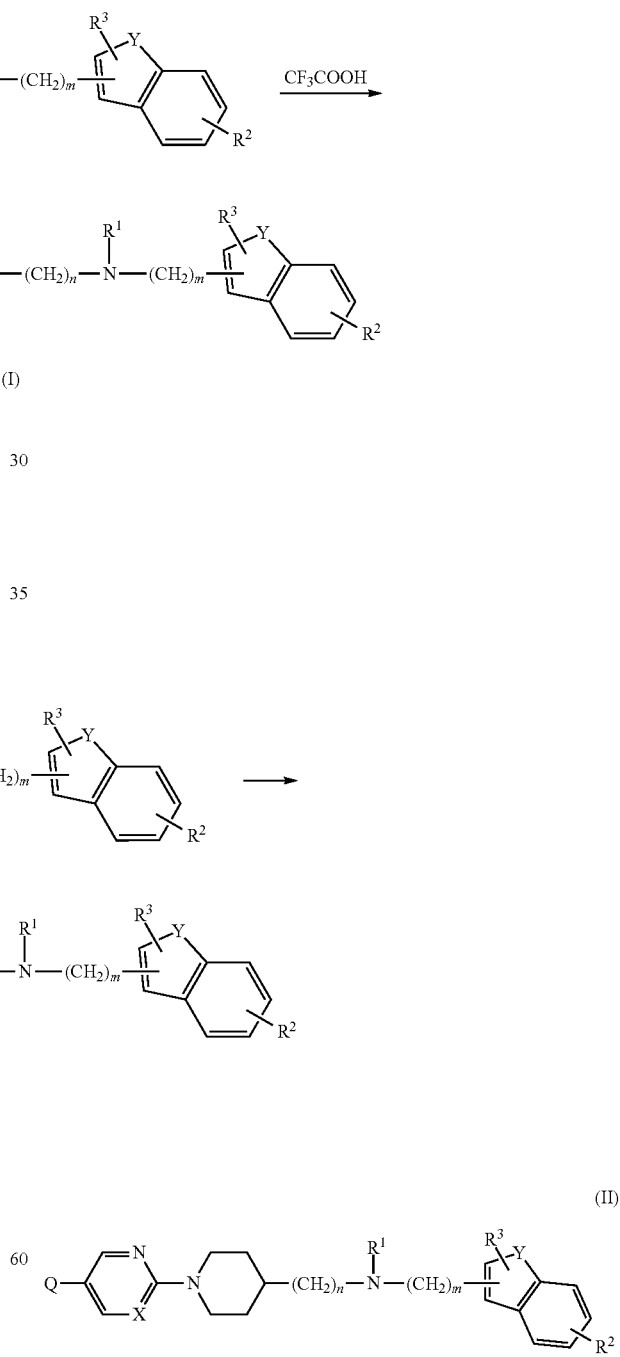

the N-oxide forms, the pharmaceutically acceptable addition salts and the stereo-chemically isomeric forms thereof, wherein each n is an integer with value 0, 1 or 2 and when n is 0 then a direct bond is intended;
each m is an integer with value 1 or 2;
each X is independently N or CH;
each Y is independently O, S, or $NR^4$; wherein
each $R^4$ is hydrogen, $C_{1-6}$alkyl, $C_{1-6}$alkyloxy$C_{1-6}$alkyl, $C_{3-6}$cycloalkyl, $C_{3-6}$cycloalkylmethyl, phenyl$C_{1-6}$alkyl, —C(=O)—$CHR^5R^6$ or —S(=O)$_2$—N(CH$_3$)$_2$; wherein
each $R^5$ and $R^6$ is independently hydrogen, amino, $C_{1-6}$alkyl or amino$C_{1-6}$alkyl; and
when Y is $NR^4$ and $R^2$ is on the 7-position of the indolyl then $R^2$ and $R^4$ together can form the bivalent radical —(CH$_2$)$_2$— (a-1), or —(CH$_2$)$_3$— (a-2);

$R^1$ is hydrogen, $C_{1-6}$alkyl, hydroxy$C_{1-6}$alkyl, $C_{1-6}$alkylsulfonyl, $C_{1-6}$alkylcarbonyl or mono- or di($C_{1-6}$alkyl)aminosulfonyl;

when $R^2$ and $R^3$ are on adjacent carbon atoms, they can form the bivalent radical —O—CH$_2$—O—; and Q is $C_{1-2}$alkyloxycarbonyl, hydroxycarbonyl or tetrahydropyranyloxyaminocarbonyl.

Groups of interesting, preferred, more preferred and most preferred compounds can be defined for the compounds of formula (II), in accordance with the groups defined for the compounds of formula (I).

a) Intermediates of formula (II-a) may be prepared by reacting an intermediate of formula (III) with an intermediate of formula (II), wherein Q is hydroxycarbonyl, herein referred to as intermediates of formula (II-b), in the presence of appropriate reagents such as N'-(ethylcarbonimidoyl)-N,N-dimethyl-1,3-propanediamine, monohydrochloride (EDC) and 1-hydroxy-1H-benzotriazole (HOBT). The reaction may be performed in the presence of a base such as triethylamine, in a suitable solvent, such as, a mixture of dichloromethane and tetrahydrofuran.

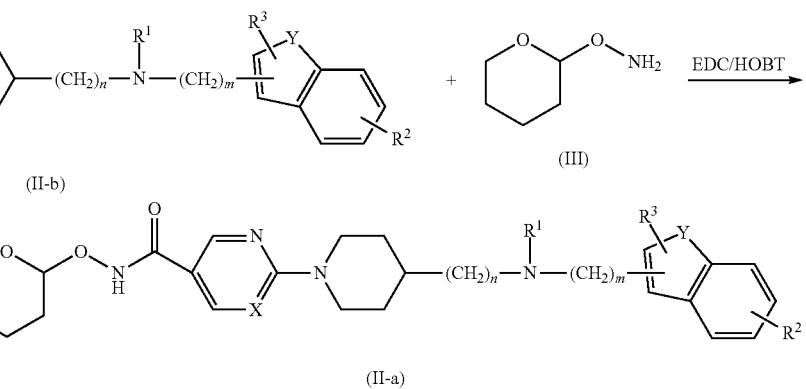

$R^2$ is hydrogen, hydroxy, amino, halo, $C_{1-6}$alkyl, cyano, $C_{2-6}$alkenyl, polyhalo$C_{1-6}$alkyl, nitro, phenyl, $C_{1-6}$alkylcarbonyl, hydroxycarbonyl, $C_{1-6}$alkylcarbonylamino, $C_{1-6}$alkyloxy, or mono- or di($C_{1-6}$alkyl)amino;

$R^3$ is hydrogen, $C_{1-6}$alkyl, or $C_{1-6}$alkyloxy;

b) Intermediates of formula (II-a) may also be prepared by reacting an intermediate of formula (VI) with the appropriate carboxaldehyde of formula (V), wherein t is an integer with value 0 or 1, and when t is 0 then a direct bond is intended, in the presence of an appropriate reagent, such as a sodium borohydride, in a suitable solvent such as dichloroethane or methanol.

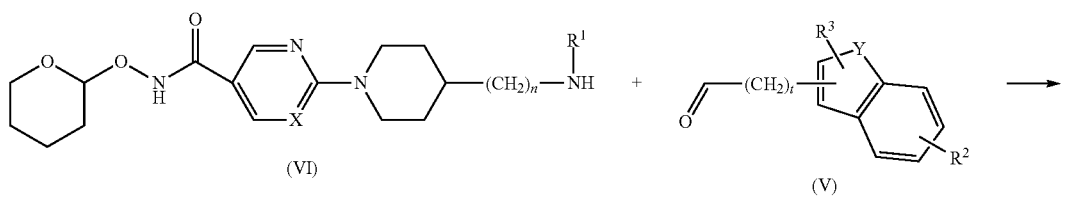

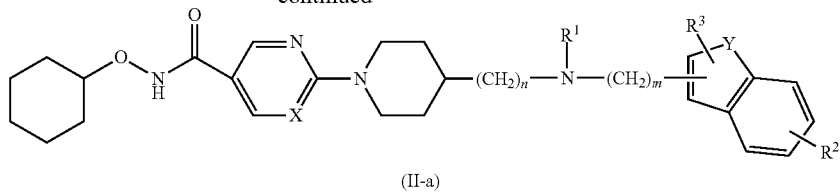

(II-a)

c) Intermediates of formula (II-b) may be prepared by reacting an intermediate of formula (II), wherein Q is methyl- or ethyloxycarbonyl ($C_{1-2}$alkyl), herein referred to as intermediates of formula (II-c), with an appropriate acidic solution, e.g. hydrochloric acid, or basic solution, e.g. hydrogen bromide or sodiumhydroxide, in a suitable solvent e.g. an alcohol, such as ethanol or propanol.

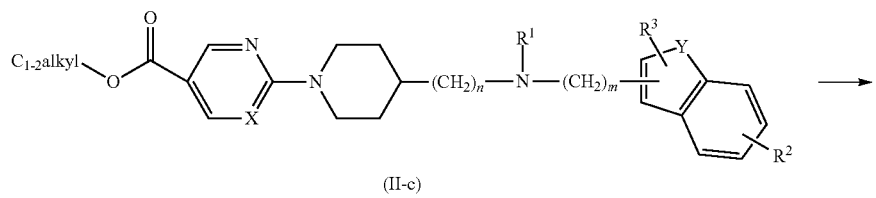

(II-c)

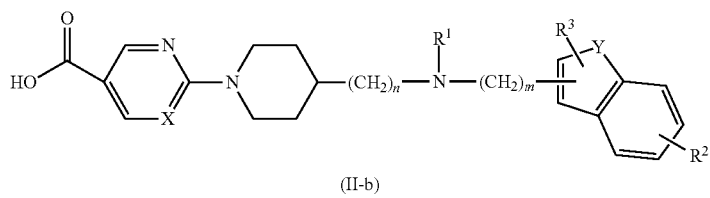

(II-b)

d) The intermediates of formula (II-c) may be prepared by reacting the carboxylic acid ethyl ester of formula (IV) with the appropriate carboxaldehyde of formula (V), in the presence of an appropriate reagent, such as a sodium borohydride e.g. sodium tetrahydroborate, in a suitable solvent such as an alcohol e.g. methanol.

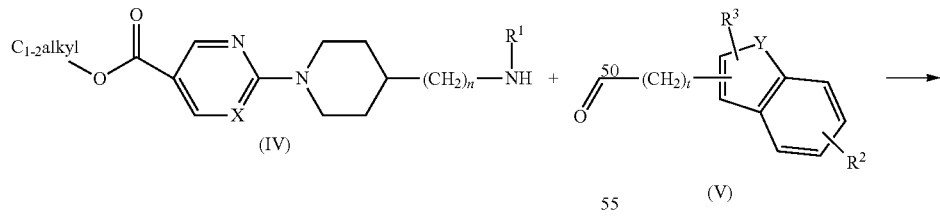

(IV)    (V)

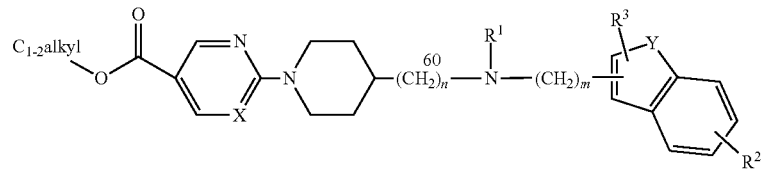

(II-c)

e) In an identical way, the intermediates of formula (II-c) may be prepared by reacting an intermediate of formula (XIV) with the appropriate intermediate of formula (XV), in the presence of an appropriate reagent, such as a sodium borohydride e.g. sodium tetrahydroborate, in a suitable solvent such as an alcohol e.g. methanol.

appropriate base such as, for example, an alkali or earth alkaline metal carbonate or hydrogen carbonate, e.g. triethylamine or sodium carbonate, may be utilized to pick up the acid which is liberated during the course of the reaction. A small amount of an appropriate metal iodide, e.g., sodium or potassium iodide may be added to

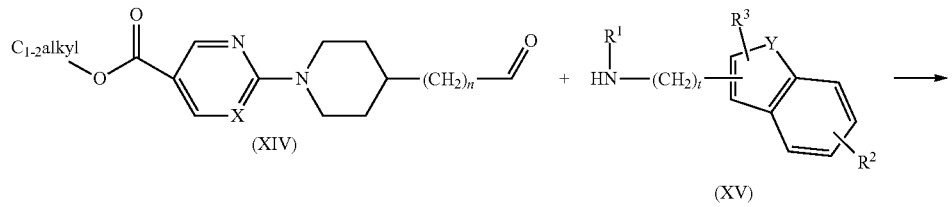

(XIV) + (XV)

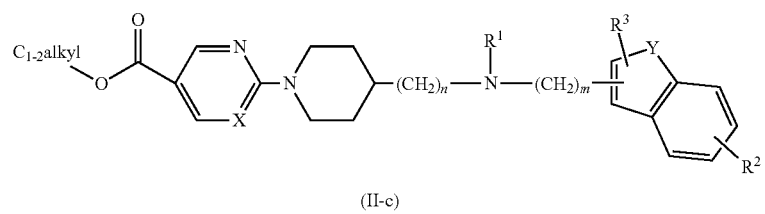

(II-c)

f) Intermediates of formula (II-c) may also be prepared by reacting an intermediate of formula (X) with an intermediate of formula (XI) wherein W is an appropriate leaving group such as, for example, halo, e.g. fluoro, chloro, bromo or iodo, or a sulfonyloxy radical such as methylsulfonyloxy, 4-methylphenylsulfonyloxy and the like. The reaction can be performed in a reaction-inert solvent such as, for example, an alcohol, e.g. methanol, ethanol, 2-methoxyethanol, propanol, butanol and the like; an ether, e.g. 4,4-dioxane, 1,1'-oxybispropane and the like; a ketone, e.g. 4-methyl-2-pentanone; or N,N-dimethylformamide, nitrobenzene, acetonitrile and the like. The addition of an promote the reaction. Stirring may enhance the rate of the reaction. The reaction may conveniently be carried out at a temperature ranging between room temperature and the reflux temperature of the reaction mixture and, if desired, the reaction may be carried out at an increased pressure.

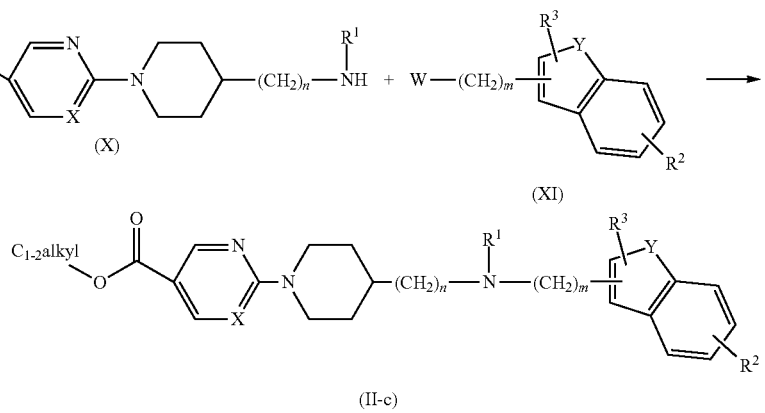

(X) + (XI)

(II-c)

g) In an identical way, intermediates of formula (II-c) may be prepared by reacting an intermediate of formula (XII) with an intermediate of formula (XIII), wherein W is an appropriate leaving group as described above.

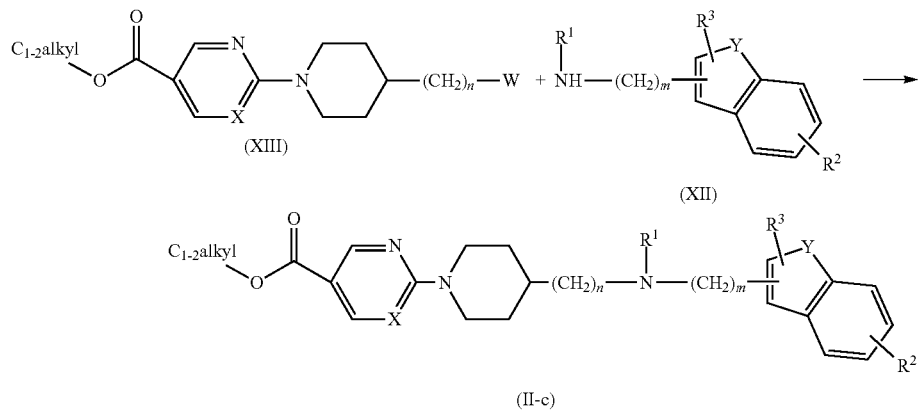

The intermediates of formula (VI) may be prepared by reacting the intermediate of formula (VII) with piperidine in a suitable solvent e.g. dichloromethane.

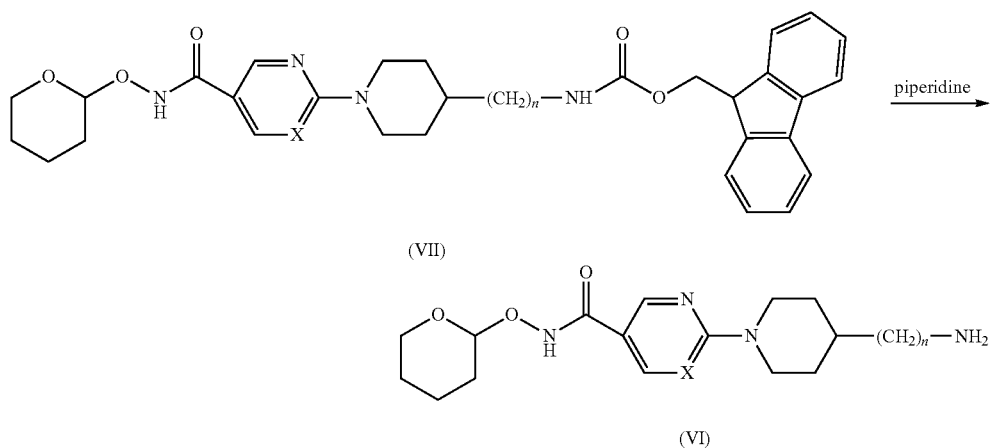

The intermediates of formula (VII) may be prepared by reacting an intermediate of formula (VIII) with an intermediate of formula (III), in the presence of appropriate reagents such as N'-(ethylcarbonimidoyl)-N,N-dimethyl-1,3-propanediamine, monohydrochloride (EDC) and 1-hydroxy-1H-benzotriazole (HOBT). The reaction may be performed in the presence of a base such as triethylamine, in a suitable solvent, such as, a mixture of dichloromethane and tetrahydrofuran.

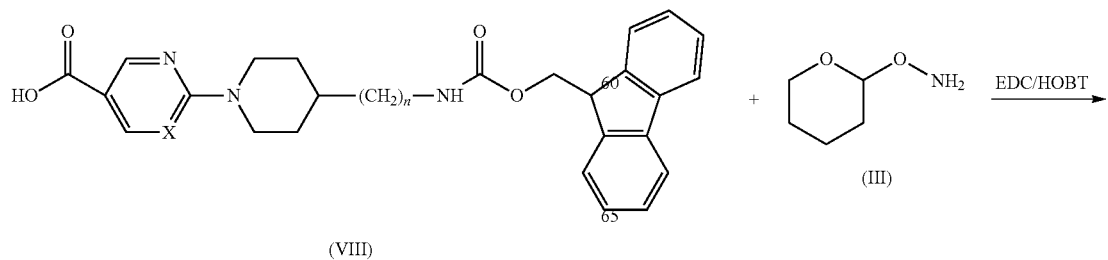

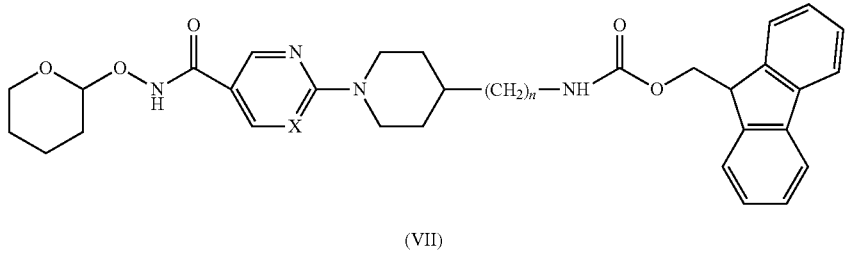

(VII)

Intermediates of formula (VIII) may be prepared by reacting an intermediate of formula (IX) with an intermediate of formula (IV), wherein R¹ is hydrogen, herein referred to as intermediates of formula (IV-a), in the presence of sodium hydroxide, in a suitable solvent, such as tetrahydrofuran, followed by neutralization with hydrochloric acid and addition of sodium carbonate.

(VI-a)

(IX)

(VIII)

The compounds of formula (I) and some of the intermediates may have at least one stereogenic centre in their structure. This stereogenic centre may be present in an R or an S configuration.

The compounds of formula (I) as prepared in the hereinabove described processes are generally racemic mixtures of enantiomers, which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a histone deacetylase (HDAC) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the inhibition of tumour growth both directly by causing growth arrest, terminal differentiation and/or apoptosis of cancer cells, and indirectly, by inhibiting neovascularization of tumours.

This invention also provides a method for inhibiting tumour growth by administering an effective amount of a compound of the present invention, to a subject, e.g. a mammal (and more particularly a human) in need of such treatment. In particular, this invention provides a method for inhibiting the growth of tumours by the administration of an effective amount of the compounds of the present invention. Examples of tumours which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumours of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumours of mesenchymal origin (e.g. fibrosarcomas and rhabdomyosarcomas), melanomas, teratocarcinomas, neuroblastomas, gliomas, benign tumour of the skin (e.g. keratoacanthomas), breast carcinoma (e.g. advanced breast cancer), kidney carcinoma, ovary carcinoma, bladder carcinoma and epidermal carcinoma.

The compound according to the invention may be used for other therapeutic purposes, for example:
  a) the sensitisation of tumours to radiotherapy by administering the compound according to the invention before, during or after irradiation of the tumour for treating cancer;
  b) treating arthropathies and osteopathological conditions such as rheumatoid arthritis, osteoarthritis, juvenile arthritis, gout, polyarthritis, psoriatic arthritis, ankylosing spondylitis and systemic lupus erythematosus;
  c) inhibiting smooth muscle cell proliferation including vascular proliferative disorders, atherosclerosis and restenosis;

d) treating inflammatory conditions and dermal conditions such as ulcerative colitis, Crohn's disease, allergic rhinitis, graft vs. host disease, conjunctivitis, asthma, ARDS, Behcets disease, transplant rejection, uticaria, allergic dermatitis, alopecia greata, scleroderma, exanthema, eczema, dermatomyositis, acne, diabetes, systemic lupus erythematosis, Kawasaki's disease, multiple sclerosis, emphysema, cystic fibrosis and chronic bronchitis;

e) treating endometriosis, uterine fibroids, dysfunctional uterine bleeding and endometrial hyperplasia;

f) treating ocular vascularisation including vasculopathy affecting retinal and choroidal vessels;

g) treating a cardiac dysfunction;

h) inhibiting immunosuppressive conditions such as the treatment of HIV infections;

i) treating renal dysfunction;

j) suppressing endocrine disorders;

k) inhibiting dysfunction of gluconeogenesis;

l) treating a neuropathology for example Parkinson's disease or a neuropathology that results in a cognitive disorder, for example, Alzheimer's disease or polyglutamine related neuronal diseases;

m) treating psychiatric disorders for example schizophrenia, bipolar disorder, depression, anxiety and psychosis;

n) inhibiting a neuromuscular pathology, for example, amylotrophic lateral sclerosis;

o) treating spinal muscular atrophy;

p) treating other pathologic conditions amenable to treatment by potentiating expression of a gene;

q) enhancing gene therapy;

r) inhibiting adipogenesis;

s) treating parasitosis such as malaria.

Hence, the present invention discloses the compounds of formula (I) for use as a medicine as well as the use of these compounds of formula (I) for the manufacture of a medicament for treating one or more of the above mentioned conditions.

The compounds of formula (I), the pharmaceutically acceptable acid addition salts and stereoisomeric forms thereof can have valuable diagnostic properties in that they can be used for detecting or identifying a HDAC in a biological sample comprising detecting or measuring the formation of a complex between a labelled compound and a HDAC.

The detecting or identifying methods can use compounds that are labelled with labelling agents such as radioisotopes, enzymes, fluorescent substances, luminous substances, etc. Examples of the radioisotopes include $^{125}$I, $^{131}$I, $^3$H and $^{14}$C. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

As another aspect of the present invention a combination of a HDAC-inhibitor with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents. Examples of anti-cancer agents are:

platinum coordination compounds for example cisplatin, carboplatin or oxalyplatin;

taxane compounds for example paclitaxel or docetaxel;

topoisomerase I inhibitors such as camptothecin compounds for example irinotecan or topotecan;

topoisomerase II inhibitors such as anti-tumour podophyllotoxin derivatives for example etoposide or teniposide;
anti-tumour vinca alkaloids for example vinblastine, vincristine or vinorelbine;
anti-tumour nucleoside derivatives for example 5-fluorouracil, gemcitabine or capecitabine;
alkylating agents such as nitrogen mustard or nitrosourea for example cyclophosphamide, chlorambucil, carmustine or lomustine;
anti-tumour anthracycline derivatives for example daunorubicin, doxorubicin, idarubicin or mitoxantrone;
HER2 antibodies for example trastuzumab;
estrogen receptor antagonists or selective estrogen receptor modulators for example tamoxifen, toremifene, droloxifene, faslodex or raloxifene;
aromatase inhibitors such as exemestane, anastrozole, letrazole and vorozole;
differentiating agents such as retinoids, vitamin D and retinoic acid metabolism blocking agents (RAMBA) for example accutane;
DNA methyl transferase inhibitors for example azacytidine;
kinase inhibitors for example flavoperidol, imatinib mesylate or gefitinib;
farnesyltransferase inhibitors;
other HDAC inhibitors;
inhibitors of the ubiquitin-proteasome pathway for example Velcade; or
Yondelis.

The term "platinum coordination compound" is used herein to denote any tumour cell growth inhibiting platinum coordination compound which provides platinum in the form of an ion.

The term "taxane compounds" indicates a class of compounds having the taxane ring system and related to or derived from extracts from certain species of yew (Taxus) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree Camptothecin acuminata and the Indian tree Nothapodytes foetida.

The term "podophyllotoxin compounds" is used to indicate compounds that are related to or derived from the parent podophyllotoxin, which is extracted from the mandrake plant.

The term "anti-tumour vinca alkaloids" is used to indicate compounds that are related to or derived from extracts of the periwinkle plant (Vinca rosea).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus *Strep. peuticus* var. *caesius* and their derivatives, characterised by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affiniity and specificity to the extracellular domain of the HER2 receptor.

Many breast cancers have estrogen receptors and growth of these tumours can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, modulating its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promotors of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The term "other HDAC inhibitors" comprises but is not limited to:

carboxylates for example butyrate, cinnamic acid, 4-phenylbutyrate or valproic acid;

hydroxamic acids for example suberoylanilide hydroxamic acid (SAHA), piperazine containing SAHA analogues, biaryl hydroxamate A-161906 and its carbozolylether-, tetrahydropyridine- and tetralone-analogues, bicyclic aryl-N-hydroxycarboxamides, pyroxamide, CG-1521, PXD-101, sulfonamide hydroxamic acid, LAQ-824, LBH-589, trichostatin A (TSA), oxamflatin, scriptaid, scriptaid related tricyclic molecules, m-carboxy cinnamic acid bishydroxamic acid (CBHA), CBHA-like hydroxamic acids, trapoxin-hydroxamic acid analogue, R306465 and related benzoyl- and heteroaryl-hydroxamic acids, aminosuberates and malonyldiamides;

cyclic tetrapeptides for example trapoxin, apidicin, depsipeptide, spiruchostatin-related compounds, RedFK-228, sulfhydryl-containing cyclic tetrapeptides (SCOPs), hydroxamic acid containing cyclic tetrapeptides (CHAPs), TAN-174s and azumamides;

benzamides for example MS-275 or CI-994, or depudecin.

The term "inhibitors of the ubiquitin-proteasome pathway" is used to identify compounds that inhibit the targeted destruction of cellular proteins in the proteasome, including cell cycle regulatory proteins.

For the treatment of cancer the compounds according to the present invention may be administered to a patient as described above, in conjunction with irradiation. Irradiation means ionising radiation and in particular gamma radiation, especially that emitted by linear accelerators or by radionuclides that are in common use today. The irradiation of the tumour by radionuclides can be external or internal.

The present invention also relates to a combination according to the invention of an anti-cancer agent and a HDAC inhibitor according to the invention.

The present invention also relates to a combination according to the invention for use in medical therapy for example for inhibiting the growth of tumour cells.

The present invention also relates to a combinations according to the invention for inhibiting the growth of tumour cells.

The present invention also relates to a method of inhibiting the growth of tumour cells in a human subject which comprises administering to the subject an effective amount of a combination according to the invention.

This invention further provides a method for inhibiting the abnormal growth of cells, including transformed cells, by administering an effective amount of a combination according to the invention.

The other medicinal agent and HDAC inhibitor may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and HDAC inhibitor being administered, their route of administration, the particular tumour being treated and the particular host being treated. The optimum method and order of administration and the dosage amounts and regime can be readily determined by those skilled in the art using conventional methods and in view of the information set out herein.

The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

Trastuzumab is advantageously administered in a dosage of 1 to 5 mg per square meter (mg/m$^2$) of body surface area, particularly 2 to 4 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

These dosages may be administered for example once, twice or more per course of treatment, which may be repeated for example every 7, 14, 21 or 28 days.

In view of their useful pharmacological properties, the components of the combinations according to the invention, i.e. the other medicinal agent and the HDAC inhibitor may be formulated into various pharmaceutical forms for administration purposes. The components may be formulated separately in individual pharmaceutical compositions or in a unitary pharmaceutical composition containing both components.

The present invention therefore also relates to a pharmaceutical composition comprising the other medicinal agent and the HDAC inhibitor together with one or more pharmaceutical carriers.

The present invention also relates to a combination according to the invention in the form of a pharmaceutical composition comprising an anti-cancer agent and a HDAC inhibitor according to the invention together with one or more pharmaceutical carriers.

The present invention further relates to the use of a combination according to the invention in the manufacture of a pharmaceutical composition for inhibiting the growth of tumour cells.

The present invention further relates to a product containing as first active ingredient a HDAC inhibitor according to the invention and as second active ingredient an anticancer agent, as a combined preparation for simultaneous, separate or sequential use in the treatment of patients suffering from cancer.

Experimental Part

The following examples are provided for purposes of illustration.

Hereinafter, "DCM" is defined as dichloromethane, "DIPE" is defined as diisopropyl ether, "DMA" is defined as is defined as N,N-dimethylacetamide, "DMSO" is defined as dimethylsulfoxide, "EDC" is defined as N'-(ethylcarbonimidoyl)-N,N-dimethyl-1,3-propanediamine, monohydrochloride, "EtOAc" is defined as ethyl acetate, "EtOH" is defined as ethanol, "HOBt" is defined as 1-hydroxy-1H-benzotriazole, "MeOH" is defined as methanol, "TFA" is defined as trifluoroacetic acid and "THF" is defined as tetrahydrofuran.

A. Preparation of the Intermediate Compounds

EXAMPLE A1 a) Preparation of Intermediate 1

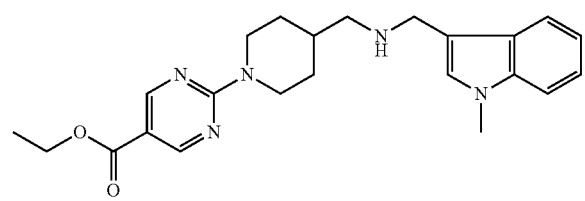 [SMILES: CCOC(=O)c1cnc(N2CCC(CNCc3cn(C)c4ccccc34)CC2)nc1]

A mixture of 2-[4-(aminomethyl)-1-piperidinyl]-5-pyrimidinecarboxylic acid, ethyl ester (0.0114 mol), 1-methyl-1H-indole-3-carboxaldehyde (0.017 mol) and MgSO₄ (0.5 g) in MeOH (80 ml) was stirred and refluxed for 15 hours, then cooled to room temperature. Sodium tetrahydroborate (0.018 mol) was added portionwise. The mixture was stirred at room temperature 5 hours, poured out into water and extracted with EtOAc. The organic layer was separated, dried (MgSO₄), filtered, and the solvent was evaporated. The residue (6.6 g) was purified by column chromatography over silica gel (15-40 μm) (eluent: DCM/MeOH/NH₄OH 94/6/0.5). The pure fractions were collected and the solvent was evaporated, yielding 4.3 g (90%) of intermediate 1.

b) Preparation of Intermediate 2

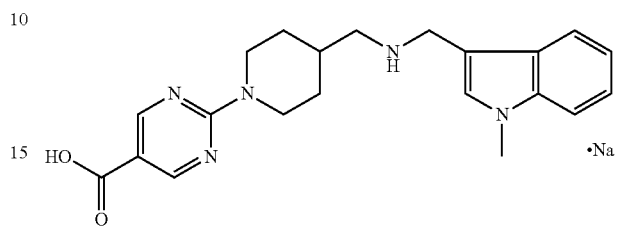

A mixture of intermediate 1 (0.0037 mol) and sodium hydroxide (0.0074 mol) in EtOH (60 ml) was stirred at 50° C. for 15 hours, then cooled to room temperature and the solvent was evaporated till dryness, yielding 1.5 g (100%) of intermediate 2.

c) Preparation of Intermediate 3

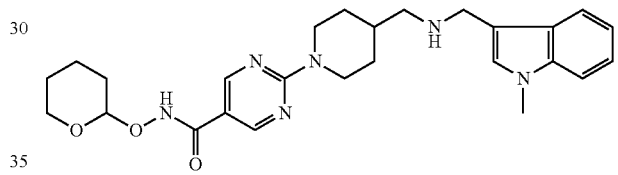

EDC (0.0075 mol), then HOBt (0.0075 mol) then O-(tetrahydro-2H-pyran-2-yl)-hydroxylamine (0.015 mol) were added at room temperature to a mixture of intermediate 2 (0.005 mol) in DCM (100 ml) and THF (100 ml) under N₂ flow. The mixture was stirred at 40° C. for 4 hours, poured out into ice water and extracted with DCM. The organic layer was separated, dried (MgSO₄), filtered, and the solvent was evaporated. The residue (4 g) was purified by column chromatography over silica gel (15-40 μm) (eluent: DCM/MeOH/NH₄OH 96/4/0.5). The pure fractions were collected and the solvent was evaporated, yielding 1 g (42%) of intermediate 3. A fraction (0.051 g) was crystallized from DIPE. The precipitate was filtered off and dried, yielding 0.03 g of intermediate 3, melting point 70° C.

EXAMPLE A2 a) Preparation of Intermediate 4

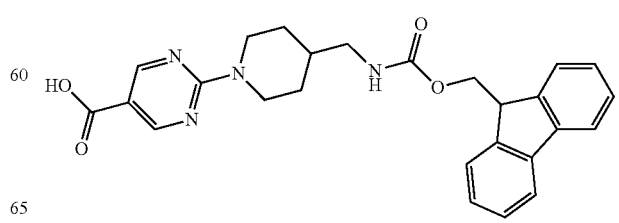

A mixture of 2-[4-(aminomethyl)-1-piperidinyl]-5-pyrimidinecarboxylic acid, ethyl ester (0.0072 mol) in THF (40 ml) and sodium hydroxide 1N (40 ml) was stirred at room temperature overnight. Hydrochloric acid 1N (40 ml) was added. The mixture was stirred for 10 minutes. Sodium carbonate (0.0216 mol) was added. The mixture was stirred for 10 minutes. 1-[[(9H-fluoren-9-ylmethoxy)carbonyl]oxy]-2,5-pyrrolidinedione (0.0072 mol) was added portionwise. The mixture was stirred at room temperature for 6 hours, then cooled to 0° C. and acidified with hydrochloric acid. The precipitate was filtered, washed with diethyl ether and dried, yielding 4.1 g (100%) of intermediate 4.

b) Preparation of Intermediate 5

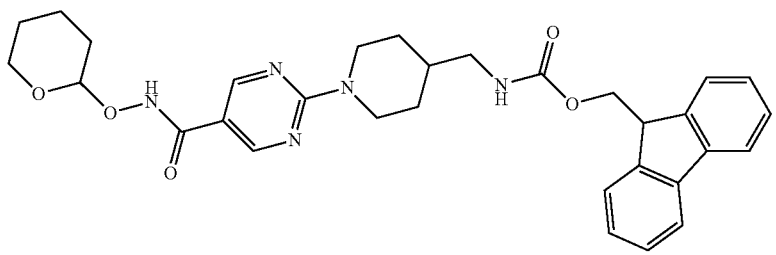 [SMILES: O=C(NCC1CCN(c2ncc(C(=O)NOC3CCCCO3)cn2)CC1)OCC1c2ccccc2-c2ccccc21]

Triethylamine (0.02 mol), EDC (0.0082 mol) and HOBt (0.0082 mol) were added at room temperature to a mixture of intermediate 4 (0.0068 mol) in DCM/THF (200 ml) under $N_2$ flow. The mixture was stirred at room temperature for 15 minutes. O-(tetrahydro-2H-pyran-2-yl)-hydroxylamine (0.0082 mol) was added. The mixture was stirred at room temperature for 48 hours, poured out into water and extracted with DCM. The organic layer was washed with NaHCO$_3$ 10%, dried (MgSO$_4$), filtered, and the solvent was evaporated. The residue (4 g) was purified by column chromatography over silica gel (15-40 μm) (eluent: DCM/MeOH/NH$_4$OH 98/2/0.1). The pure fractions were collected and the solvent was evaporated, yielding 3.4 g (89%) of intermediate 5.

c) Preparation of Intermediate 6

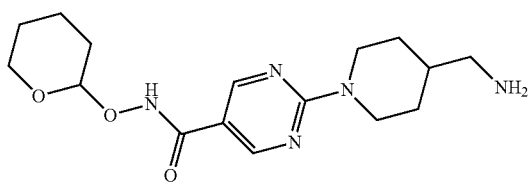 [SMILES: NCC1CCN(c2ncc(C(=O)NOC3CCCCO3)cn2)CC1]

A mixture of intermediate 5 (0.0355 mol) and piperidine (0.089 mol) in DCM (400 ml) was stirred at 35° C. during 72 hours. The solvent was evaporated. The residue was purified by column chromatography over silica gel (15-40 μm) (eluent: DCM/MeOH/NH$_4$OH 80/20/2). The pure fractions were collected and the solvent was evaporated, yielding 6.7 g (56%). Part of the residue (0.79 g) was crystallized from diethyl ether. The precipitate was filtered off and dried, yielding 0.62 g of intermediate 6, melting point 129° C.

d) Preparation of Intermediate 7

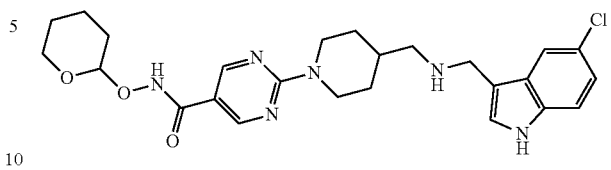

A mixture of intermediate 6 (0.0009 mol) and 5-chloro-1H-indole-3-carboxaldehyde (0.0012 mol) in 1,2-dichloroethane (30 ml) was stirred at room temperature overnight. Tris(acetato-α-O-)hydro-borate(1-), sodium (0.0013 mol) was added portionwise. The mixture was stirred at room temperature for 4 hours, poured out into water/NaOH 3N and extracted with DCM. The organic layer was separated, dried (MgSO$_4$), filtered, and the solvent was evaporated. The residue (0.5 g) was purified by column chromatography over silica gel (15-40 μm) (eluent DCM/MeOH/NH$_4$OH 93/7/0.5). Two fractions were collected and the solvent was evaporated, yielding 0.07 g (16%) of intermediate 7.

EXAMPLE A3 a) Preparation of Intermediate 8

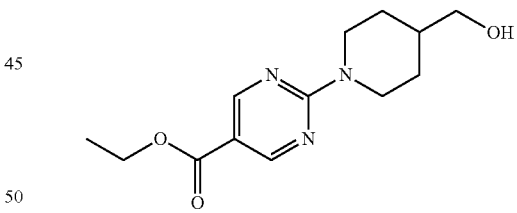

A solution of 2-(methylsulfonyl)-5-pyrimidinecarboxylic acid, ethyl ester (0.094 mol) in acetonitrile (40 ml) was added at 10° C. to a suspension of 4-piperidinemethanol (0.086 mol) and potassium carbonate (0.172 mol) in acetonitrile (200 ml) under N$_2$ flow. The mixture was brought to room temperature, then stirred for 4 hours, poured out into water and extracted with EtOAc. The organic layer was separated, dried (MgSO$_4$), filtered, and the solvent was evaporated. The residue (23 g) was crystallized from acetonitrile/diethyl ether. The precipitate was filtered off and dried, yielding 7.8 g (34%) of intermediate 8. The mother layer was evaporated. The residue (17 g) was purified by column chromatography over silica gel (20-45 μm) (eluent: DCM/MeOH/NH$_4$OH 97/3/0.1). The pure fractions were collected and the solvent was evaporated, yielding 4.6 g (20%) of intermediate 8, melting point 129° C.

b) Preparation of Intermediate 9

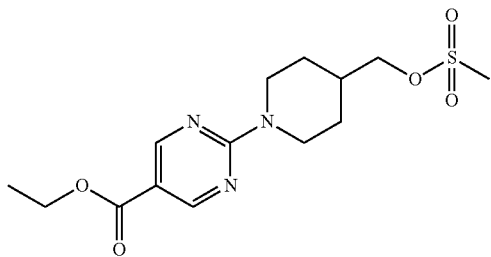 [SMILES: CCOC(=O)c1cnc(N2CCC(COS(C)(=O)=O)CC2)nc1]

Triethylamine (0.038 mol) then methanesulfonyl chloride (0.025 mol) were added at 0° C. to a solution of intermediate 8 (0.0189 mol) in DCM (80 ml) under $N_2$ flow. The mixture was stirred at 0° C. for 2 hours and poured out into ice water. The organic layer was separated, dried ($MgSO_4$), filtered, and the solvent was evaporated, yielding 6.5 g (100%) of intermediate 9.

c) Preparation of Intermediate 10

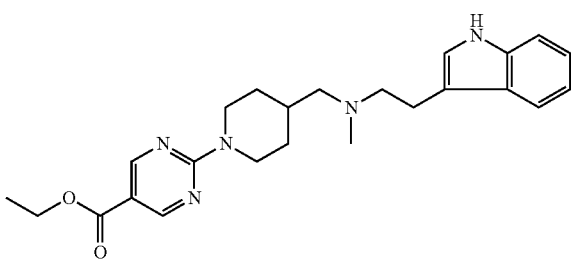 [SMILES: CCOC(=O)c1cnc(N2CCC(CN(C)CCc3c[nH]c4ccccc34)CC2)nc1]

A mixture of intermediate 9 (0.0189 mol), N-methyl-1H-indole-3-ethanamine (0.0172 mol) and potassium carbonate (0.0344 mol) in acetonitrile (180 ml) was stirred and refluxed for 24 hours, poured out into water and extracted with EtOAc. The organic layer was separated, dried ($MgSO_4$), filtered, and the solvent was evaporated. The residue (8.5 g) was purified by column chromatography over silica gel (70-200 μm) (eluent: DCM/MeOH/$NH_4OH$ 98/2/0 to 97/3/0.1). The pure fractions were collected and the solvent was evaporated, yielding 1.25 g (20%) of intermediate 10.

d) Preparation of Intermediate 11

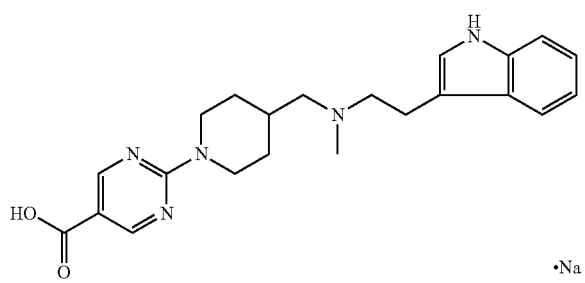

A mixture of intermediate 10 (0.003 mol) and sodium hydroxide (0.006 mol) in EtOH (80 ml) was stirred and refluxed overnight, then cooled to room temperature and the solvent was evaporated till dryness, yielding 1.3 g (100%) of intermediate 11, mp. >260° C.

e) Preparation of Intermediate 12

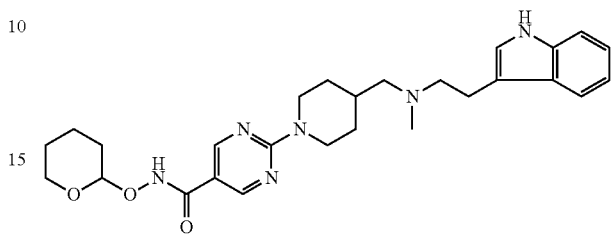

EDC (0.0045 mol) then HOBt (0.0045 mol) were added at room temperature to a mixture of intermediate 11 (0.003 mol) in THF (100 ml) and DCM (100 ml) under $N_2$ flow. The mixture was stirred at room temperature for 15 minutes. O-(tetrahydro-2H-pyran-2-yl)-hydroxylamine (0.012 mol) was added. The mixture was stirred at room temperature for 72 hours, poured out into water and extracted with DCM. The organic layer was separated, dried ($MgSO_4$), filtered, and the solvent was evaporated. The residue (3 g) was purified by column chromatography over silica gel (15-40 μm)(eluent: DCM/MeOH/$NH_4OH$ 94/6/0.1). The pure fractions were collected and the solvent was evaporated. The residue (0.82 g) was taken up in diethyl ether. The precipitate was filtered off and dried, yielding 0.78 g of intermediate 12, melting point 154° C.

EXAMPLE A4 a) Preparation of Intermediate 13

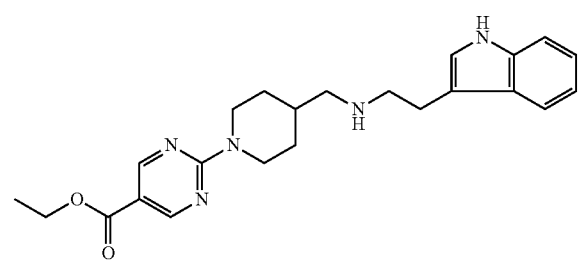 [SMILES: CCOC(=O)c1cnc(N2CCC(CNCCc3c[nH]c4ccccc34)CC2)nc1]

A mixture of 2-[4-(aminomethyl)-1-piperidinyl]-5-pyrimidinecarboxylic acid, ethyl ester (0.0049 mol), 1H-indole-3-ethanol, methanesulfonate (ester) (0.0054 mol) and potassium carbonate (0.01 mol) in acetonitrile (20 ml) was stirred and refluxed overnight, then cooled, poured out into ice water and extracted with DCM. The organic layer was separated, dried ($MgSO_4$), filtered, and the solvent was evaporated. The residue (2.2 g) was purified by column chromatography over silica gel (15-40 μm) (eluent: DCM/MeOH/$NH_4OH$ 96/4/0.2). The pure fractions were collected and the solvent was evaporated, yielding 0.442 g (22%) of intermediate 13, melting point 238° C.

b) Preparation of Intermediate 14

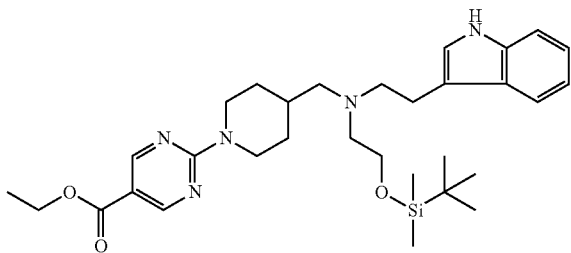 [SMILES: CCOC(=O)c1cnc(N2CCC(CN(CCO[Si](C)(C)C(C)(C)C)CCc3c[nH]c4ccccc34)CC2)nc1]

A mixture of intermediate 13 (0.0025 mol), (2-bromoethoxy)(1,1-dimethylethyl)dimethyl-silane (0.0034 mol) and N-ethyl-N-(1-methylethyl)-2-propanamine (0.0038 mol) in DMSO (20 ml) was stirred at 50° C. for 15 hours, then cooled to room temperature, poured out into ice water and extracted with DCM. The organic layer was separated, dried (MgSO$_4$), filtered, and the solvent was evaporated. The residue (1.7 g) was purified by column chromatography over silica gel (15-40 μm) (eluent: DCM/MeOH/NH$_4$OH 98/2/0.1). The pure fractions were collected and the solvent was evaporated, yielding 0.76 g (54%) of intermediate 14.

c) Preparation of Intermediate 15

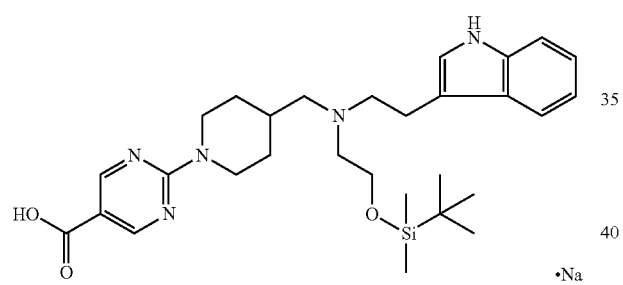

A mixture of intermediate 14 (0.0013 mol) and sodium hydroxide (0.0027 mol) in EtOH (40 ml) was stirred at 80° C. overnight, then cooled to room temperature and the solvent was evaporated, yielding 0.758 (100%) of intermediate 15.

d) Preparation of Intermediate 16

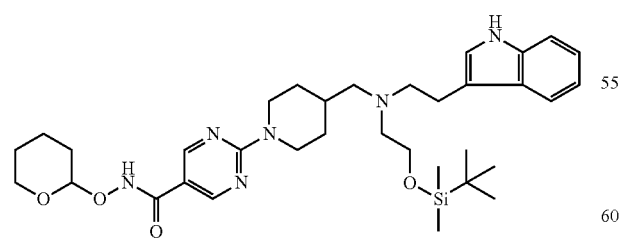

EDC (0.002 mol) then HOBt (0.002 mol) were added at room temperature to a mixture of intermediate 15 (0.0013 mol) in THF (80 ml) and DCM (80 ml) under N$_2$ flow. The mixture was stirred at room temperature for 15 minutes. O-(tetrahydro-2H-pyran-2-yl)-hydroxylamine (0.0068 mol) was added. The mixture was stirred at room temperature for 72 hours, poured out into water and extracted with DCM. The organic layer was separated, dried (MgSO$_4$), filtered, and the solvent was evaporated. The residue (1.3 g) was purified by column chromatography over silica gel (15-40 μm)(eluent: DCM/MeOH/NH$_4$OH 95/5/0.1). The pure fractions were collected and the solvent was evaporated, yielding 0.38 g of intermediate 16.

e) Preparation of Intermediate 17

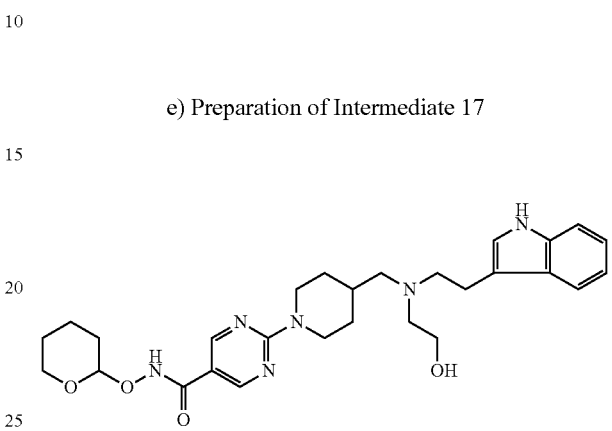

A mixture of intermediate 16 (0.0011 mol) and tetrabutylammonium fluoride (0.0032 mol) in THF (10 ml) was stirred at room temperature for 72 hours, poured out into water and extracted with EtOAc. The organic layer was washed with water, dried (MgSO$_4$), filtered and the solvent was evaporated, yielding 0.5 g (88%) of intermediate 17.

EXAMPLE A5 a) Preparation of Intermediate 45

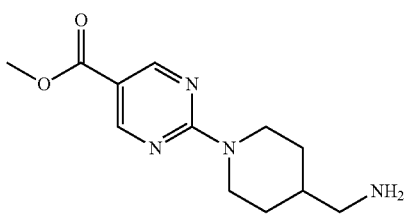 [SMILES: COC(=O)c1cnc(N2CCC(CN)CC2)nc1]

A solution of 2-chloro-5-pyrimidinecarboxylic acid, methyl ester (0.058 mol) in DMA (80 ml) was added dropwise to a solution of 4-piperidinemethanamine (0.116 mol) and N-ethyldiisopropylamine (0.145 mol) in DMA (150 ml) under N$_2$ flow. The mixture was stirred at room temperature for 1 hour and 30 minutes, poured out into ice water and extracted with EtOAc, then with DCM. The organic layer was washed with water, dried (MgSO$_4$), filtered and the solvent was evaporated. The residue was crystallized from DIPE. The precipitate was filtered off and dried, yielding 10 g (65%) of intermediate 45.

b) Preparation of Intermediate 46

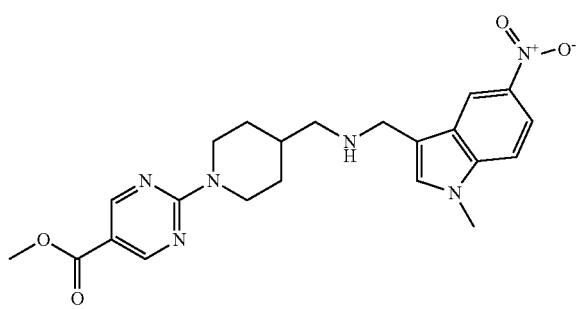 [SMILES: COC(=O)c1cnc(N2CCC(CNCc3cn(C)c4ccc([N+](=O)[O-])cc34)CC2)nc1]

A mixture of intermediate 45 (0.0024 mol), 1-methyl-5-nitro-1H-indole-3-carboxaldehyde (0.0036 mol) and MgSO$_4$ (0.25 g) in MeOH (80 ml) was stirred at 60° C. overnight, then cooled to room temperature. Sodium tetrahydroborate (0.0041 mol) was added portionwise. The mixture was stirred at room temperature for 18 hours, poured out into water and extracted with EtOAc. The organic layer was separated, dried (MgSO$_4$), filtered and the solvent was evaporated. The residue (1.1 g) was crystallized from acetonitrile. The precipitate was filtered off and dried, yielding 0.9 g (86%) of intermediate 46, melting point: 150° C.

c) Preparation of Intermediate 47

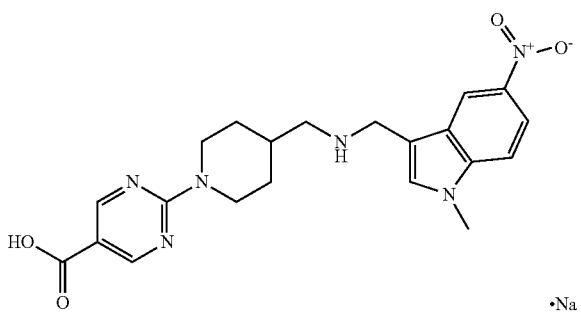

·Na

A mixture of intermediate 46 (0.002 mol) and sodium hydroxide (0.008 mol) in EtOH (60 ml) was stirred at 60° C. overnight, then cooled to room temperature and evaporated. The residue was taken up in diethyl ether. The precipitate was filtered off and dried, yielding 0.6 g (67%) of intermediate 47.

d) Preparation of Intermediate 48

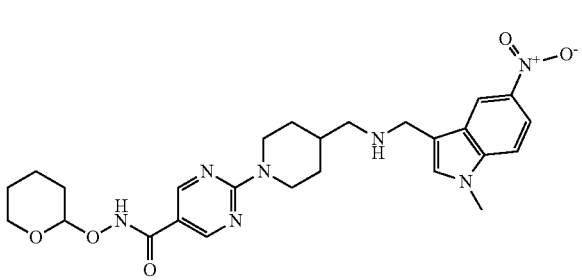 [SMILES: Cn1cc(CNCC2CCN(c3ncc(C(=O)NOC4CCCCO4)cn3)CC2)c2cc([N+](=O)[O-])ccc21]

EDC (0.0019 mol) and HOBt (0.0019 mol) were added at room temperature to a solution of intermediate 47 (0.0013 mol) and triethylamine (0.0039 mol) in DCM/THF (50/50) (100 ml) under N$_2$ flow. The mixture was stirred at room temperature for 15 minutes. O-(tetrahydro-2H-pyran-2-yl)-hydroxylamine (0.0026 mol) was added. The mixture was stirred at room temperature for 72 hours, poured out into water and extracted with DCM. The organic layer was separated, dried (MgSO$_4$), filtered and the solvent was evaporated. The residue (1 g) was purified by column chromatography over kromasil (5 μm) (eluent: DCM/MeOH/NH$_4$OH 98/2/0.2 to 92/8/0.2). The pure fractions were collected and the solvent was evaporated, yielding 0.101 g (15%) of intermediate 48.

EXAMPLE A6 a) Preparation of Intermediate 49

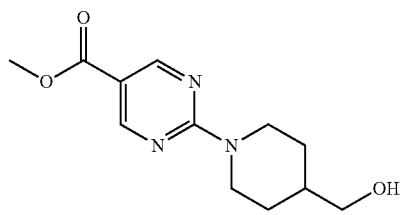 [SMILES: COC(=O)c1cnc(N2CCC(CO)CC2)nc1]

A solution of 2-chloro-5-pyrimidinecarboxylic acid, methyl ester (0.033 mol) in DCM (80 ml) was added at room temperature to a solution of 4-piperidinemethanol (0.066 mol) and N-ethyldiisopropylamine (0.083 mol) in DCM (100 ml) under N$_2$ flow. The mixture was stirred at room temperature for 3 hours and 30 minutes, poured out into ice water and extracted with DCM. The organic layer was separated, dried (MgSO$_4$), filtered and the solvent was evaporated. The residue was taken up in pentane. The precipitate was filtered off and dried, yielding 7.88 g (95%) of intermediate 49.

b) Preparation of Intermediate 50

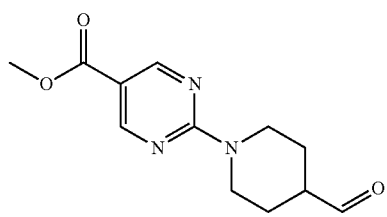 [SMILES: COC(=O)c1cnc(N2CCC(C=O)CC2)nc1]

DMSO (0.058 mol) was added dropwise at −78° C. to a solution of ethanedioyl dichloride (0.0278 mol) in DCM (50 ml) under N$_2$ flow. The mixture was stirred for 15 minutes. A solution of intermediate 49 (0.023 mol) in DCM (200 ml) was added dropwise. The mixture was stirred at −78° C. for 1 hour and 30 minutes. Triethylamine (0.118 mol) was added dropwise. The mixture was stirred at −78° C. for 1 hour, poured out into water and extracted with DCM. The organic layer was separated, dried (MgSO$_4$), filtered and the solvent was evaporated. The residue was crystallized from diethyl ether. The precipitate was filtered off and dried, yielding 3.06 g (54%) of intermediate 50.

c) Preparation of Intermediate 51

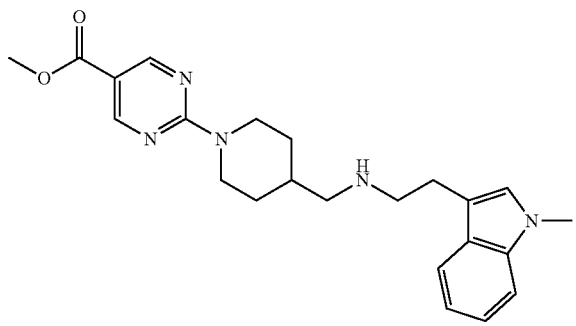

Intermediate 50 (0.0122 mol) was added at 5° C. to a solution of 1-methyl-1H-indole-3-ethanamine (0.0122 mol) in MeOH (270 ml) under $N_2$ flow. The mixture was stirred a few minutes. Sodiumcyanoborohydride (0.0183 mol) and acetic acid (0.0183 mol) were added. The mixture was stirred at room temperature for 48 hours, poured out into potassium carbonate 10% and extracted with DCM. The organic layer was separated, dried ($MgSO_4$), filtered and the solvent was evaporated. The residue (4.9 g) was purified by column chromatography over silica gel (15-40 μm) (eluent: DCM/MeOH/$NH_4OH$ 97/3/0.1). The pure fractions were collected and the solvent was evaporated, yielding 1.2 g (24%) of intermediate 51.

d) Preparation of Intermediate 52

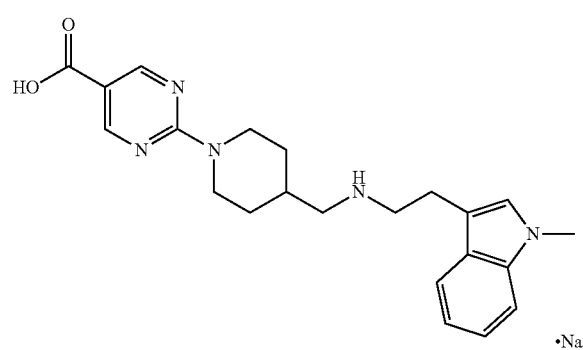

A mixture of intermediate 51 (0.0009 mol) and sodium hydroxide (0.0039 mol) in EtOH (60 ml) was stirred and refluxed for 15 hours, then evaporated till dryness, yielding intermediate 52. This intermediate was used directly in the next reaction step.

e) Preparation of Intermediate 53

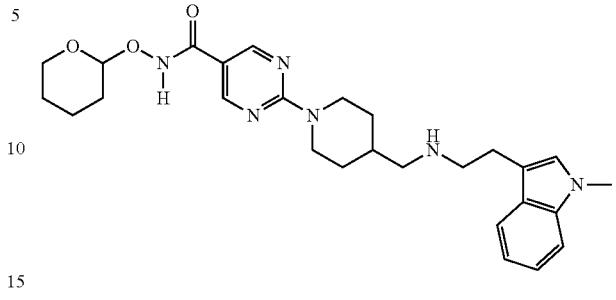

HOBt (0.0019 mol) then EDC (0.0019 mol) were added at room temperature to a solution of intermediate 52 (0.0009 mol) and O-(tetrahydro-2H-pyran-2-yl)-hydroxylamine (0.0019 mol) in DCM/THF (130 ml). The mixture was stirred at room temperature for 48 hours, poured out into water and extracted with DCM. The organic layer was separated, dried ($MgSO_4$), filtered and the solvent was evaporated. The residue (0.93 g) was purified by column chromatography over silica gel (15-40 μm) (eluent: DCM/MeOH/$NH_4OH$ 97/3/0.1). The pure fractions were collected and the solvent was evaporated, yielding 0.155 g (33%) of intermediate 53.

EXAMPLE A7 a) Preparation of Intermediate 54

A mixture of 2-[4-(aminomethyl)-1-piperidinyl]-5-pyrimidinecarboxylic acid, ethyl ester (0.0038 mol), 1-ethyl-1H-indole-3-carboxaldehyde (0.0049 mol) and Pd/C 10% (0.5 g) in MeOH (20 ml) containing 1 ml of a 10% thiopene solution in EtOH, was hydrogenated at room temperature for 24 hours under a 3 bar pressure, then filtered over celite. The solvent was evaporated till dryness. The residue (1.8 g) was purified by column chromatography over silica gel (15-40 nm) (eluent: DCM/MeOH/$NH_4OH$ 95/5/0.2 to 93/7/0.5). The pure fractions were collected and the solvent was evaporated, yielding 0.7 g (44%) of intermediate 54.

b) Preparation of Intermediate 55

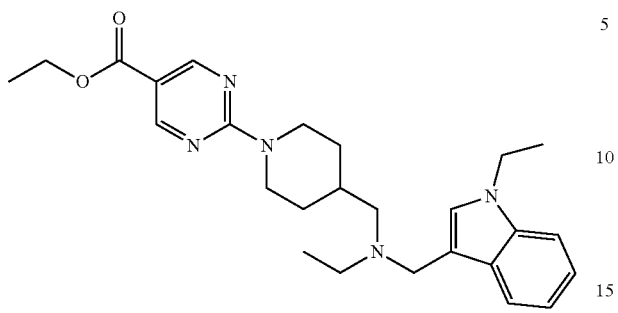

Sodium hydride 60% (0.009 mol) was added at 0° C. to a solution of intermediate 54 (0.0045 mol) in THF (50 ml) under $N_2$ flow. The mixture was stirred at room temperature for 1 hour. A solution of iodo-ethane (0.0062 mol) in THF (10 ml) was added dropwise. The mixture was stirred at room temperature overnight, poured out into water and extracted with EtOAc. The organic layer was separated, dried ($MgSO_4$), filtered, and the solvent was evaporated. The residue (0.6 g) was purified by column chromatography over silica gel (15-40 μm) (eluent: DCM/MeOH/$NH_4OH$ 95/5/0.1).
The pure fractions were collected and the solvent was evaporated, yielding 0.16 g (8%) of intermediate 55.

c) Preparation of Intermediate 56

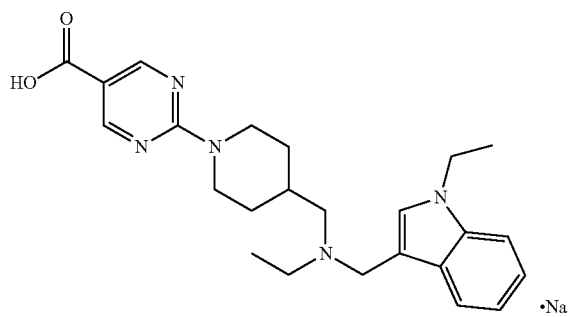

A mixture of intermediate 55 (0.0003 mol) and sodium hydroxide (0.03 g) in EtOH (15 ml) was stirred at 80° C. for 6 hours, then evaporated till dryness, yielding 0.16 g (100%) of intermediate 56.

d) Preparation of Intermediate 57

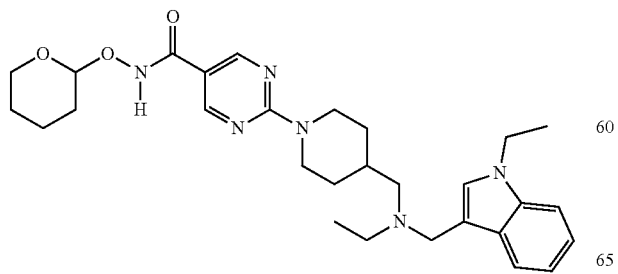

EDC (0.0005 mol) and HOBt (0.0005 mol) were added at room temperature to a mixture of intermediate 56 (0.0003 mol) in DCM (20 ml) and THF (20 ml) under $N_2$ flow. The mixture was stirred for 15 minutes. O-(tetrahydro-2H-pyran-2-yl)-hydroxylamine (0.0007 mol) was added. The mixture was stirred at room temperature for 72 hours, poured out into water and extracted with DCM. The organic layer was separated, dried ($MgSO_4$), filtered, and the solvent was evaporated. The residue (0.3 g) was purified by column chromatography over kromasil (5 μm) (eluent: DCM/MeOH/$NH_4OH$ 93/7/0.35). The pure fractions were collected and the solvent was evaporated, yielding 0.03 g (16%) of intermediate 57.

EXAMPLE A8 a) Preparation of Intermediate 58

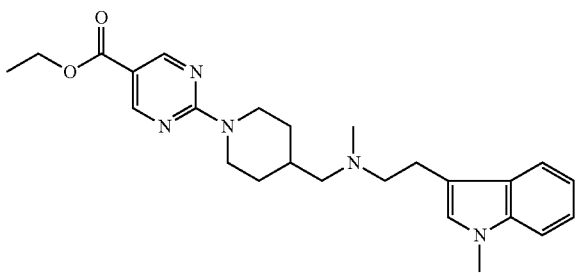 [SMILES: CCOC(=O)c1cnc(N2CCC(CN(C)CCc3cn(C)c4ccccc34)CC2)nc1]

Sodium hydride (0.011 mol) was added at 5° C. to a solution of intermediate 13 (0.0037 mol) in THF (30 ml) under $N_2$ flow. The mixture was stirred for 30 minutes. A solution of iodomethane (0.0081 mol) in THF (10 ml) was added dropwise. The mixture was stirred at 10° C. for 2 hours, then brought to room temperature for 1 hour and 30 minutes, poured out into ice water and extracted with DCM. The organic layer was separated, dried ($MgSO_4$), filtered, and the solvent was evaporated. The residue (1.7 g) was purified by column chromatography over kromasil (15-40 μm) (eluent: DCM/MeOH/$NH_3OH$ 98/2/0.1). Two fractions were collected and the solvent was evaporated, yielding 0.265 g of intermediate 58 and 0.57 g (17%) of intermediate 10.

b) Preparation of Intermediate 59

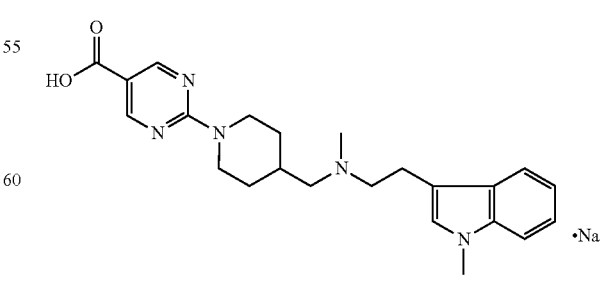

A mixture of intermediate 58 (0.0006 mol) and sodium hydroxide (0.0012 mol) in EtOH (30 ml) was stirred at 80° C.

overnight, then cooled to room temperature and the solvent was evaporated, yielding 0.26 g (100%) of intermediate 59.

c) Preparation of Intermediate 60

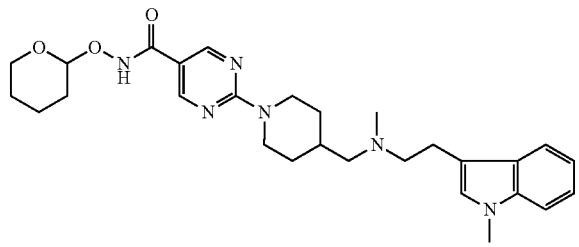 [SMILES: CN(CCc1cn(C)c2ccccc12)CC1CCN(c2ncc(C(=O)NOC3CCCCO3)cn2)CC1]

EDC (0.0009 mol) and HOBt (0.0009 mol) were added at room temperature to a solution of intermediate 59 (0.0006 mol) in THF (30 ml) and DCM (30 ml) under $N_2$ flow. The mixture was stirred at room temperature for 15 minutes. O-(tetrahydro-2H-pyran-2-yl)-hydroxylamine (0.0012 mol) was added. The mixture was stirred at room temperature for 24 hours, poured out into water and extracted with DCM. The organic layer was separated, dried ($MgSO_4$), filtered, and the solvent was evaporated. The residue (0.6 g) was purified by column chromatography over kromasil (5 μm) (eluent: DCM/MeOH/$NH_4OH$ 99/1/0.05 and 94/6/0.3). The pure fractions were collected and the solvent was evaporated, yielding 0.1 g (33%) of intermediate 60.

EXAMPLE A9 a) Preparation of Intermediate 61

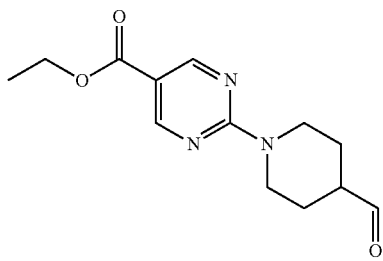 [SMILES: CCOC(=O)c1cnc(N2CCC(C=O)CC2)nc1]

DMSO (0.127 mol) was added at −78° C. to a solution of ethanedioyl dichloride (0.061 mol) in DCM (110 ml) under $N_2$ flow. The mixture was stirred for 15 minutes. A solution of intermediate 8 (0.051 mol) in DCM (200 ml) was added. The mixture was stirred at −78° C. for 1 hour and 30 minutes. Triethylamine (0.26 mol) was added dropwise. The mixture was stirred at −78° C. for 15 minutes, then brought to room temperature for 2 hours and 30 minutes. Water was added. The mixture was extracted with DCM. The organic layer was separated, dried ($MgSO_4$), filtered, and the solvent was evaporated. The residue (14 g) was purified by column chromatography over silica gel (20-45 μm) (eluent: cyclohexane/EtOAc 70/30). The pure fractions were collected and the solvent was evaporated, yielding 7.6 g (57%) of intermediate 61.

b) Preparation of Intermediate 62

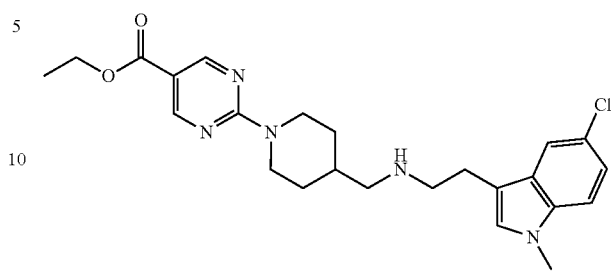

Sodiumcyanoborohydride (0.049 mol) and acetic acid (0.034 ml) were added at room temperature to a solution of 5-chloro-1-methyl-1H-Indole-3-ethanamine (0.031 mol) and intermediate 61 (0.034 mol) in MeOH (700 ml) under $N_2$ flow. The mixture was stirred at room temperature for 24 hours, poured out into potassium carbonate 10% and extracted with DCM. The organic layer was separated, dried ($MgSO_4$), filtered and the solvent was evaporated. The residue (14.8 g) was purified by column chromatography over silica gel (20-45 μm) (eluent: DCM/MeOH/$NH_4OH$ 95/5/0.2). The pure fractions were collected and the solvent was evaporated, yielding 4.52 g (32%) of intermediate 62.

c) Preparation of Intermediate 63

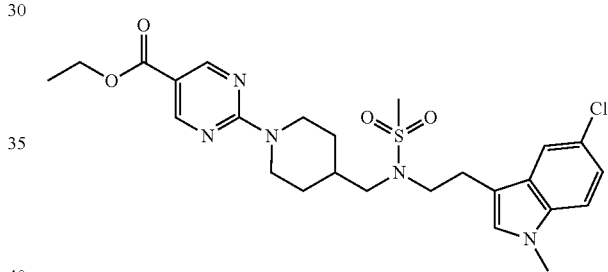

Methanesulfonyl chloride (0.0049 mol) was added at 5° C. to a solution of intermediate 62 (0.004 mol) and triethylamine (0.008 mol) in DCM (150 ml) under $N_2$ flow. The mixture was stirred at room temperature for 24 hours, poured out into ice water and extracted with DCM. The organic layer was separated, dried ($MgSO_4$), filtered and the solvent was evaporated. The residue (2.39 g) was taken up in DIPE. The precipitate was filtered off and dried, yielding 1.78 g (84%) of intermediate 63, melting point 162° C.

d) Preparation of Intermediate 64

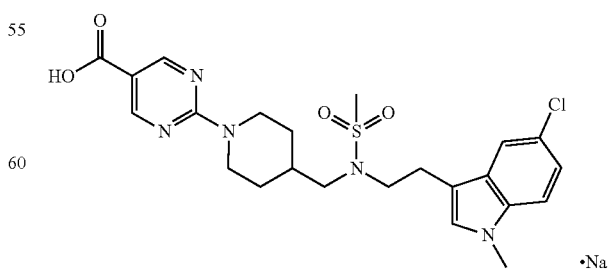

A mixture of intermediate 63 (0.0032 mol) and sodium hydroxide (0.0128 mol) in EtOH (150 ml) was stirred and refluxed for 5 hours, then cooled to room temperature and taken up in diethyl ether. The precipitate was filtered off and dried, yielding 1.57 g (99%) of intermediate 64, melting point>260° C.

e) Preparation of Intermediate 65

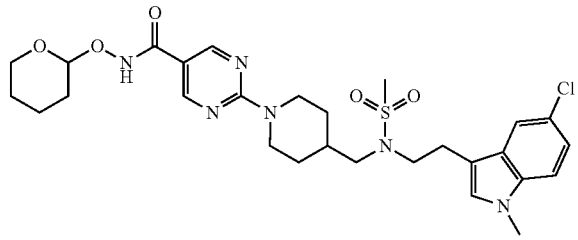 [SMILES: Cn1cc(CCN(CC2CCN(c3ncc(C(=O)NOC4CCCCO4)cn3)CC2)S(C)(=O)=O)c2cc(Cl)ccc21]

EDC (0.0064 mol) and HOBt (0.0064 mol) were added at room temperature to a solution of intermediate 64 (0.0032 mol) in THF (160 ml) and DCM (160 ml) under $N_2$ flow. The mixture was stirred at room temperature for 30 minutes. O-(tetrahydro-2H-pyran-2-yl)-hydroxylamine (0.0064 mol) was added. The mixture was stirred at room temperature for 3 days, poured out into water and extracted with DCM. The organic layer was separated, dried ($MgSO_4$), filtered and the solvent was evaporated. The residue (2.77 g) was purified by column chromatography over silica gel (15-40 μm) (eluent: DCM/MeOH/$NH_4$OH 97/3/0.1). The pure fractions were collected and the solvent was evaporated. The residue (0.385 g) was crystallized from $CH_3CN$/diethyl ether. The precipitate was filtered off and dried, yielding 0.084 g of intermediate 65, melting point 179° C.

EXAMPLE A10 a) Preparation of Intermediate 66

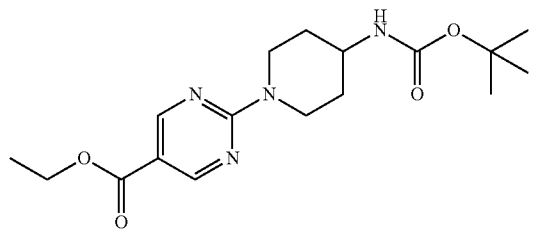 [SMILES: CCOC(=O)c1cnc(N2CCC(NC(=O)OC(C)(C)C)CC2)nc1]

A solution of 2-(methylsulfonyl)-5-pyrimidinecarboxylic acid, ethyl ester (0.094 mol) in acetonitrile (240 ml) was added at room temperature to a solution of 4-piperidinylcarbamic acid, 1,1-dimethylethyl ester (0.078 mol) and potassium carbonate (0.156 mol) in acetonitrile (120 ml) under $N_2$ flow. The mixture was stirred at room temperature overnight, poured out into ice water and extracted with EtOAc. The organic layer was washed with water, dried ($MgSO_4$), filtered, and the solvent was evaporated. The residue was crystallized from diethyl ether. The precipitate was filtered off and dried, yielding 14.4 g (53%) of intermediate 66, melting point 160° C.

b) Preparation of Intermediate 67

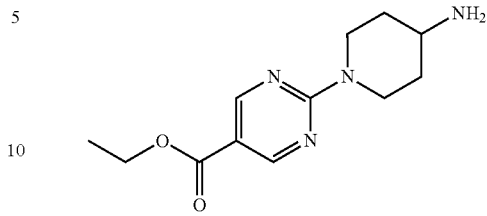

TFA (20 ml) was added at room temperature to a solution of intermediate 66 (0.0225 mol) in DCM (110 ml). The mixture was stirred at room temperature for 15 hours, poured out into water and basified with potassium carbonate. The mixture was extracted with DCM. The organic layer was separated, dried (MgSO4), filtered, and the solvent was evaporated, yielding 5.5 g (98%) of intermediate 67.

EXAMPLE A11 a) Preparation of Intermediate 68

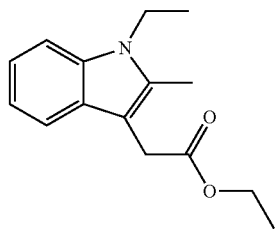 [SMILES: CCOC(=O)Cc1c(C)n(CC)c2ccccc12]

Sodium hydride 60% in oil (0.0069 mol) was added at 0° C. to a solution of 2-methyl-1H-indole-3-acetic acid, ethyl ester (0.0046 mol) in THF (10 ml) under $N_2$ flow. The mixture was stirred at room temperature for 1 hour. Iodo-ethane (0.006 mol) was added. The mixture was stirred at room temperature for 18 hours and poured out into EtOAc and saturated NaCl. The organic layer was separated, dried ($MgSO_4$), filtered and the solvent was evaporated till dryness. The residue (1.1 g) was purified by column chromatography over silica gel (15-40 μm) (eluent: cyclohexane/EtOAc 80/20). The pure fractions were collected and the solvent was evaporated, yielding 0.73 g (65%) of intermediate 68.

b) Preparation of Intermediate 69

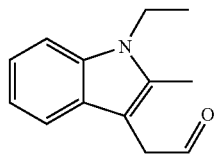

A solution of diisobuytlaluminium hydride in toluene (0.0045 mol) was added dropwise at −78° C. to a solution of intermediate 68 (0.003 mol) in DCM (15 ml) and 1,2-dimethoxyethane (15 ml) (molecular sieves: 3 angstrom) under N₂ flow. The mixture was stirred at −78° C. for 3 hours, then quenched with HCl 3N and extracted with DCM. The organic layer was washed with water, dried (MgSO₄), filtered and the solvent was evaporated till dryness, yielding 0.7 g (>100%) of intermediate 69.

c) Preparation of Intermediate 70

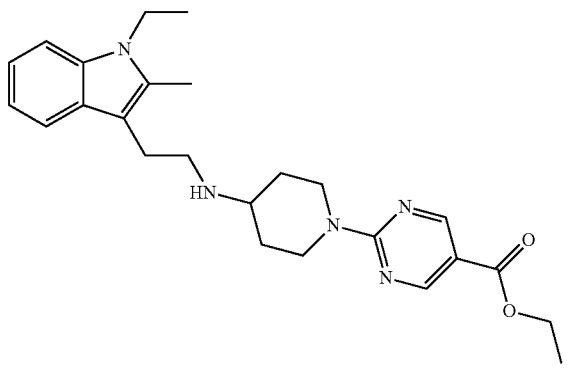 [SMILES: CCOC(=O)c1cnc(N2CCC(NCCc3c(C)n(CC)c4ccccc34)CC2)nc1]

Titanium (IV) ethoxide (0.0023 mol) was added to a mixture of intermediate 67 (0.0021 mol) and intermediate 69 (0.0021 mol) in 1,2-dichloro-ethane (25 ml). The mixture was stirred at room temperature for 30 minutes. Tris(acetato-α-O)hydro-borate(1-), sodium (0.0023 mol) was added portionwise. The mixture was stirred at room temperature for 18 hours, then quenched with NaHCO₃ and extracted with DCM. The organic layer was separated, dried (MgSO₄), filtered and the solvent was evaporated till dryness. The residue (1.2 g) was purified by column chromatography over silica gel (Sum) (eluent: DCM/MeOH/NH₄OH 95/5/0.1). The pure fractions were collected and the solvent was evaporated, yielding 0.2 g (21%) of intermediate 70.

d) Preparation of Intermediate 71

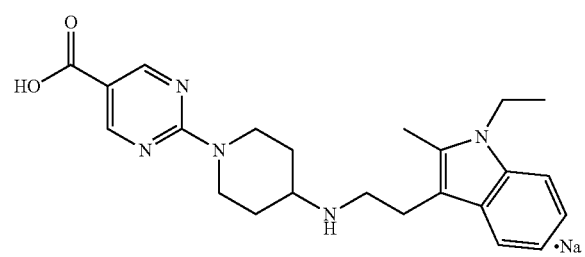

A mixture of intermediate 70 (0.0004 mol) and sodium hydroxide (0.0009 mol) in EtOH (30 ml) was stirred at 60° C. overnight, then cooled to room temperature and evaporated, yielding 0.2 g (100%) of intermediate 71.

e) Preparation of Intermediate 72

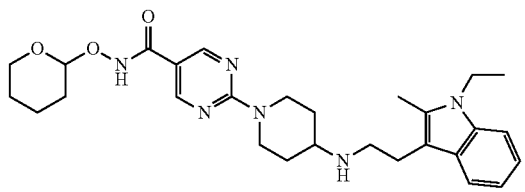 [SMILES: CCn1c(C)c(CCNC2CCN(c3ncc(C(=O)NOC4CCCCO4)cn3)CC2)c2ccccc21]

EDC (0.0007 mol) and HOBt (0.1 g) were added at room temperature to a solution of intermediate 71 (0.0004 mol) and triethylamine (0.0009 mol) in DCM/THF (40 ml) under N₂ flow. The mixture was stirred at room temperature for 15 minutes. O-(tetrahydro-2H-pyran-2-yl)-hydroxylamine (0.0009 mol) was added. The mixture was stirred at room temperature for 72 hours, poured out into water and extracted with DCM. The organic layer was separated, dried (MgSO₄), filtered and the solvent was evaporated. The residue (0.4 g) was purified by column chromatography over kromasil (5 μm)(eluent: DCM/MeOH/NH₄OH 98/2/0.1 to 90/10/1). The pure fractions were collected and the solvent was evaporated, yielding 0.087 g (37%) of intermediate 72.

EXAMPLE A12 a) Preparation of Intermediate 73

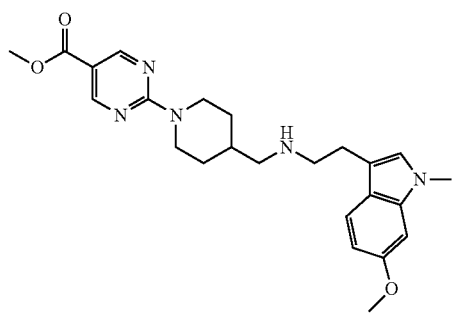

Intermediate 50 (0.0046 mol) was added at 5° C. to a solution of 6-methoxy-1-methyl-1H-Indole-3-ethanamine (0.0046 mol) in MeOH (100 ml) under N₂ flow. The mixture was stirred for 30 minutes. Sodiumcyanoborohydride (0.0068 mol) then acetic acid (0.0046 mol) were added portionwise. The mixture was stirred at room temperature for 48 hours, poured out into potassium carbonate 10% and extracted with DCM. The organic layer was separated, dried (MgSO₄), filtered, and the solvent was evaporated. The residue (4 g) was purified by column chromatography over silica gel (15-40 μm)) (eluent: DCM/MeOH/NH₄OH 96/4/0.2). The pure fractions were collected and the solvent was evaporated. A part (0.7 g) of the residue (2.2 g) was crystallized from acetonitrile. The precipitate was filtered off and dried, yielding 0.43 g (61%) of intermediate 73, melting point 122° C.

b) Preparation of Intermediate 74

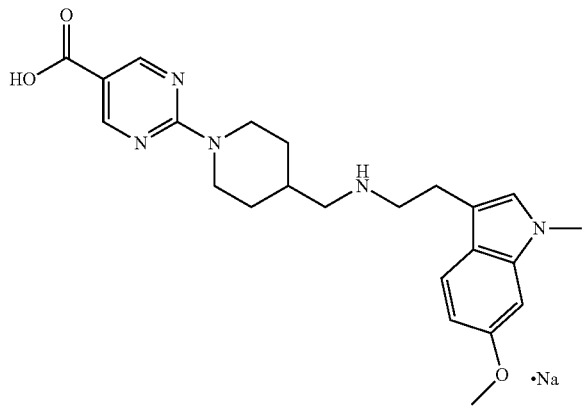

A mixture of intermediate 73 (0.0015 mol) and sodium hydroxide (0.006 mol) in EtOH (90 ml) was stirred and refluxed for 8 hours, then evaporated till dryness, yielding intermediate 74.

c) Preparation of Intermediate 75

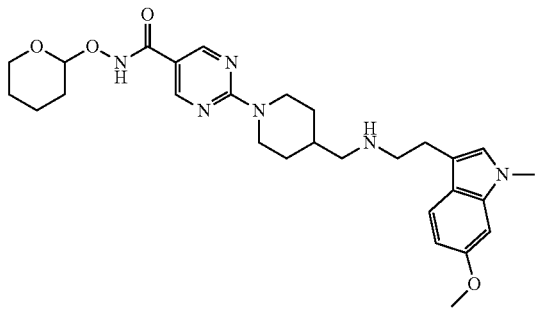 [SMILES: COc1ccc2c(CCNCC3CCN(c4ncc(C(=O)NOC5CCCCO5)cn4)CC3)cn(C)c2c1]

HOBt (0.003 mol) then EDC (0.003 mol) were added at room temperature to a solution of intermediate 74 (0.0015 mol) and O-(tetrahydro-2H-pyran-2-yl)-hydroxylamine (0.003 mol) in THF/DCM (200 ml) under $N_2$ flow. The mixture was stirred at room temperature for 48 hours, poured out into water and extracted with DCM. The organic layer was separated, dried (MgSO$_4$), filtered, and the solvent was evaporated. The residue (1.1 g) was purified by column chromatography over silica gel (10 μm) (eluent: DCM/MeOH/ NH$_4$OH 95/5/0.5). The pure fractions were collected and the solvent was evaporated. The residue (0.24 g) was purified by column chromatography over silica gel (10 μm) (eluent: DCM/MeOH/NH$_4$OH 95/5/0.5). The pure fractions were collected and the solvent was evaporated, yielding 0.17 g (21%) of intermediate 75.

EXAMPLE A13 a) Preparation of Intermediate 76

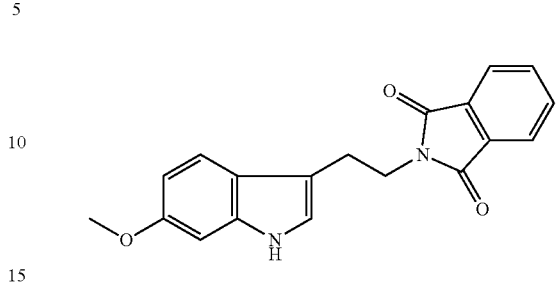

A mixture of 6-methoxy-1H-indole-3-ethanamine (0.053 mol) and 1,3-isobenzofurandione (0.058 mol) in toluene (130 ml) was stirred and refluxed for 48 hours, then filtered. The filtrate was evaporated, yielding 5.4 g (32%) of intermediate 76.

b) Preparation of Intermediate 77

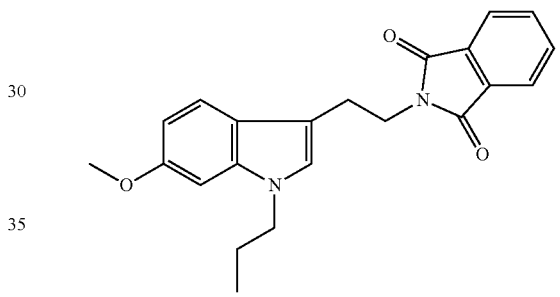

A solution of intermediate 76 (0.017 mol) in DMF (19 ml) was added dropwise at room temperature to a suspension of sodium hydride (0.034 mol) in DMF (11 ml) under $N_2$ flow. The mixture was stirred at room temperature for 1 hour and 30 minutes. 1-iodo-propane (0.034 mol) was added. The mixture was stirred at room temperature for 1 hour and 15 minutes. Saturated NaCl was added. The mixture was extracted with EtOAc. The organic layer was washed with water, dried (MgSO$_4$), filtered, and the solvent was evaporated, yielding 4.9 g of intermediate 77. This product was used directly in the next reaction step.

c) Preparation of Intermediate 78

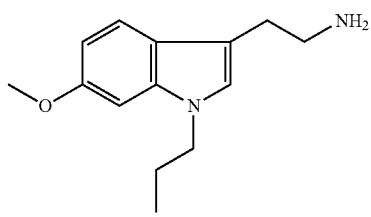 [SMILES: CCCn1cc(CCN)c2ccc(OC)cc21]

A mixture of intermediate 77 (0.068 mol) and hydrazine, monohydrate (0.068 mol) in EtOH (60 ml) was stirred and refluxed for 1 hour, poured out into water and extracted with DCM. The organic layer was separated, dried (MgSO$_4$), filtered, and the solvent was evaporated, yielding 3.53 g of intermediate 78. This product was used directly in the next reaction step.

d) Preparation of Intermediate 79

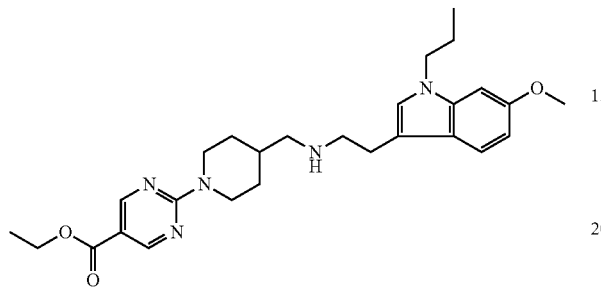

Sodiumcyanoborohydride (0.024 mol) and acetic acid (0.0167 mol) were added at room temperature to a solution of intermediate 61 (0.0167 mol) and intermediate 78 (0.015 mol) in MeOH (380 ml) under N$_2$ flow. The mixture was stirred for 30 minutes, poured out into potassium carbonate 10% and extracted with DCM. The organic layer was separated, dried (MgSO$_4$), filtered, and the solvent was evaporated. The residue (8.84 g) was purified by column chromatography over silica gel (15-40 μm) (eluent: DCM/MeOH/NH$_4$OH 96/4/0.2). The pure fractions were collected and the solvent was evaporated, yielding 2.85 g (40%) of intermediate 79.

e) Preparation of Intermediate 80

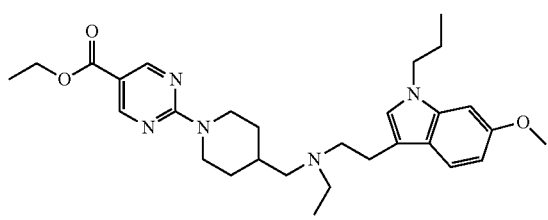 [SMILES: CCCn1cc(CCN(CC)CC2CCN(c3ncc(C(=O)OCC)cn3)CC2)c2ccc(OC)cc21]

A mixture of intermediate 79 (0.0028 mol), iodo-ethane (0.0056 mol) and triethylamine (0.0085 mol) in DMF (60 ml) was stirred at 50° C. for 7 hours, poured out into ice water and extracted with EtOAc. The organic layer was washed with water, dried (MgSO$_4$), filtered and the solvent was evaporated. The residue (1.8 g) was purified by column chromatography over kromasil (5 μm) (eluent: DCM/MeOH 100/0 to 95/5). The pure fractions were collected and the solvent was evaporated, yielding 1.1 g (78%) of intermediate 80.

f) Preparation of Intermediate 81

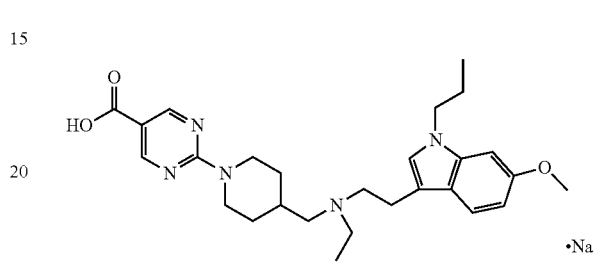

A mixture of intermediate 80 (0.0022 mol) and sodium hydroxide (0.0088 mol) in EtOH (100 ml) was stirred and refluxed for 6 hours, then stirred at room temperature overnight and evaporated till dryness. The residue was taken up in diethyl ether. The precipitate was filtered off and dried, yielding 0.965 g (88%) of intermediate 81, melting point>260° C.

g) Preparation of Intermediate 82

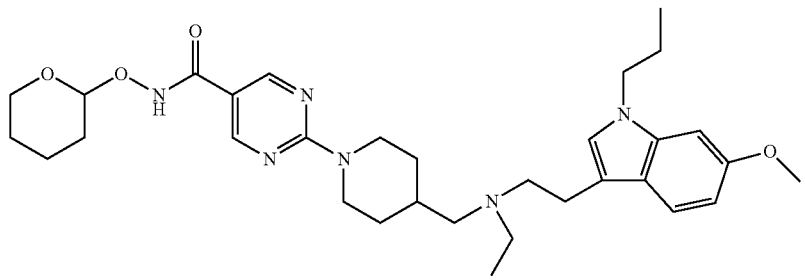 [SMILES: CCCn1cc(CCN(CC)CC2CCN(c3ncc(C(=O)NOC4CCCCO4)cn3)CC2)c2ccc(OC)cc21]

EDC (0.0038 mol) and HOBt (0.0038 mol) were added at room temperature to a solution of intermediate 81 (0.0019 mol) in THF (100 ml) and DCM (100 ml) under N$_2$ flow. The mixture was stirred at room temperature for 30 minutes. O-(tetrahydro-2H-pyran-2-yl)-hydroxylamine (0.0038 mol) was added. The mixture was stirred at room temperature for 48 hours, poured out into water and extracted with DCM. The organic layer was separated, dried (MgSO$_4$), filtered and the solvent was evaporated. The residue (1.2 g) was purified by column chromatography over kromasil (5 μm) (eluent: DCM/MeOH/NH$_4$OH 99/1/0.05 to 93/7/0.35). The pure fractions were collected and the solvent was evaporated, yielding 0.114 g of intermediate 82.

EXAMPLE A14 a) Preparation of Intermediate 83

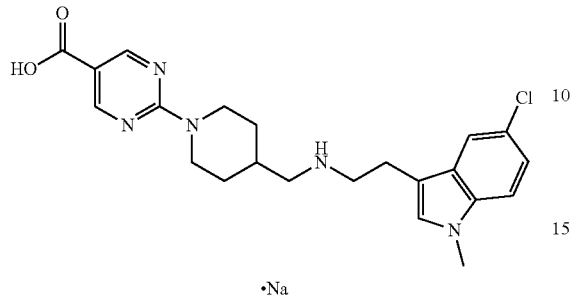

·Na

A mixture of intermediate 62 (0.0034 mol) and sodium hydroxide (0.0134 mol) in EtOH (150 ml) was stirred at 80° C. for 3 hours, then cooled to room temperature and evaporated till dryness. The residue was taken up in diethyl ether. The precipitate was filtered off and dried, yielding 1.18 g (78%) of intermediate 83, melting point>260° C.

b) Preparation of Intermediate 84

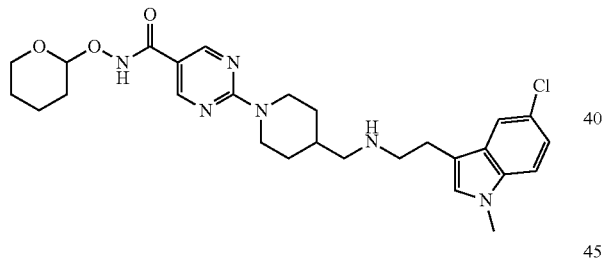

EDC (0.0052 mol) and HOBt (0.0052 mol) were added at room temperature to a solution of intermediate 83 (0.0026 mol) in THF (120 ml) and DCM (120 ml) under $N_2$ flow. The mixture was stirred at room temperature for 30 minutes. O-(tetrahydro-2H-pyran-2-yl)-hydroxylamine (0.0052 mol) was added. The mixture was stirred at room temperature for 6 days, poured out into ice water and extracted with DCM. The organic layer was separated, dried ($MgSO_4$), filtered and the solvent was evaporated. The residue (2 g) was purified by column chromatography over silica gel (15-40 μm) (eluent: DCM/MeOH/$NH_4OH$ 96/4/0.5). The pure fractions were collected and the solvent was evaporated. The residue (0.75 g, 55%) was purified by column chromatography over kromasil (10 μm) (eluent: DCM/MeOH/$NH_4OH$ 96/4/0.5). The pure fractions were collected and the solvent was evaporated, yielding 0.625 g of intermediate 84. This product was used directly in the next reaction step.

EXAMPLE A15

Preparation of Intermediate 85

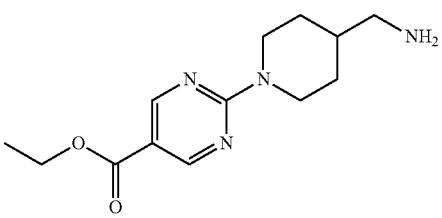 [SMILES: CCOC(=O)c1cnc(N2CCC(CN)CC2)nc1]

4-Piperidinemethanamine (0.65 mol) and potassium carbonate (96 g) were stirred in acetonitrile (1000 ml) and then a solution of 2-(methylsulfonyl)-5-pyrimidinecarboxylic acid, ethyl ester (0.37 mol) in acetonitrile (500 ml) was added dropwise at room temperature over 1 hour. The reaction mixture was stirred overnight at room temperature and the solvent was evaporated. The residue was stirred in water and the mixture was extracted with DCM (2×500 ml). The organic layer was separated, washed with water, dried ($MgSO_4$), filtered off and the solvent was evaporated. The residue was purified by column chromatography over silica gel (eluent 1: EtOAc/Hexane 1/1; eluent 2: MeOH+small amount of $NH_4OH$). The product fractions were collected, stirred with potassium carbonate slurry and the mixture was extracted with DCM. The organic layer was separated, dried ($MgSO_4$), filtered off and the solvent was evaporated, yielding 31 g (32%) of intermediate 85.

EXAMPLE A16 a) Preparation of Intermediate 86

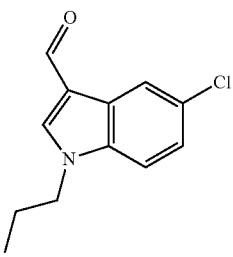

Sodium hydride (0.0095 mol) was added at 5° C. to a solution of 5-chloro-1H-indole-3-carboxaldehyde (0.0056 mol) in THF (52 ml) under $N_2$ flow. The mixture was stirred at 0° C. for 1 hour. 1-Iodo-propane (0.0067 mol) was added. The mixture was stirred at room temperature for 2 days, poured out into water and extracted with EtOAc. The organic layer was separated, dried ($MgSO_4$), filtered, and the solvent was evaporated, yielding 1.5 g of intermediate 86. This product was used directly in the next reaction step.

b) Preparation of Intermediate 87

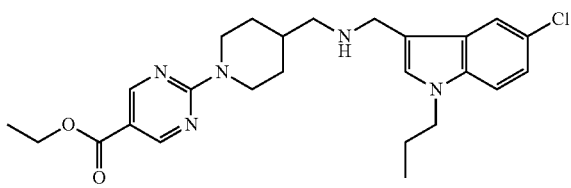 [SMILES: CCCn1cc(CNCC2CCN(c3ncc(C(=O)OCC)cn3)CC2)c2cc(Cl)ccc21]

Sodiumcyanoborohydride (0.0068 mol) and acetic acid (0.0046 mol) were added at room temperature to a solution of intermediate 85 (0.0042 mol) and intermediate 86 (0.0051 mol) in MeOH (120 ml) under $N_2$ flow. The mixture was stirred and refluxed for 2 days, then cooled to room temperature, poured out into potassium carbonate 10% and extracted with DCM. The organic layer was separated, dried ($MgSO_4$), filtered, and the solvent was evaporated. The residue (2.42 g) was purified by column chromatography over silica gel (15-40 μm) (eluent: DCM/MeOH/$NH_4OH$ 95/5/0.2).

The pure fractions were collected and the solvent was evaporated, yielding 1.2 g (60%) of intermediate 87.

c) Preparation of Intermediate 88

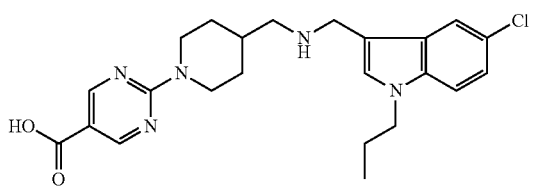

·Na

A mixture of intermediate 87 (0.0025 mol) and sodium hydroxide (0.01 mol) in EtOH (120 ml) was stirred and refluxed for 4 hours, then evaporated till dryness. The residue was taken up in diethyl ether. The precipitate was filtered off and dried, yielding 0.845 g (72%) of intermediate 88, melting point>260° C.

d) Preparation of Intermediate 89

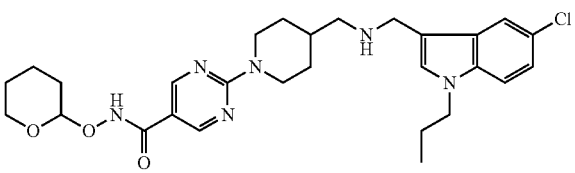 [SMILES: CCCn1cc(CNCC2CCN(c3ncc(C(=O)NOC4CCCCO4)cn3)CC2)c2cc(Cl)ccc21]

EDC (0.0036 mol) and HOBt (0.0036 mol) were added at room temperature to a solution of intermediate 88 (0.0018 mol) in THF (90 ml) and DCM (90 ml) under $N_2$ flow. The mixture was stirred for 30 minutes. O-(tetrahydro-2H-pyran-2-yl)-hydroxylamine (0.0036 mol) was added. The mixture was stirred at room temperature for 3 days, poured out into ice water and extracted with DCM. The organic layer was separated, dried ($MgSO_4$), filtered, and the solvent was evaporated. The residue (1.3 g) was purified by column chromatography over silica gel (15-40 μm) (eluent: DCM/MeOH/$NH_4OH$ 92/8/0.5). The pure fractions were collected and the solvent was evaporated, yielding 0.54 g (56%) of intermediate 89.

EXAMPLE A17 a) Preparation of Intermediate 90

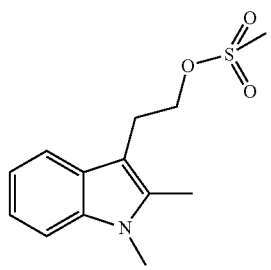 [SMILES: Cc1c(CCOS(C)(=O)=O)c2ccccc2n1C]

Methanesulfonyl chloride (0.004 mol) was added at 10° C. to a solution of 1,2-dimethyl-1H-indole-3-ethanol (0.0026 mol) and triethyl amine (0.008 mol) in DCM (10 ml) under $N_2$ flow. The mixture was stirred at 10° C. for 4 hours. The solvent was evaporated till dryness, yielding intermediate 90. This product was used directly in the next reaction step.

b) Preparation of Intermediate 91

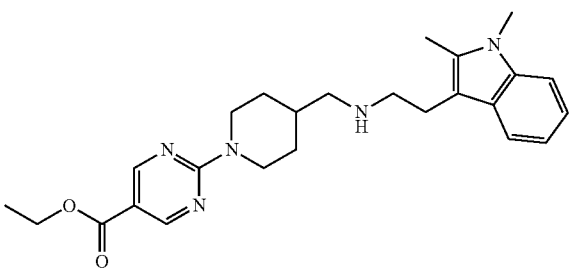 [SMILES: CCOC(=O)c1cnc(N2CCC(CNCCc3c(C)n(C)c4ccccc34)CC2)nc1]

A mixture of intermediate 85 (0.0054 mol), intermediate 90 (0.0075 mol) and potassium carbonate (0.021 mol) in acetonitrile (150 ml) was stirred and refluxed for 2 days, then cooled to room temperature, poured out into ice water and extracted with EtOAc. The organic layer was separated, dried ($MgSO_4$), filtered, and the solvent was evaporated. The residue (1.88 g) was purified by column chromatography over silica gel (15-40 µm) (eluent: DCM/MeOH/NH$_4$OH 97/3/0.1). The pure fractions were collected and the solvent was evaporated, yielding 0.15 g (7%) of intermediate 91.

c) Preparation of Intermediate 92

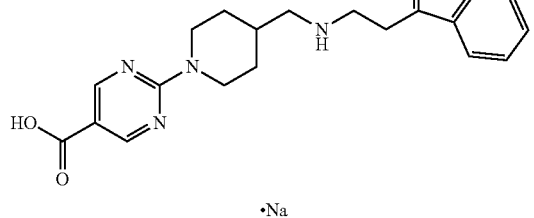

•Na

A mixture of intermediate 91 (0.0003 mol) in sodium hydroxide (0.0014 mol) and EtOH (20 ml) was stirred and refluxed for one day, then cooled to room temperature and evaporated till dryness. The residue was taken up in diethyl ether. The precipitate was filtered off and dried, yielding 0.12 g (82%) of intermediate 92, melting point> d) Preparation of Intermediate 93

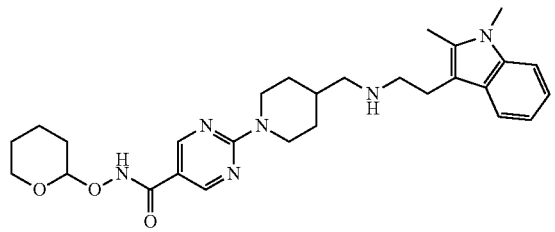 [SMILES: Cc1c(CCNCC2CCN(c3ncc(C(=O)NOC4CCCCO4)cn3)CC2)c2ccccc2n1C]

EDC (0.0005 mol) and HOBt (0.0005 mol) were added at room temperature to a solution of intermediate 92 (0.0002 mol) in THF (15 ml) and DCM (15 ml). The mixture was stirred for 15 minutes. O-(tetrahydro-2H-pyran-2-yl)-hydroxylamine (0.0005 mol) was added. The mixture was stirred at room temperature for 4 days, poured out into ice water and extracted with DCM. The organic layer was separated, dried (MgSO$_4$), filtered, and the solvent was evaporated. The residue (0.14 g) was purified by column chromatography over silica gel (10 µm) (eluent: DCM/MeOH/NH$_4$OH 95/5/0.3). The pure fractions were collected and the solvent was evaporated, yielding 0.035 g (25%) of intermediate 93.

Table F-1 lists the intermediates that were prepared according to one of the above Examples.

TABLE F-1

(intermediates)

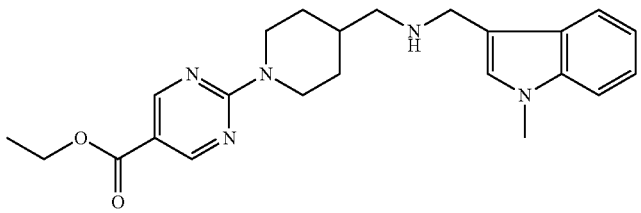 [SMILES: CCOC(=O)c1cnc(N2CCC(CNCc3cn(C)c4ccccc34)CC2)nc1]

Interm. 1; Ex. [A1]

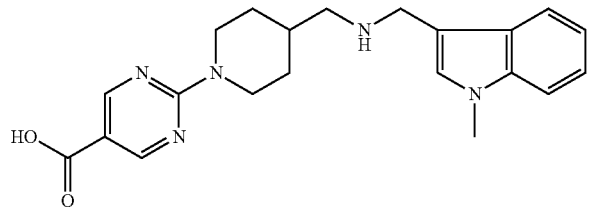 [SMILES: Cn1cc(CNCC2CCN(c3ncc(C(=O)O)cn3)CC2)c2ccccc21]

Interm. 2; Ex. [A1]; mp. >260° C.

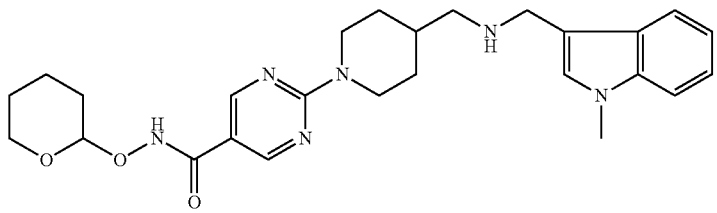 [SMILES: Cn1cc(CNCC2CCN(c3ncc(C(=O)NOC4CCCCO4)cn3)CC2)c2ccccc21]

Interm. 3; Ex. [A1]; mp. 70° C.

TABLE F-1-continued
(intermediates)
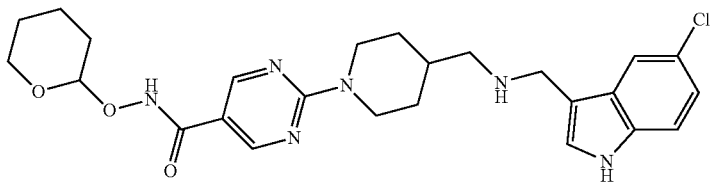 [SMILES: O=C(NOC1CCCCO1)c1cnc(N2CCC(CNCc3c[nH]c4ccc(Cl)cc34)CC2)nc1]
Interm. 7; Ex. [A2]
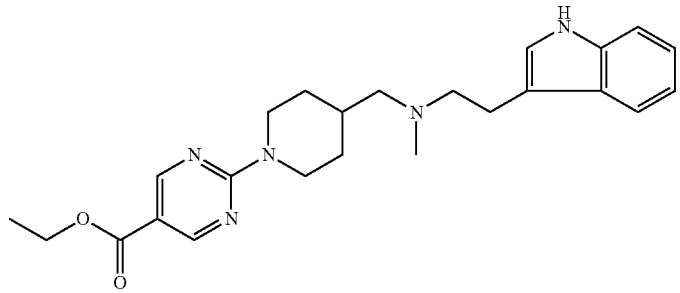 [SMILES: CCOC(=O)c1cnc(N2CCC(CN(C)CCc3c[nH]c4ccccc34)CC2)nc1]
Interm. 10; Ex. [A3]
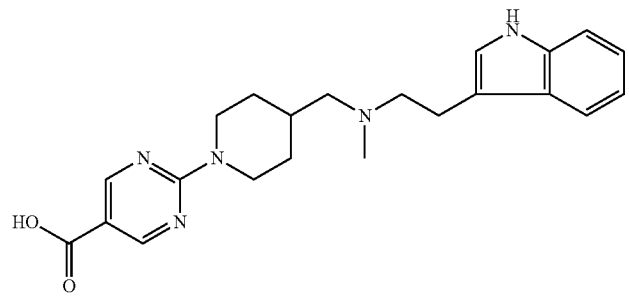 [SMILES: CN(CCc1c[nH]c2ccccc12)CC1CCN(c2ncc(C(=O)O)cn2)CC1]
•Na; Interm. 11; Ex. [A3]; mp. >260° C.
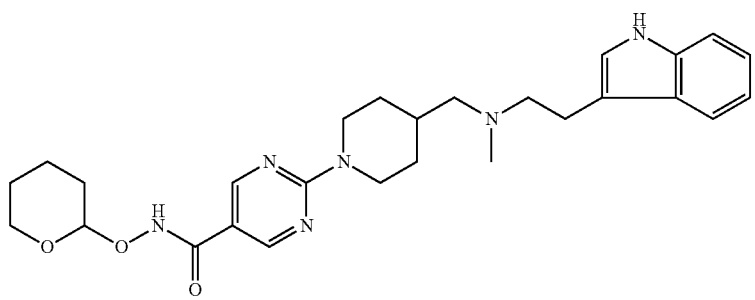 [SMILES: CN(CCc1c[nH]c2ccccc12)CC1CCN(c2ncc(C(=O)NOC3CCCCO3)cn2)CC1]
Interm.12; Ex. [A3]; mp. 154° C.
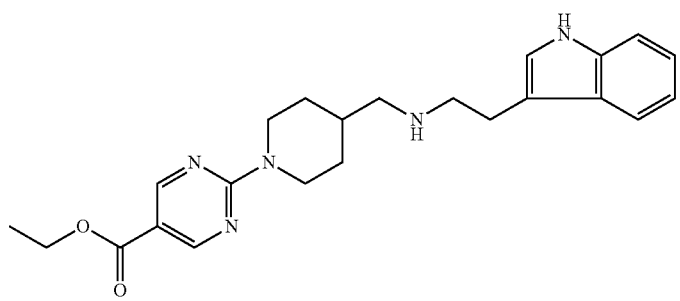 [SMILES: CCOC(=O)c1cnc(N2CCC(CNCCc3c[nH]c4ccccc34)CC2)nc1]
Interm. 13; Ex. [A4]; mp. 238° C.

TABLE F-1-continued
(intermediates)
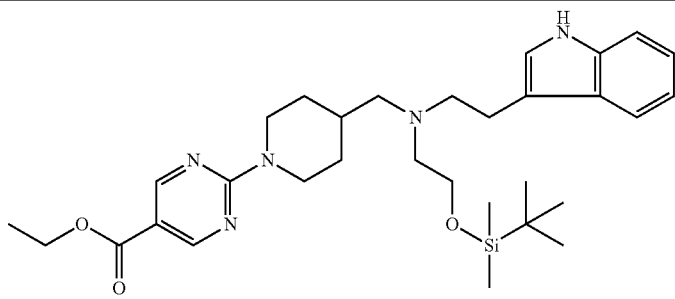
Interm. 14; Ex. [A4]
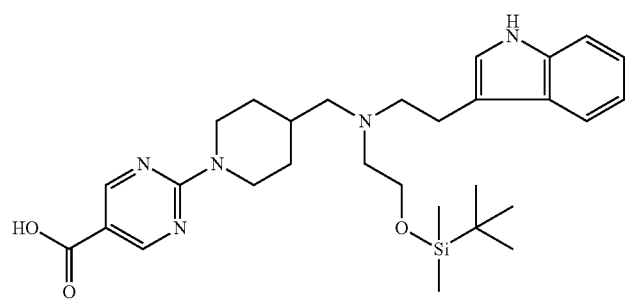 [SMILES: CC(C)(C)[Si](C)(C)OCCN(CCc1c[nH]c2ccccc12)CC1CCN(c2ncc(C(=O)O)cn2)CC1]
•Na; Interm. 15; Ex. [A4]
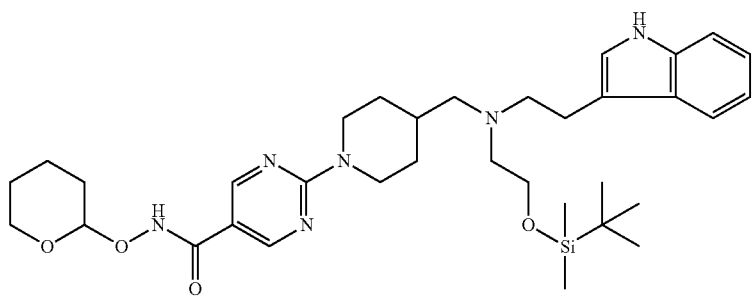 [SMILES: CC(C)(C)[Si](C)(C)OCCN(CCc1c[nH]c2ccccc12)CC1CCN(c2ncc(C(=O)NOC3CCCCO3)cn2)CC1]
•Na; Interm. 16; Ex. [A4]
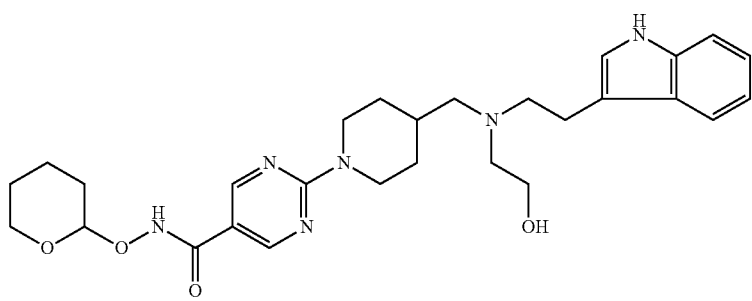 [SMILES: O=C(NOC1CCCCO1)c1cnc(N2CCC(CN(CCO)CCc3c[nH]c4ccccc34)CC2)nc1]
Interm. 17; Ex. [A4]
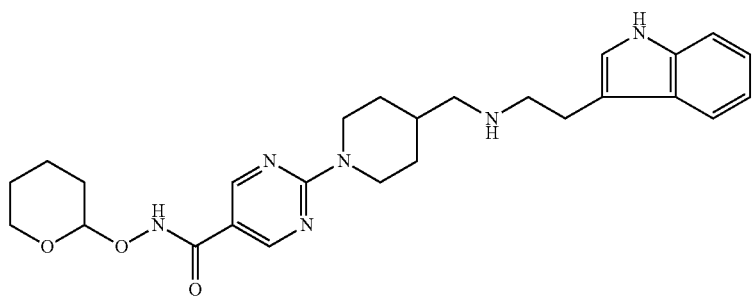 [SMILES: O=C(NOC1CCCCO1)c1cnc(N2CCC(CNCCc3c[nH]c4ccccc34)CC2)nc1]
Interm. 18; Ex. [A1]; mp. 109° C.

TABLE F-1-continued
(intermediates)
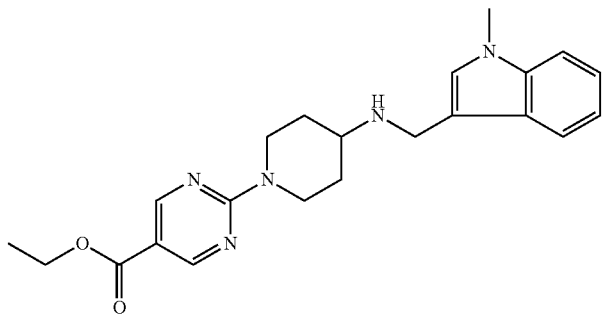 [SMILES: CCOC(=O)c1cnc(N2CCC(NCc3cn(C)c4ccccc34)CC2)nc1]
Interm. 19; Ex. [A1]
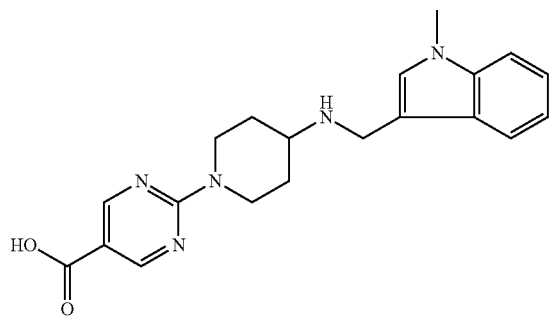 [SMILES: Cn1cc(CNC2CCN(c3ncc(C(=O)O)cn3)CC2)c2ccccc21]
•Na; Interm. 20; Ex. [A1]
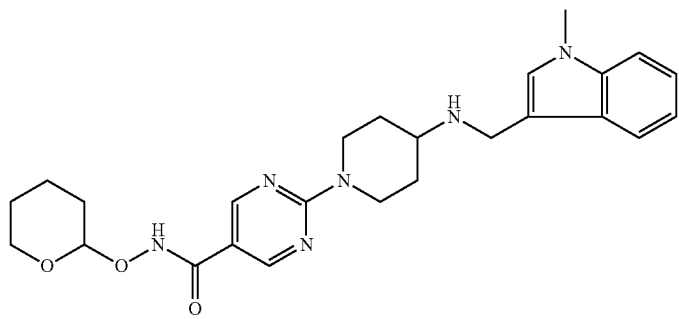 [SMILES: Cn1cc(CNC2CCN(c3ncc(C(=O)NOC4CCCCO4)cn3)CC2)c2ccccc21]
Interm. 21; Ex. [A1]; mp. 70° C.
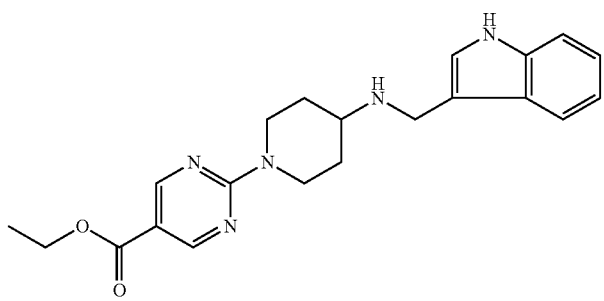 [SMILES: CCOC(=O)c1cnc(N2CCC(NCc3c[nH]c4ccccc34)CC2)nc1]
Interm. 22; Ex. [A1]; mp. 159° C.

TABLE F-1-continued
(intermediates)
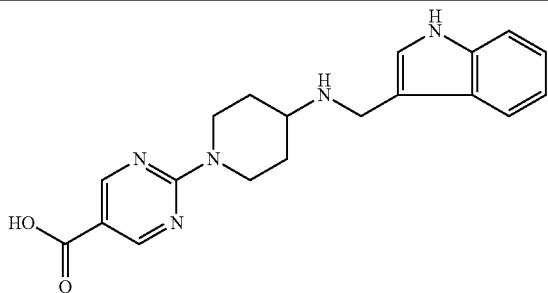
•Na; Interm. 23; Ex. [A1]
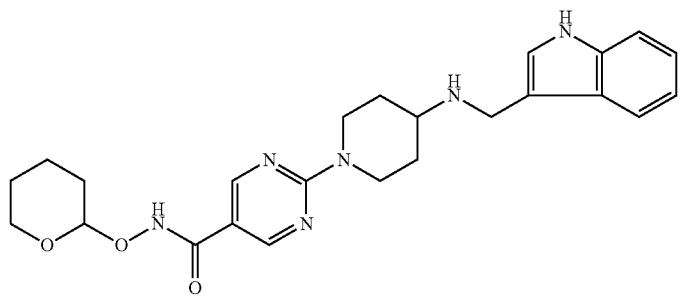 [SMILES: O=C(NOC1CCCCO1)c1cnc(N2CCC(NCc3c[nH]c4ccccc34)CC2)nc1]
Interm. 24; Ex. [A1]; mp.100° C.
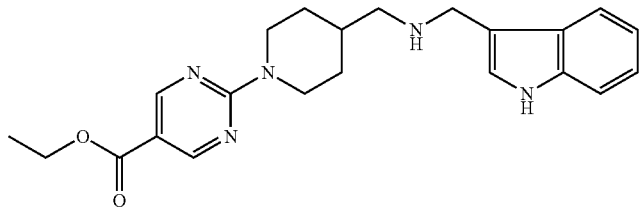 [SMILES: CCOC(=O)c1cnc(N2CCC(CNCc3c[nH]c4ccccc34)CC2)nc1]
Interm. 25; Ex. [A1]; mp. 120° C.
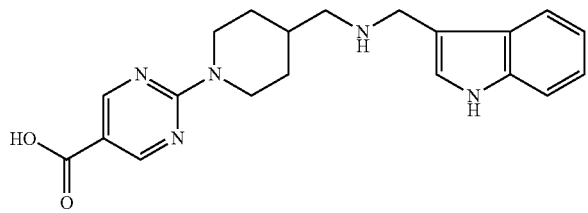 [SMILES: O=C(O)c1cnc(N2CCC(CNCc3c[nH]c4ccccc34)CC2)nc1]
Interm. 26; Ex. [A1]
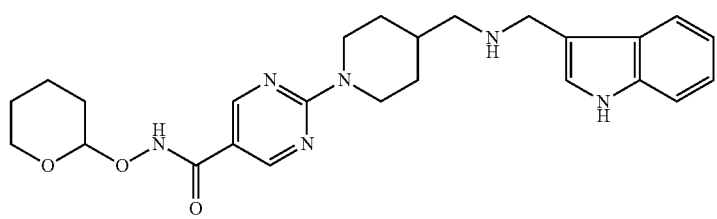 [SMILES: O=C(NOC1CCCCO1)c1cnc(N2CCC(CNCc3c[nH]c4ccccc34)CC2)nc1]
Interm. 27; Ex. [A1]; mp. 84° C.
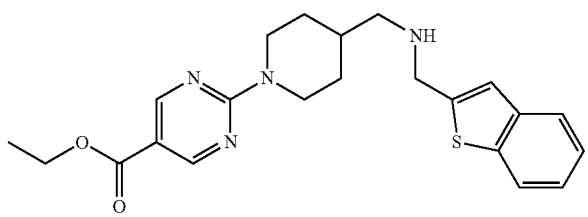 [SMILES: CCOC(=O)c1cnc(N2CCC(CNCc3cc4ccccc4s3)CC2)nc1]
Interm. 28; Ex. [A1]; mp. 83° C.

TABLE F-1-continued
(intermediates)
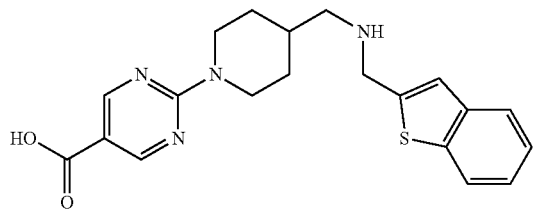 [SMILES: O=C(O)c1cnc(N2CCC(CNCc3cc4ccccc4s3)CC2)nc1]
•Na; Interm. 29; Ex. [A1]
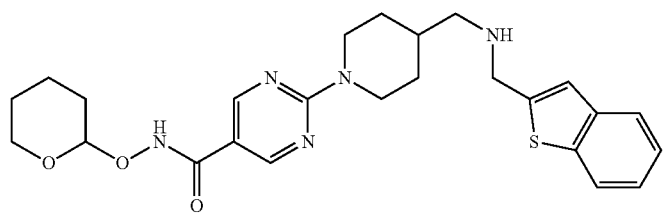 [SMILES: O=C(NOC1CCCCO1)c1cnc(N2CCC(CNCc3cc4ccccc4s3)CC2)nc1]
Interm. 30; Ex. [A1]
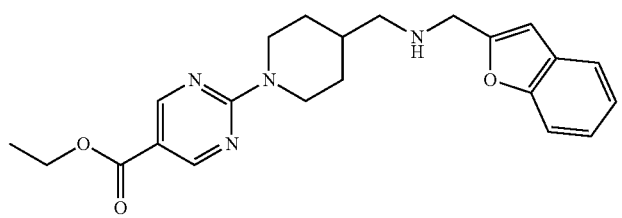 [SMILES: CCOC(=O)c1cnc(N2CCC(CNCc3cc4ccccc4o3)CC2)nc1]
Interm. 31; Ex. [A1]; mp. 85° C.
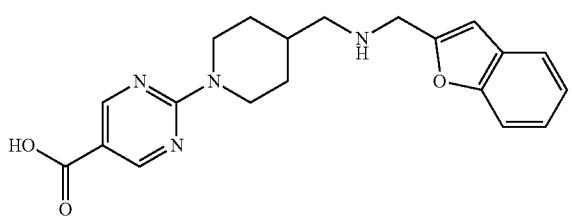 [SMILES: O=C(O)c1cnc(N2CCC(CNCc3cc4ccccc4o3)CC2)nc1]
•Na; Interm. 32; Ex. [A1]
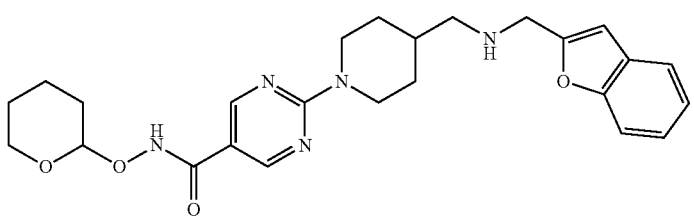 [SMILES: O=C(NOC1CCCCO1)c1cnc(N2CCC(CNCc3cc4ccccc4o3)CC2)nc1]
interm. 33; Ex. [A1]
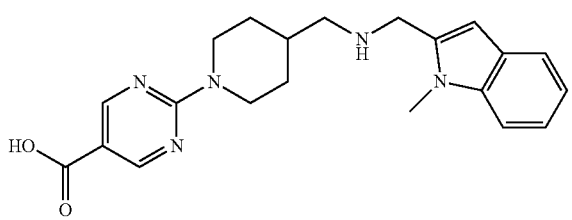 [SMILES: Cn1c(CNCC2CCN(c3ncc(C(=O)O)cn3)CC2)cc2ccccc21]
•Na; Interm. 34; Ex. [A1]

TABLE F-1-continued
(intermediates)
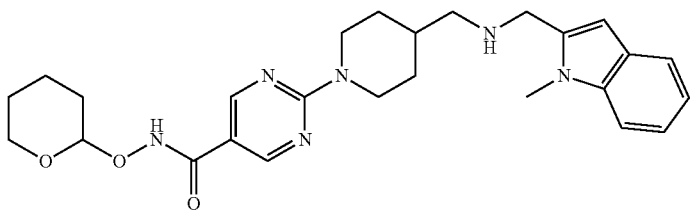 [SMILES: Cn1c(CNCC2CCN(c3ncc(C(=O)NOC4CCCCO4)cn3)CC2)cc2ccccc21]
Interm. 35; Ex. [A1]
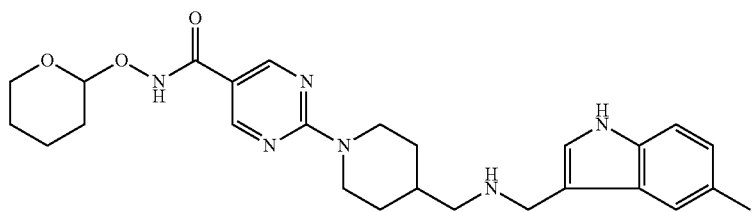 [SMILES: Cc1ccc2[nH]cc(CNCC3CCN(c4ncc(C(=O)NOC5CCCCO5)cn4)CC3)c2c1]
Interm. 36; Ex. [A2]
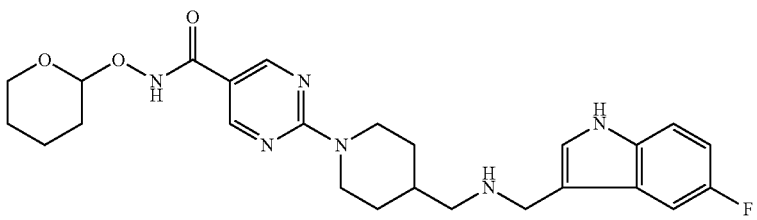 [SMILES: O=C(NOC1CCCCO1)c1cnc(N2CCC(CNCc3c[nH]c4ccc(F)cc34)CC2)nc1]
Interm. 37; Ex. [A2]
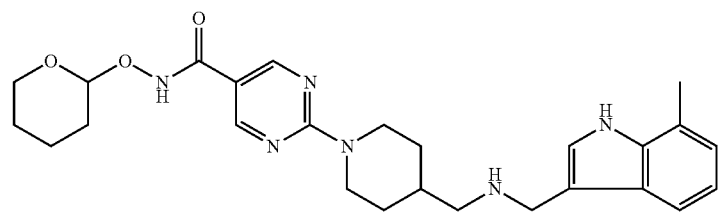 [SMILES: Cc1cccc2c(CNCC3CCN(c4ncc(C(=O)NOC5CCCCO5)cn4)CC3)c[nH]c12]
Interm. 38; Ex. [A2]; mp. 173° C.
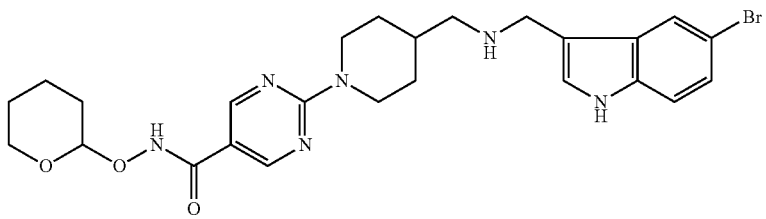 [SMILES: O=C(NOC1CCCCO1)c1cnc(N2CCC(CNCc3c[nH]c4ccc(Br)cc34)CC2)nc1]
Interm. 39; Ex. [A2]
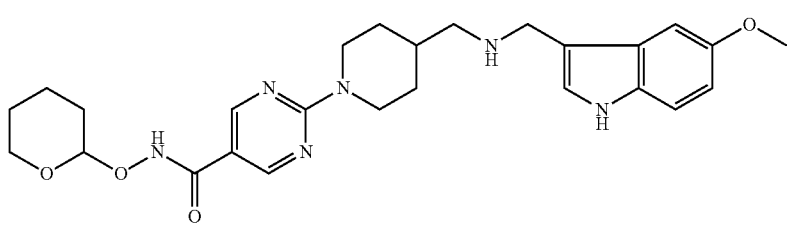 [SMILES: COc1ccc2[nH]cc(CNCC3CCN(c4ncc(C(=O)NOC5CCCCO5)cn4)CC3)c2c1]
Interm. 40; Ex. [A2]; mp. 110° C.

TABLE F-1-continued
(intermediates)
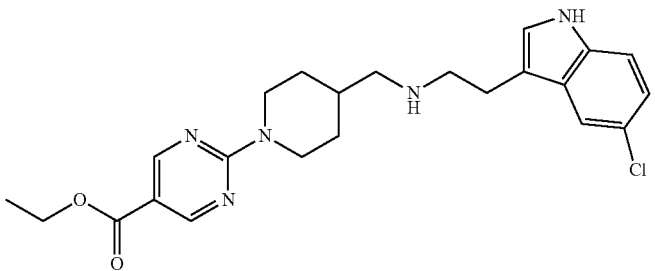 [SMILES: CCOC(=O)c1cnc(N2CCC(CNCCc3c[nH]c4ccc(Cl)cc34)CC2)nc1]
Interm. 41; Ex. [A3]; mp. 240° C.
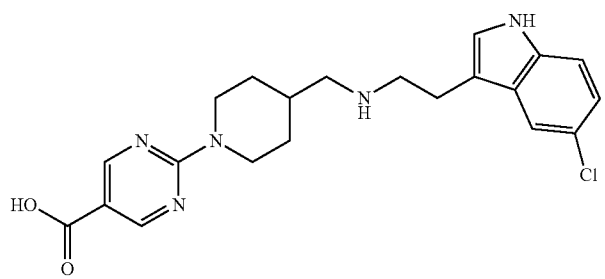 [SMILES: O=C(O)c1cnc(N2CCC(CNCCc3c[nH]c4ccc(Cl)cc34)CC2)nc1]
•Na; Interm. 42; Ex. [A3]
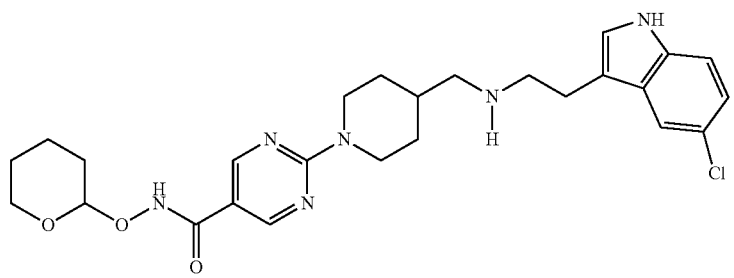 [SMILES: O=C(NOC1CCCCO1)c1cnc(N2CCC(CNCCc3c[nH]c4ccc(Cl)cc34)CC2)nc1]
Interm. 43; Ex. [A3]; mp. 88° C
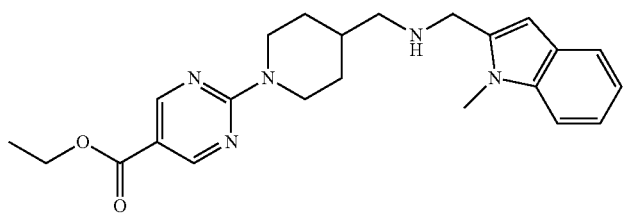 [SMILES: CCOC(=O)c1cnc(N2CCC(CNCc3cc4ccccc4n3C)CC2)nc1]
Interm. 44; ex. [A1]
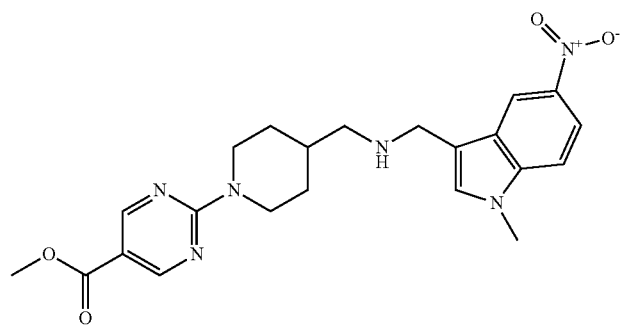 [SMILES: COC(=O)c1cnc(N2CCC(CNCc3cn(C)c4ccc([N+](=O)[O-])cc34)CC2)nc1]
Interm.. 46; Ex. [A5]; mp. 150° C.

TABLE F-1-continued
(intermediates)
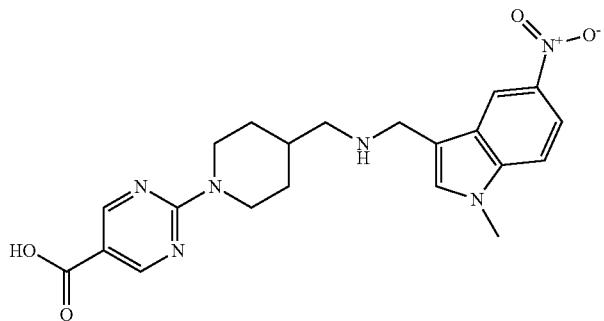 [SMILES: Cn1cc(CNCC2CCN(c3ncc(C(=O)O)cn3)CC2)c2cc([N+](=O)[O-])ccc21]
•Na; Interm. 47; Ex. [A5]
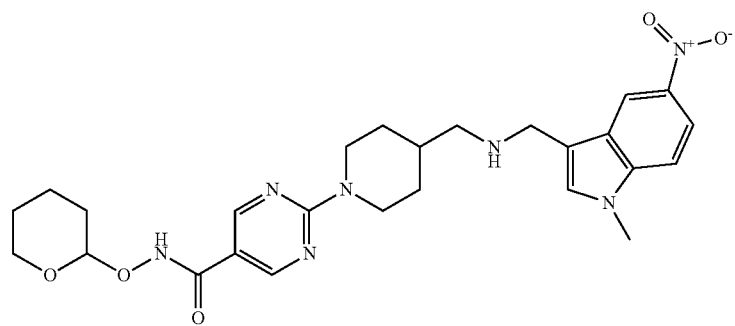 [SMILES: Cn1cc(CNCC2CCN(c3ncc(C(=O)NOC4CCCCO4)cn3)CC2)c2cc([N+](=O)[O-])ccc21]
Interm. 48; Ex. [A5]
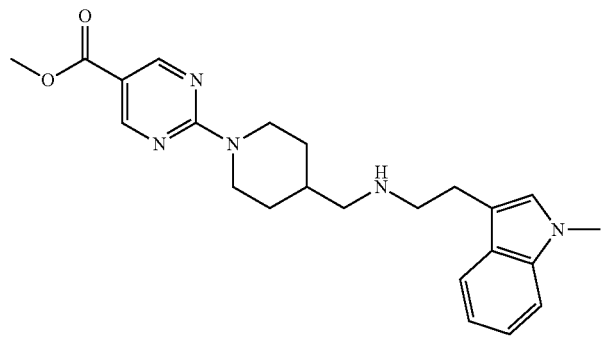
Interm.. 51; Ex. [A6]
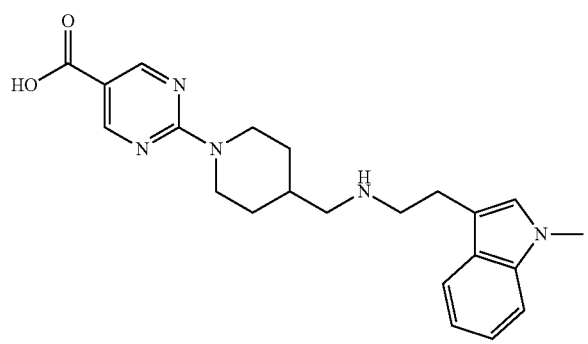 [SMILES: Cn1cc(CCNCC2CCN(c3ncc(C(=O)O)cn3)CC2)c2ccccc21]
•Na; Interm.52; Ex. [A6]

TABLE F-1-continued
(intermediates)
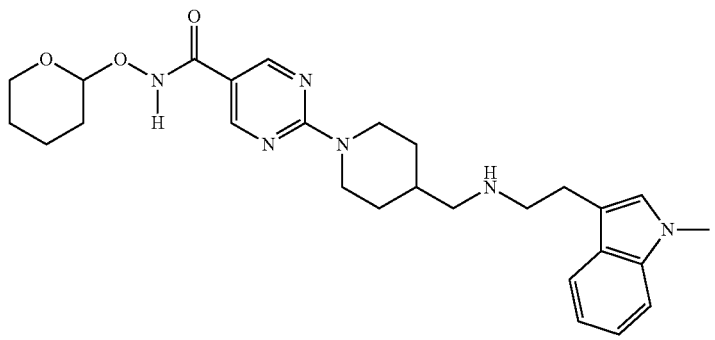 [SMILES: Cn1cc(CCNCC2CCN(c3ncc(C(=O)NOC4CCCCO4)cn3)CC2)c2ccccc21]
Interm. 53; Ex. [A6]
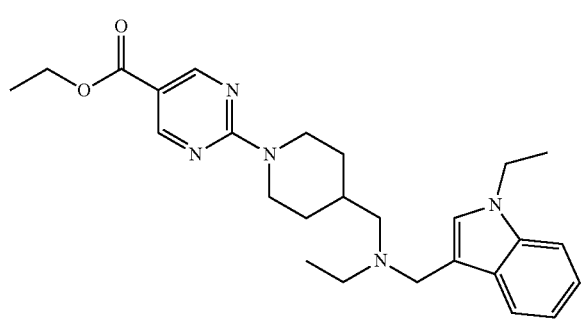 [SMILES: CCOC(=O)c1cnc(N2CCC(CN(CC)Cc3cn(CC)c4ccccc34)CC2)nc1]
Interm. 55; Ex. [A7]
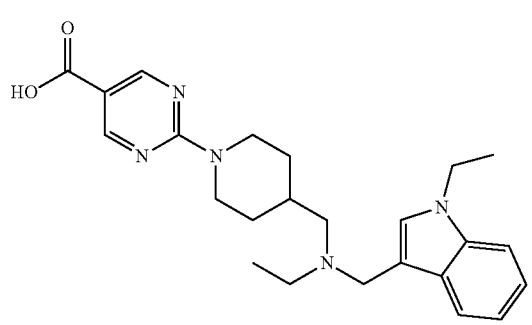 [SMILES: CCN(Cc1cn(CC)c2ccccc12)CC1CCN(c2ncc(C(=O)O)cn2)CC1]
•Na; Interm. 56; Ex. [A7]
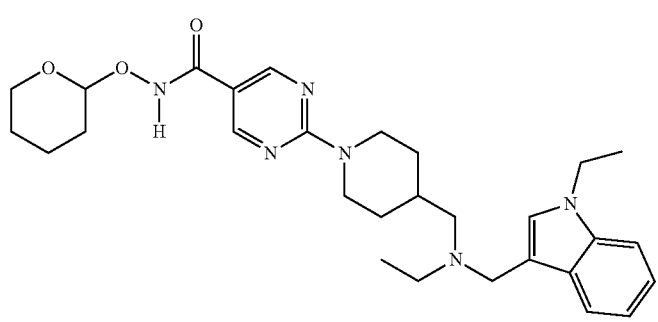 [SMILES: CCN(Cc1cn(CC)c2ccccc12)CC1CCN(c2ncc(C(=O)NOC3CCCCO3)cn2)CC1]
Interm. 57; Ex. [A7]

TABLE F-1-continued
(intermediates)
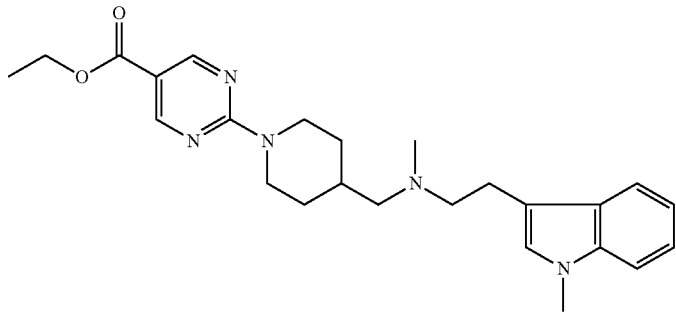 [SMILES: CCOC(=O)c1cnc(N2CCC(CN(C)CCc3cn(C)c4ccccc34)CC2)nc1]
Interm. 58; Ex. [A8]
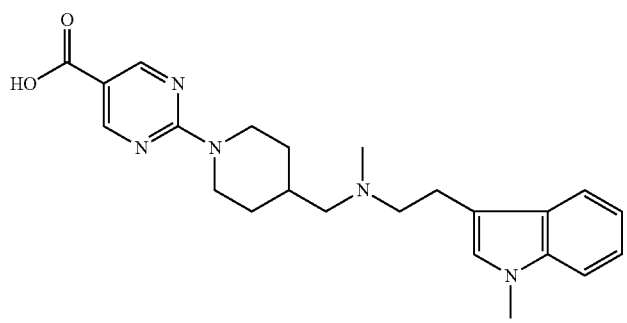 [SMILES: CN(CCc1cn(C)c2ccccc12)CC1CCN(c2ncc(C(=O)O)cn2)CC1]
•Na; Interm.59; Ex. [A8]
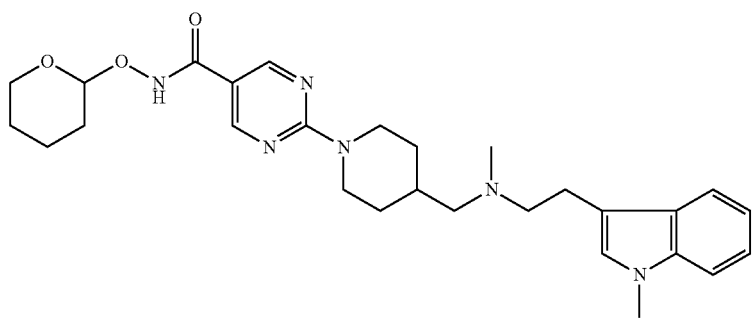 [SMILES: CN(CCc1cn(C)c2ccccc12)CC1CCN(c2ncc(C(=O)NOC3CCCCO3)cn2)CC1]
Interm. 60; Ex. [A8]
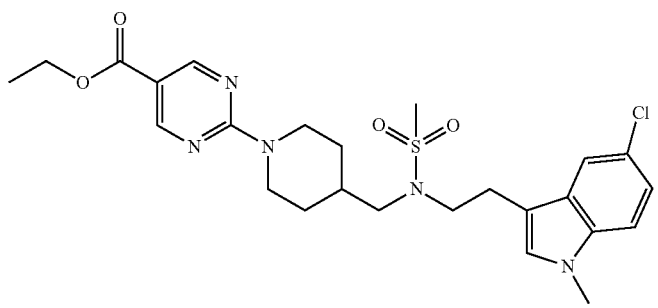 [SMILES: CCOC(=O)c1cnc(N2CCC(CN(CCc3cn(C)c4ccc(Cl)cc34)S(C)(=O)=O)CC2)nc1]
Interm.63; Ex.[A9]; mp. 162° C.

TABLE F-1-continued
(intermediates)
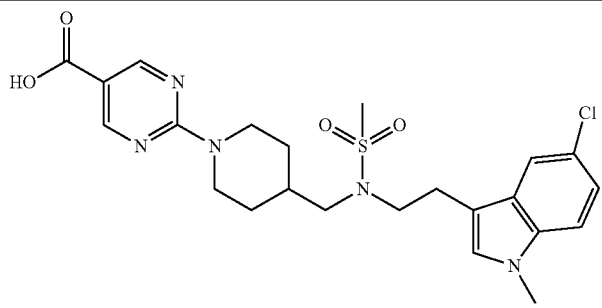
•Na; Interm.64; Ex. [A9]; mp. >260° C.
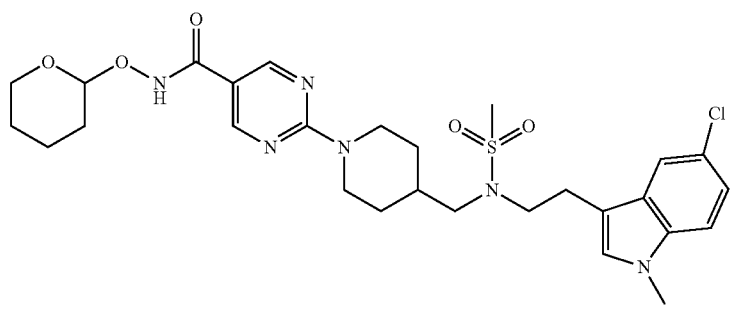 [SMILES: Cn1cc(CCN(CC2CCN(c3ncc(C(=O)NOC4CCCCO4)cn3)CC2)S(C)(=O)=O)c2cc(Cl)ccc21]
Interm..65 ; Ex. [A9]; mp. 179° C.
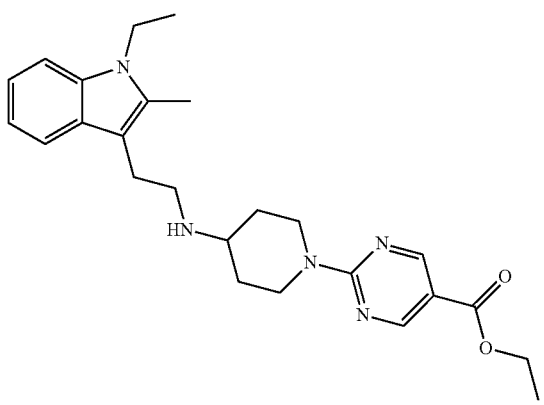 [SMILES: CCOC(=O)c1cnc(N2CCC(NCCc3c(C)n(CC)c4ccccc34)CC2)nc1]
Interm. 70; Ex. [A11]
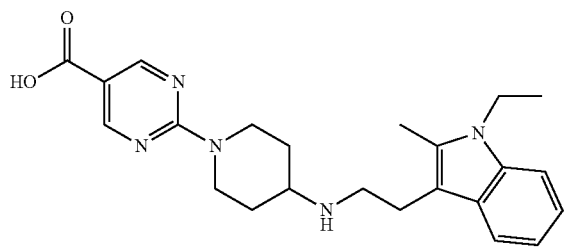 [SMILES: CCn1c(C)c(CCNC2CCN(c3ncc(C(=O)O)cn3)CC2)c2ccccc21]
•Na; Interm. 71; Ex. [A11]
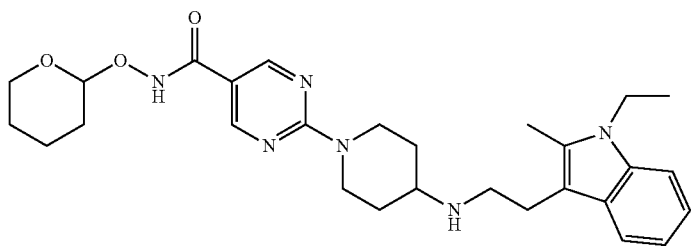 [SMILES: CCn1c(C)c(CCNC2CCN(c3ncc(C(=O)NOC4CCCCO4)cn3)CC2)c2ccccc21]
Interm.72; Ex. [A11]

TABLE F-1-continued
(intermediates)
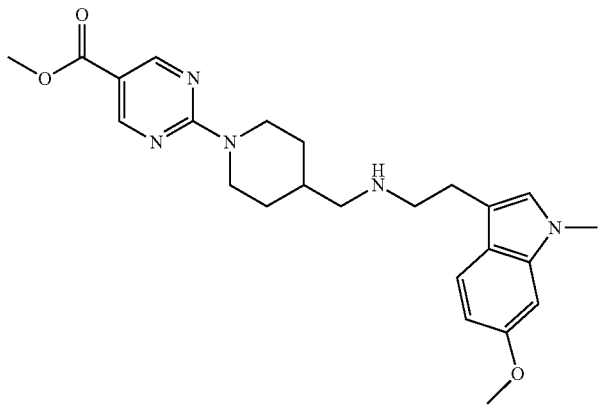
Interm. 73; Ex. [A12]; mp. 122° C.
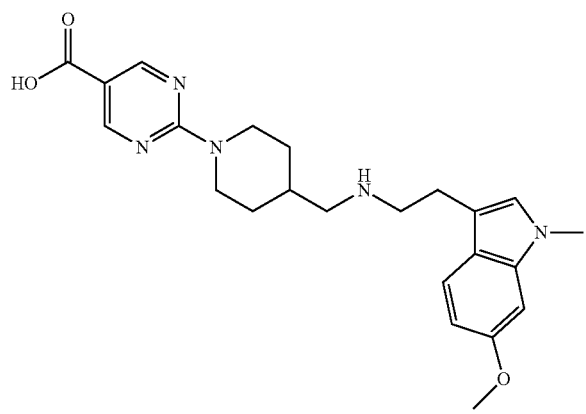 [SMILES: COc1ccc2c(CCNCC3CCN(c4ncc(C(=O)O)cn4)CC3)cn(C)c2c1]
•Na; Interm.74; Ex. [A12]
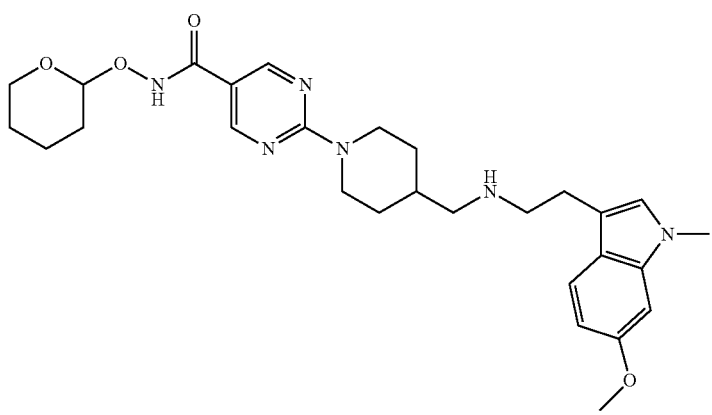 [SMILES: COc1ccc2c(CCNCC3CCN(c4ncc(C(=O)NOC5CCCCO5)cn4)CC3)cn(C)c2c1]
Interm. 75; Ex. [A12]
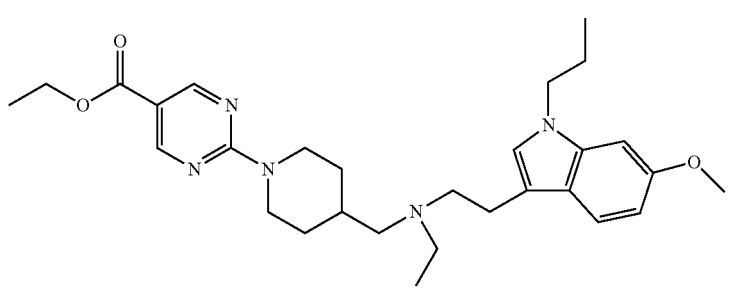 [SMILES: CCCn1cc(CCN(CC)CC2CCN(c3ncc(C(=O)OCC)cn3)CC2)c2ccc(OC)cc21]
Interm.80; Ex. [A13]

TABLE F-1-continued
(intermediates)
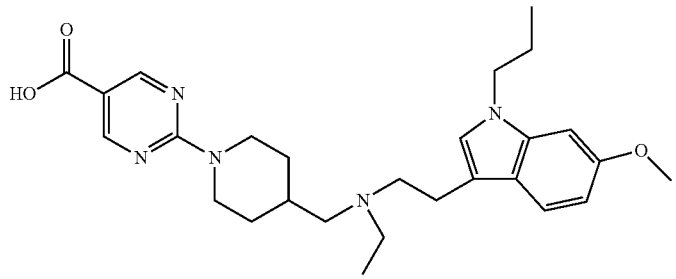 [SMILES: CCCn1cc(CCN(CC)CC2CCN(c3ncc(C(=O)O)cn3)CC2)c2ccc(OC)cc21]
•Na; Interm. 81; Ex. [A13]; mp. >260° C.
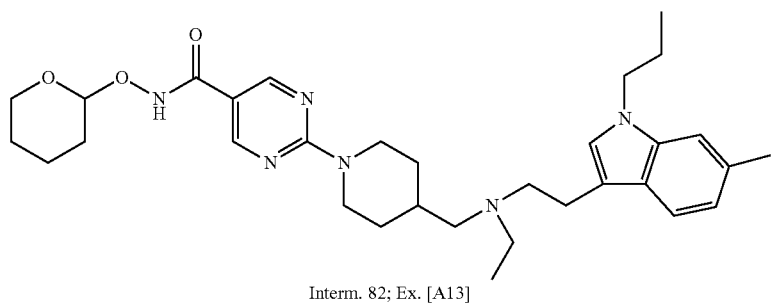
Interm. 82; Ex. [A13]
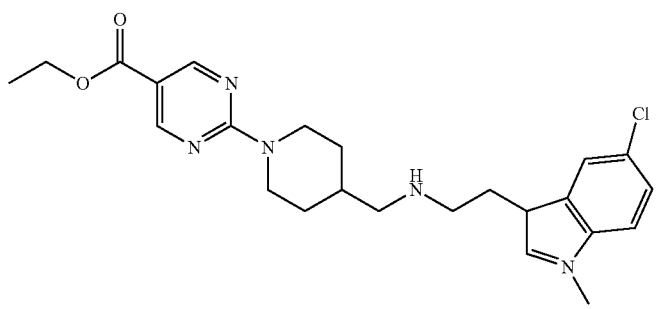
Interm. 62; Ex. [A9]
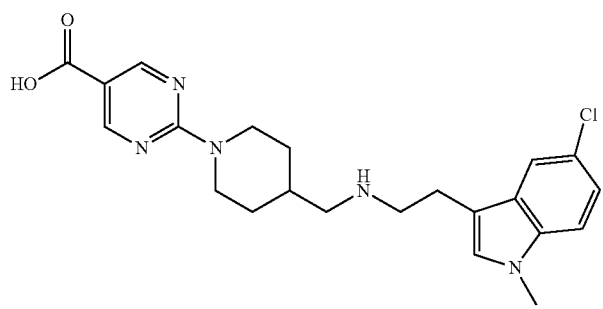 [SMILES: Cn1cc(CCNCC2CCN(c3ncc(C(=O)O)cn3)CC2)c2cc(Cl)ccc21]
•Na; Interm.83; Ex. [A14]; mp. >260° C.
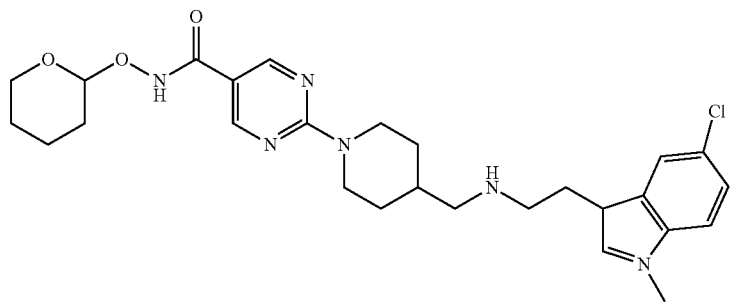
Interm. 84; Ex. [A14]

TABLE F-1-continued
(intermediates)
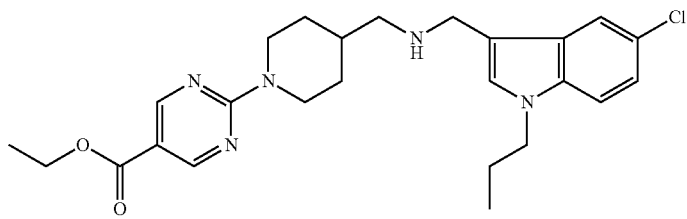 [SMILES: CCCn1cc(CNCC2CCN(c3ncc(C(=O)OCC)cn3)CC2)c2cc(Cl)ccc21]
Interm. 87; Ex. [A16]
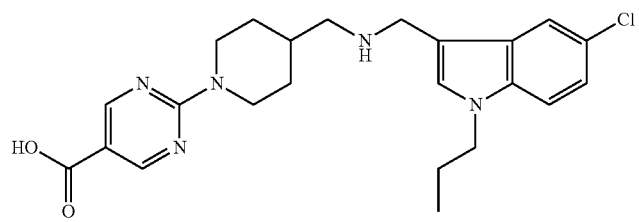 [SMILES: CCCn1cc(CNCC2CCN(c3ncc(C(=O)O)cn3)CC2)c2cc(Cl)ccc21]
•Na; Interm. 88; Ex. [A16]; mp. >260° C.
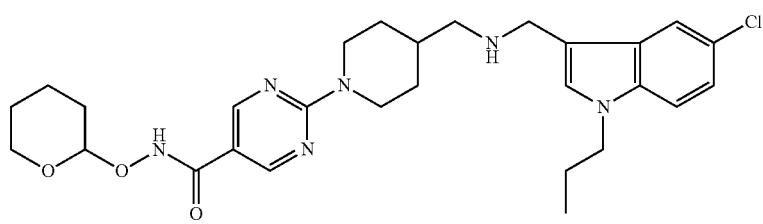 [SMILES: CCCn1cc(CNCC2CCN(c3ncc(C(=O)NOC4CCCCO4)cn3)CC2)c2cc(Cl)ccc21]
Interm. 89; Ex.[A16]
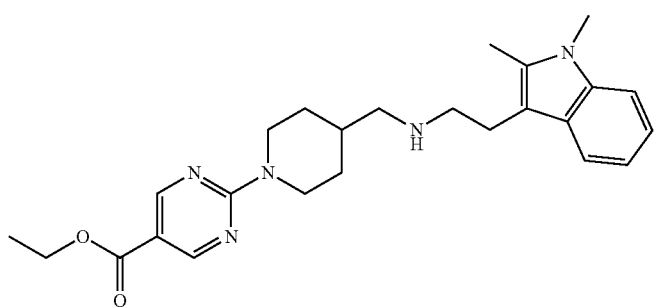 [SMILES: CCOC(=O)c1cnc(N2CCC(CNCCc3c(C)n(C)c4ccccc34)CC2)nc1]
Interm.91; Ex. [A17]
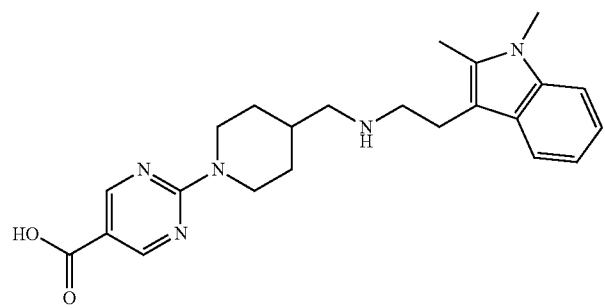 [SMILES: Cc1c(CCNCC2CCN(c3ncc(C(=O)O)cn3)CC2)c2ccccc2n1C]
•Na; Interm. 92; Ex. [A17]; mp. >260° C.

TABLE F-1-continued
(intermediates)
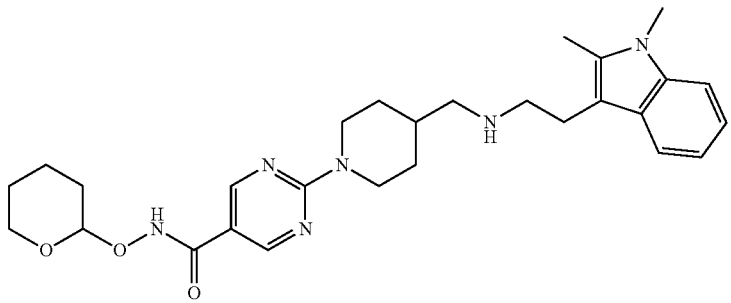 [SMILES: Cc1c(CCNCC2CCN(c3ncc(C(=O)NOC4CCCCO4)cn3)CC2)c2ccccc2n1C]
Interm. 93; Ex. [A17]
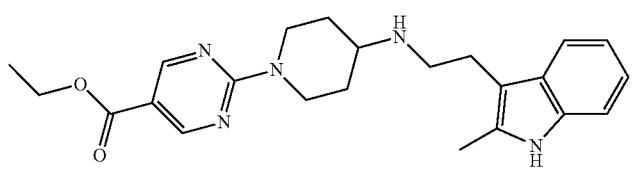 [SMILES: CCOC(=O)c1cnc(N2CCC(NCCc3c(C)[nH]c4ccccc34)CC2)nc1]
Interm. 94; Ex. [A1]
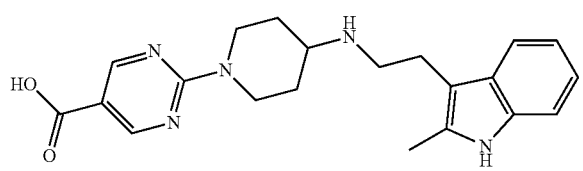 [SMILES: Cc1[nH]c2ccccc2c1CCNC1CCN(c2ncc(C(=O)O)cn2)CC1]
•Na; Interm. 95; Ex. [A1]
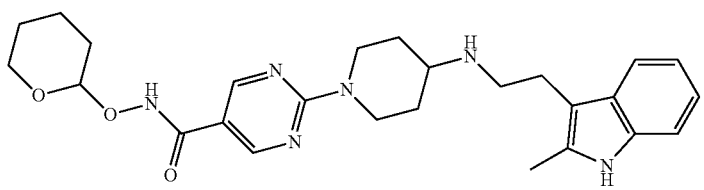 [SMILES: Cc1[nH]c2ccccc2c1CCNC1CCN(c2ncc(C(=O)NOC3CCCCO3)cn2)CC1]
Interm. 96; Ex. [A1]
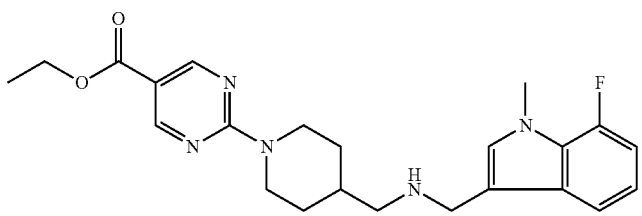 [SMILES: CCOC(=O)c1cnc(N2CCC(CNCc3cn(C)c4c(F)cccc34)CC2)nc1]
Interm. 97; Ex. [A1]
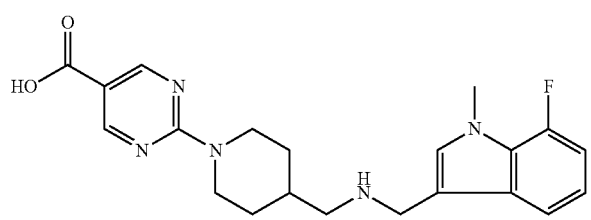 [SMILES: Cn1cc(CNCC2CCN(c3ncc(C(=O)O)cn3)CC2)c2cccc(F)c21]
•Na; Interm. 98; Ex. [A1]

TABLE F-1-continued
(intermediates)
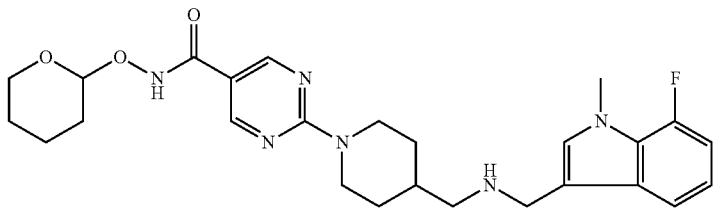 [SMILES: Cn1cc(CNCC2CCN(c3ncc(C(=O)NOC4CCCCO4)cn3)CC2)c2cccc(F)c21]
Interm. 99; Ex. [A1]
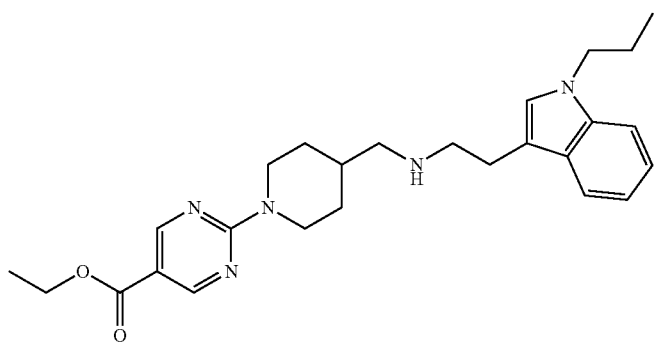 [SMILES: CCCn1cc(CCNCC2CCN(c3ncc(C(=O)OCC)cn3)CC2)c2ccccc21]
Interm.100; Ex. [A1]
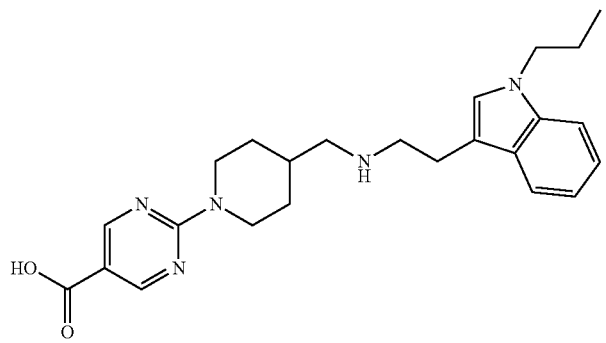 [SMILES: CCCn1cc(CCNCC2CCN(c3ncc(C(=O)O)cn3)CC2)c2ccccc21]
•Na; Interm. 101; Ex. [A1]; mp. >260° C.
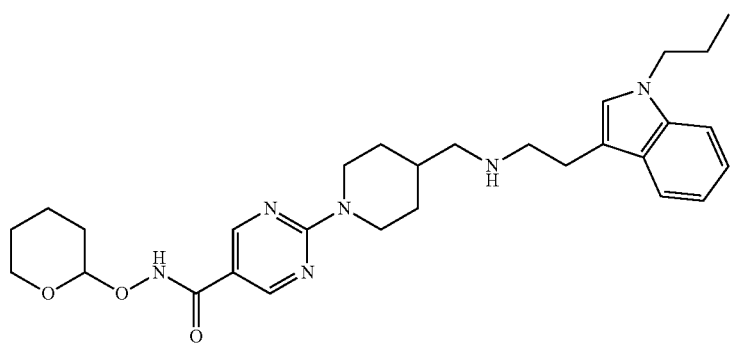 [SMILES: CCCn1cc(CCNCC2CCN(c3ncc(C(=O)NOC4CCCCO4)cn3)CC2)c2ccccc21]
Interm.102; Ex. [A1]

TABLE F-1-continued
(intermediates)
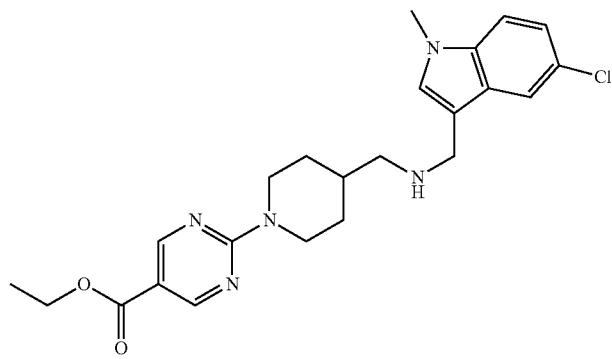 [SMILES: CCOC(=O)c1cnc(N2CCC(CNCc3cn(C)c4ccc(Cl)cc34)CC2)nc1]
Interm. 103; Ex. [A1]
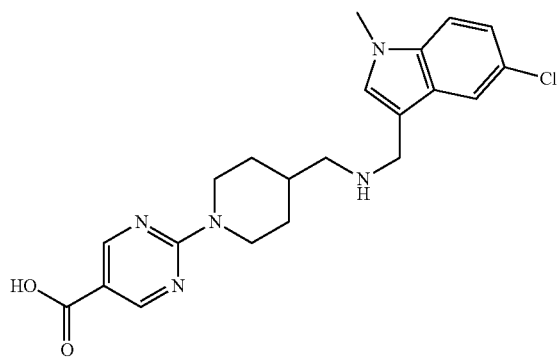 [SMILES: Cn1cc(CNCC2CCN(c3ncc(C(=O)O)cn3)CC2)c2cc(Cl)ccc21]
•Na; Interm. 104; Ex. [A1]; mp. >260° C.
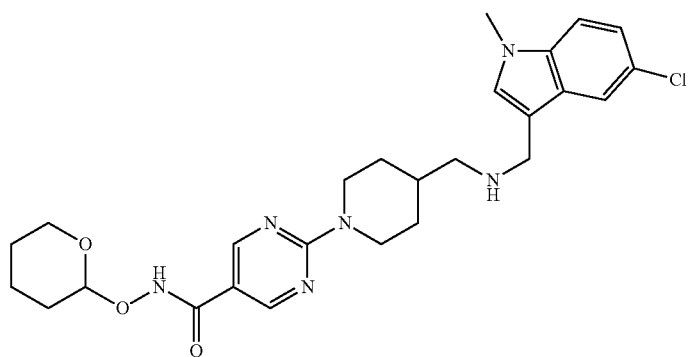 [SMILES: Cn1cc(CNCC2CCN(c3ncc(C(=O)NOC4CCCCO4)cn3)CC2)c2cc(Cl)ccc21]
Interm. 105; Ex. [A1]; mp. 80° C.
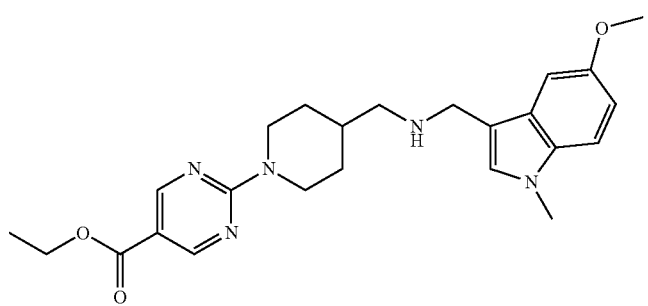 [SMILES: CCOC(=O)c1cnc(N2CCC(CNCc3cn(C)c4ccc(OC)cc34)CC2)nc1]
Interm.106; Ex. [A1]

TABLE F-1-continued
(intermediates)
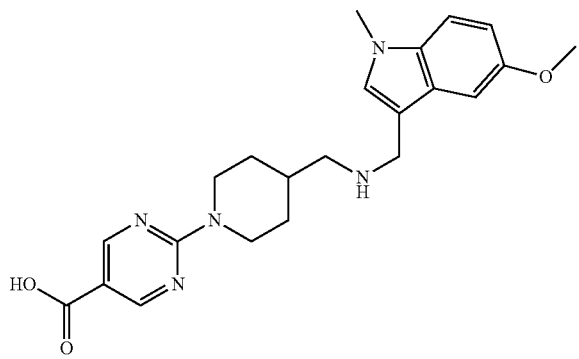 [SMILES: COc1ccc2c(c1)c(CNCC1CCN(c3ncc(C(=O)O)cn3)CC1)cn2C]
•Na; Interm. 107; Ex. [A1]; mp. >260° C.
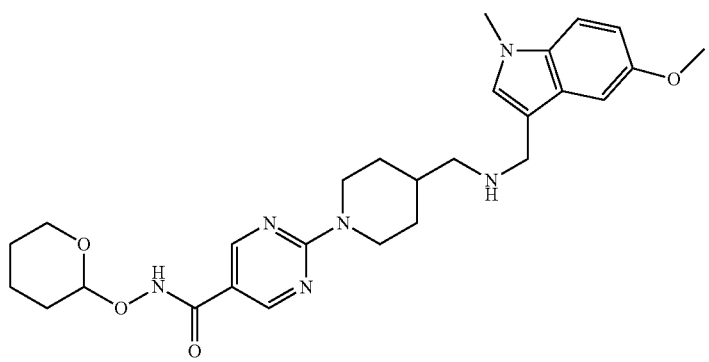 [SMILES: COc1ccc2c(c1)c(CNCC1CCN(c3ncc(C(=O)NOC4CCCCO4)cn3)CC1)cn2C]
Interm. 108; Ex. [A1]; mp. 80° C.
Interm. 109; Ex. [A1]; mp. ° C.
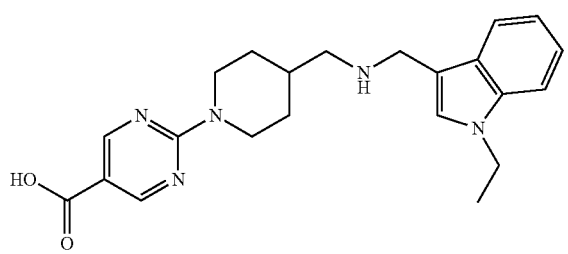 [SMILES: CCn1cc(CNCC2CCN(c3ncc(C(=O)O)cn3)CC2)c2ccccc21]
•Na; Interm. 110; Ex. [A1]; mp. 260° C.
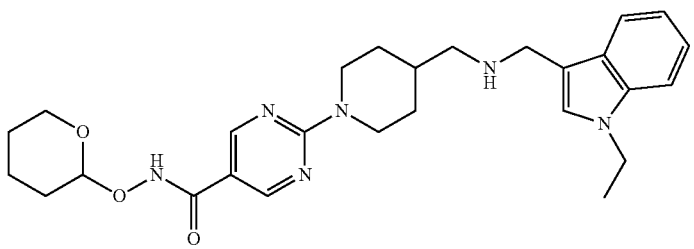 [SMILES: CCn1cc(CNCC2CCN(c3ncc(C(=O)NOC4CCCCO4)cn3)CC2)c2ccccc21]
Interm. 111; Ex. [A1]
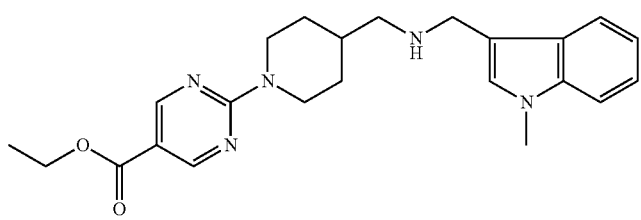 [SMILES: CCOC(=O)c1cnc(N2CCC(CNCc3cn(C)c4ccccc34)CC2)nc1]
Interm. 112; Ex. [A1]

TABLE F-1-continued
(intermediates)
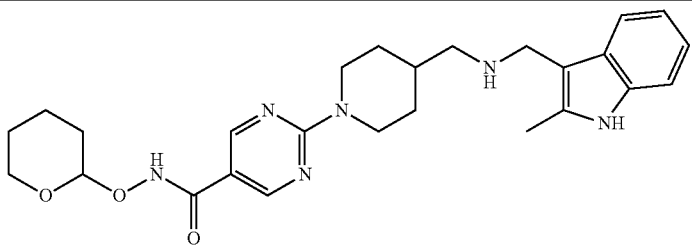
Interm. 113; Ex. [A1]
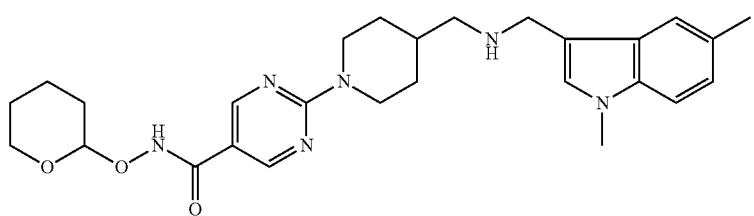 [SMILES: Cc1ccc2c(c1)c(CNCC1CCN(c3ncc(C(=O)NOC4CCCCO4)cn3)CC1)cn2C]
Interm. 114; Ex. [A2]
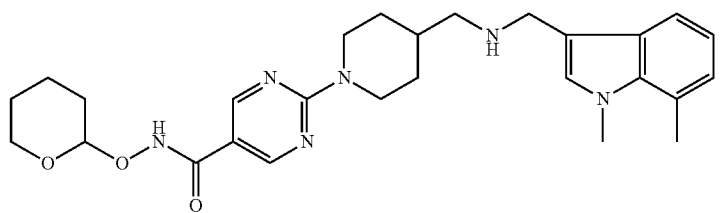 [SMILES: Cc1cccc2c(CNCC3CCN(c4ncc(C(=O)NOC5CCCCO5)cn4)CC3)cn(C)c12]
Interm. 115; Ex. [A2]
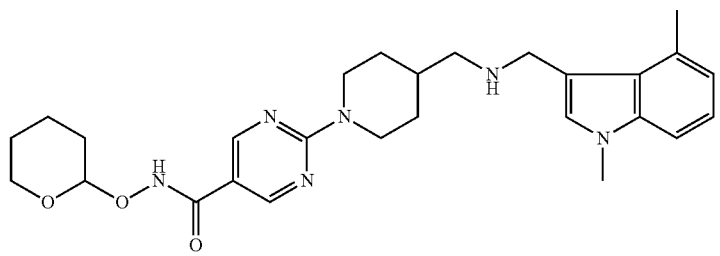 [SMILES: Cc1cccc2c1c(CNCC1CCN(c3ncc(C(=O)NOC4CCCCO4)cn3)CC1)cn2C]
Interm..116; Ex. [A2]
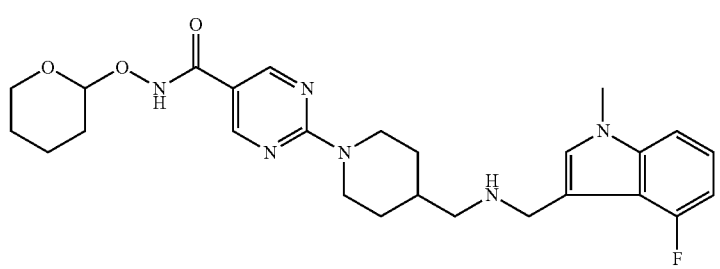 [SMILES: Cn1cc(CNCC2CCN(c3ncc(C(=O)NOC4CCCCO4)cn3)CC2)c2c(F)cccc21]
Interm. 117; Ex. [A2]
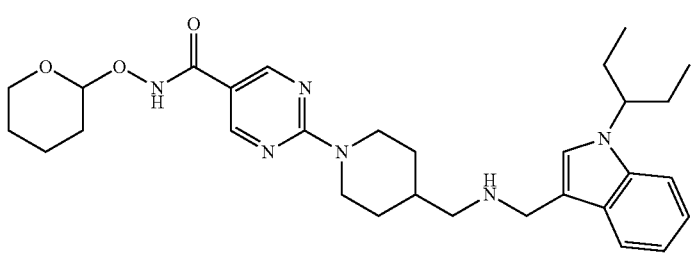 [SMILES: CCC(CC)n1cc(CNCC2CCN(c3ncc(C(=O)NOC4CCCCO4)cn3)CC2)c2ccccc21]
Interm. 118; Ex. [A2]

TABLE F-1-continued
(intermediates)
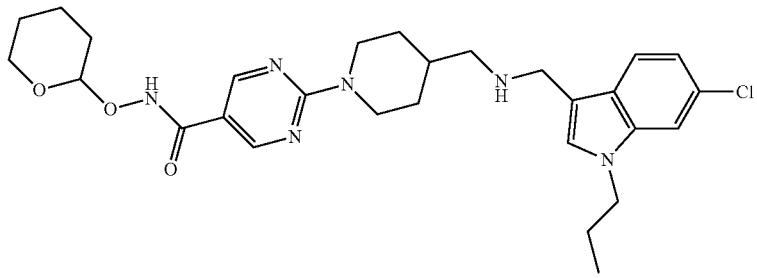 [SMILES: CCCn1cc(CNCC2CCN(c3ncc(C(=O)NOC4CCCCO4)cn3)CC2)c2ccc(Cl)cc21]
Interm. 119; Ex. [A2]
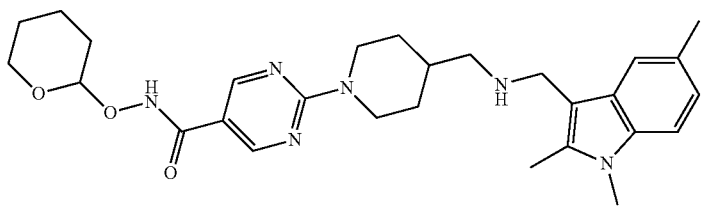 [SMILES: Cc1ccc2c(c1)c(CNCC1CCN(c3ncc(C(=O)NOC4CCCCO4)cn3)CC1)c(C)n2C]
Interm. 120; Ex. [A2]
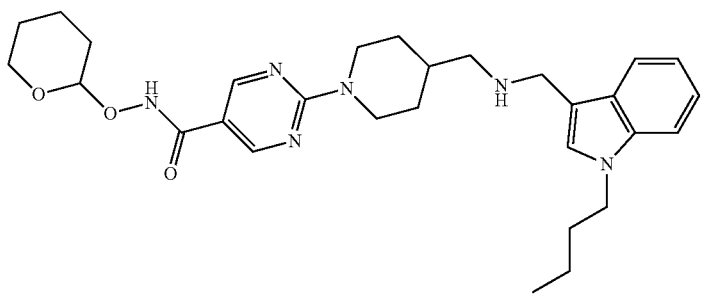 [SMILES: CCCCn1cc(CNCC2CCN(c3ncc(C(=O)NOC4CCCCO4)cn3)CC2)c2ccccc21]
Interm. 121; Ex. [A2]
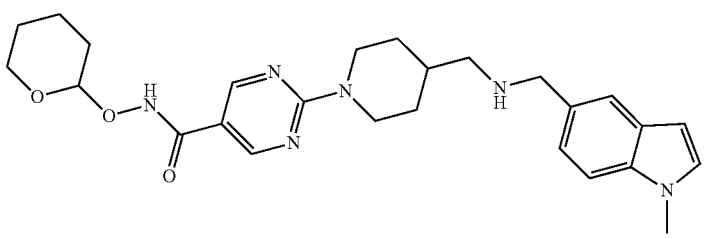 [SMILES: Cn1ccc2cc(CNCC3CCN(c4ncc(C(=O)NOC5CCCCO5)cn4)CC3)ccc21]
Interm. 122; Ex. [A2]
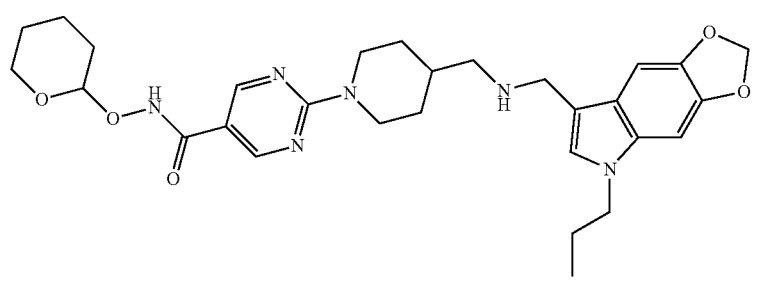 [SMILES: CCCn1cc(CNCC2CCN(c3ncc(C(=O)NOC4CCCCO4)cn3)CC2)c2cc3c(cc21)OCO3]
Interm.. 123; Ex. [A2]

TABLE F-1-continued
(intermediates)
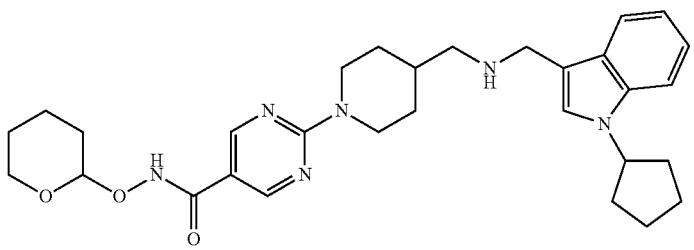 [SMILES: O=C(NOC1CCCCO1)c1cnc(N2CCC(CNCc3cn(C4CCCC4)c4ccccc34)CC2)nc1]
Interm. 124; Ex. [A2]
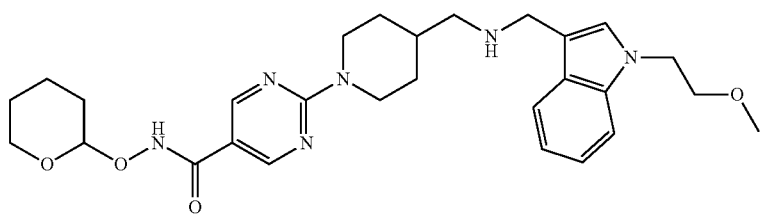 [SMILES: COCCn1cc(CNCC2CCN(c3ncc(C(=O)NOC4CCCCO4)cn3)CC2)c2ccccc21]
Interm. 125; Ex. [A2]
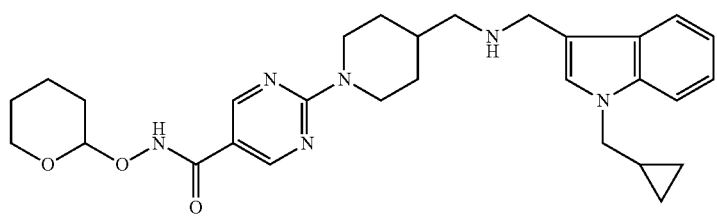 [SMILES: O=C(NOC1CCCCO1)c1cnc(N2CCC(CNCc3cn(CC4CC4)c4ccccc34)CC2)nc1]
Interm. 126; Ex. [A2]
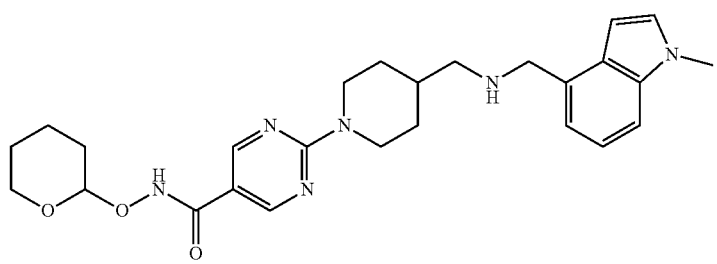 [SMILES: Cn1ccc2c(CNCC3CCN(c4ncc(C(=O)NOC5CCCCO5)cn4)CC3)cccc21]
Interm. 127; Ex. [A2]
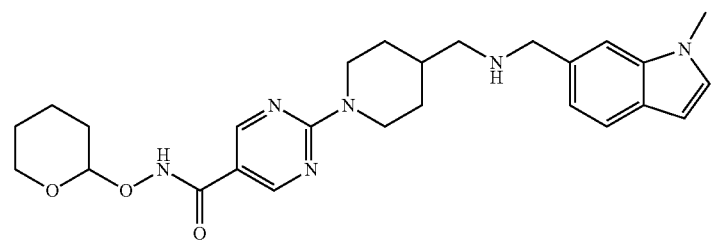 [SMILES: Cn1ccc2ccc(CNCC3CCN(c4ncc(C(=O)NOC5CCCCO5)cn4)CC3)cc21]
Interm.128 ; Ex. [A2]
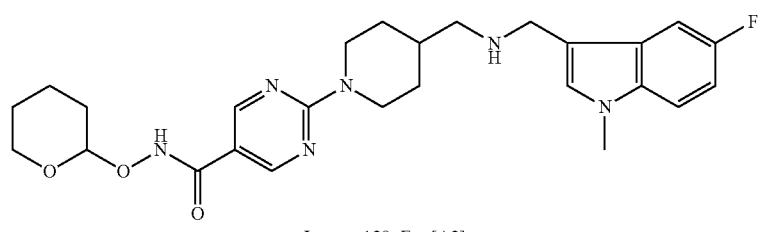
Interm. 129; Ex. [A2]

TABLE F-1-continued
(intermediates)
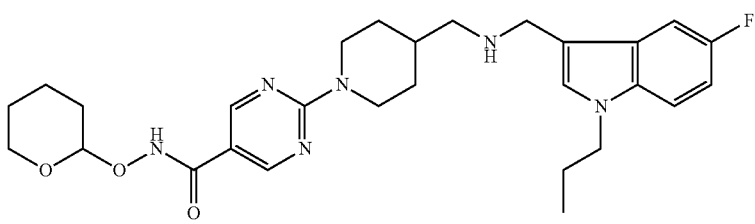 [SMILES: CCCn1cc(CNCC2CCN(c3ncc(C(=O)NOC4CCCCO4)cn3)CC2)c2cc(F)ccc21]
Interm. 130; Ex. [A2]
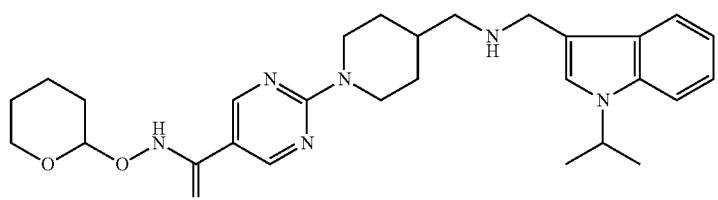
Interm. 131; Ex. [A2]
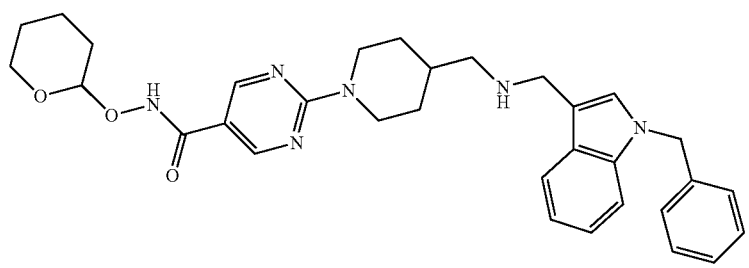 [SMILES: O=C(NOC1CCCCO1)c1cnc(N2CCC(CNCc3cn(Cc4ccccc4)c4ccccc34)CC2)nc1]
Interm. 132; Ex. [A2]
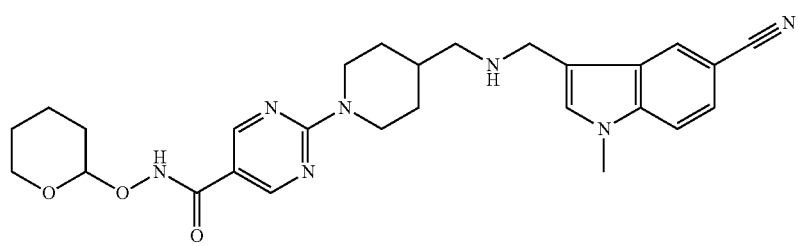 [SMILES: Cn1cc(CNCC2CCN(c3ncc(C(=O)NOC4CCCCO4)cn3)CC2)c2cc(C#N)ccc21]
Interm. 133; Ex. [A2]
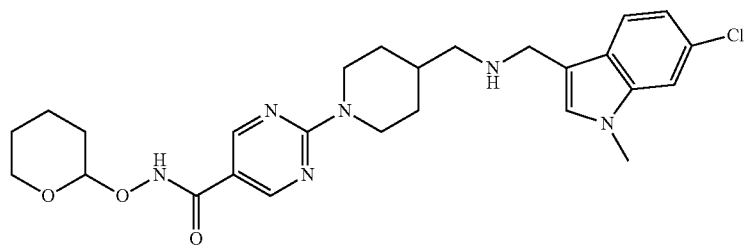 [SMILES: Cn1cc(CNCC2CCN(c3ncc(C(=O)NOC4CCCCO4)cn3)CC2)c2ccc(Cl)cc21]
Interm. 134; Ex. [A2]
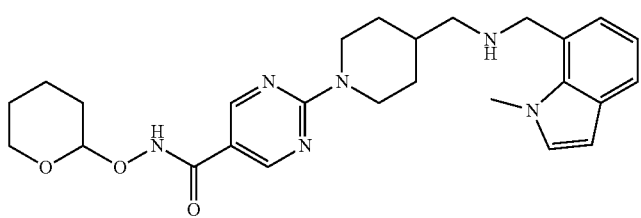 [SMILES: Cn1ccc2cccc(CNCC3CCN(c4ncc(C(=O)NOC5CCCCO5)cn4)CC3)c21]
Interm. 135; Ex. [A2]

TABLE F-1-continued
(intermediates)
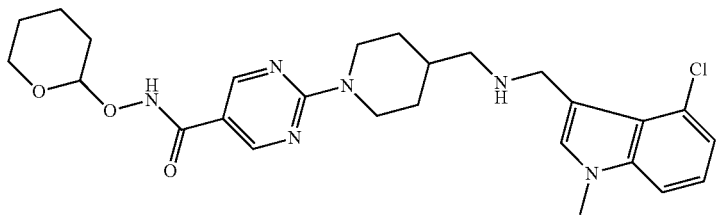 [SMILES: Cn1cc(CNCC2CCN(c3ncc(C(=O)NOC4CCCCO4)cn3)CC2)c2c(Cl)cccc21]
Interm. 136; Ex. [A2]
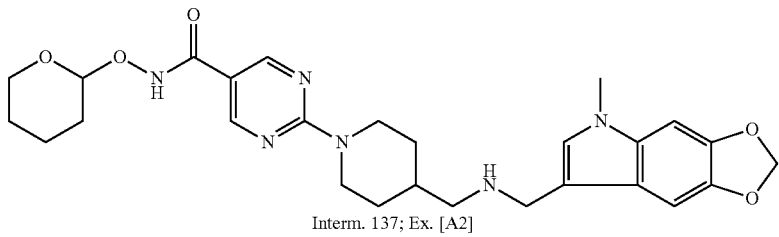
Interm. 137; Ex. [A2]
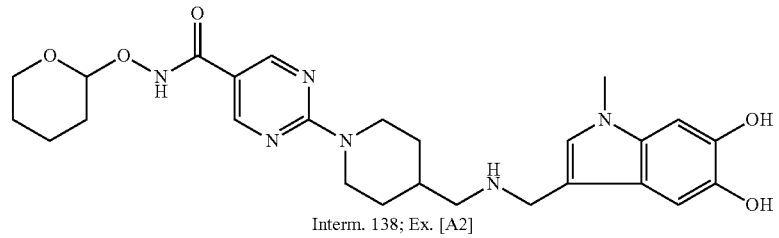
Interm. 138; Ex. [A2]
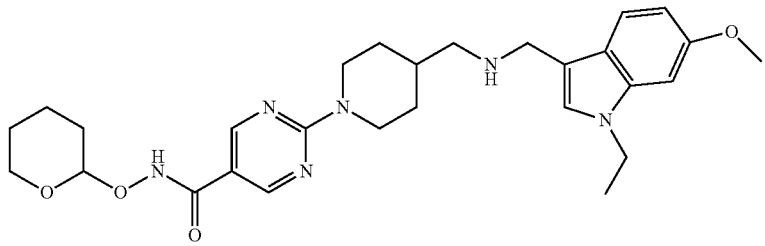 [SMILES: CCn1cc(CNCC2CCN(c3ncc(C(=O)NOC4CCCCO4)cn3)CC2)c2ccc(OC)cc21]
Interm. 139; Ex. [A2]
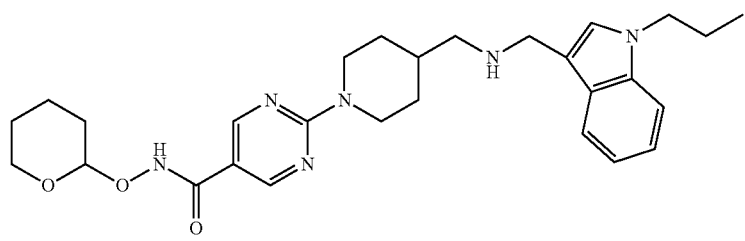 [SMILES: CCCn1cc(CNCC2CCN(c3ncc(C(=O)NOC4CCCCO4)cn3)CC2)c2ccccc21]
Interm. 140; Ex. [A2]
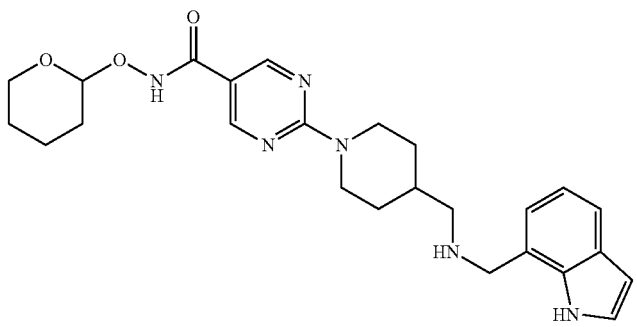 [SMILES: O=C(NOC1CCCCO1)c1cnc(N2CCC(CNCc3cccc4cc[nH]c34)CC2)nc1]
Interm. 141; Ex. [A2]

TABLE F-1-continued
(intermediates)
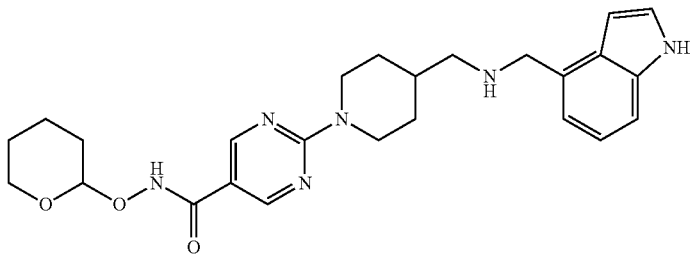 [SMILES: O=C(NOC1CCCCO1)c1cnc(N2CCC(CNCc3cccc4[nH]ccc34)CC2)nc1]
Interm. 142; Ex. [A2]
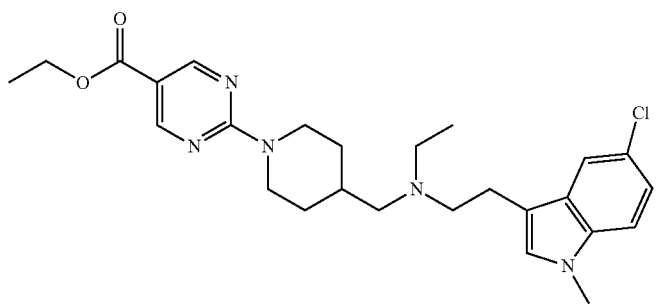 [SMILES: CCOC(=O)c1cnc(N2CCC(CN(CC)CCc3cn(C)c4ccc(Cl)cc34)CC2)nc1]
Interm. 143; Ex. [A7]
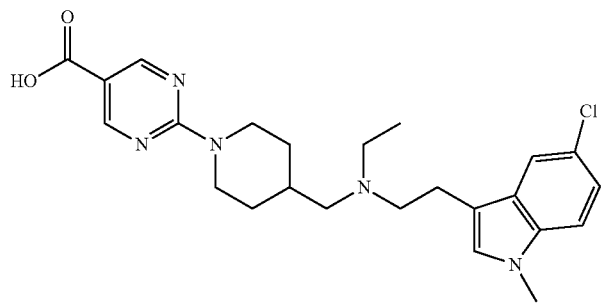 [SMILES: CCN(CCc1cn(C)c2ccc(Cl)cc12)CC1CCN(c2ncc(C(=O)O)cn2)CC1]
•Na; Interm. 144; Ex. [A7]; mp. >260° C.
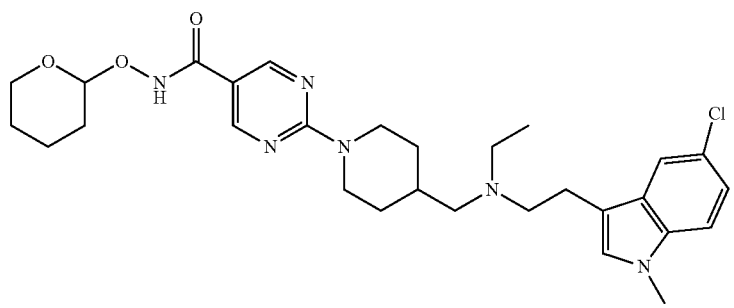 [SMILES: CCN(CCc1cn(C)c2ccc(Cl)cc12)CC1CCN(c2ncc(C(=O)NOC3CCCCO3)cn2)CC1]
Interm. 145; Ex. [A7]

TABLE F-1-continued
(intermediates)
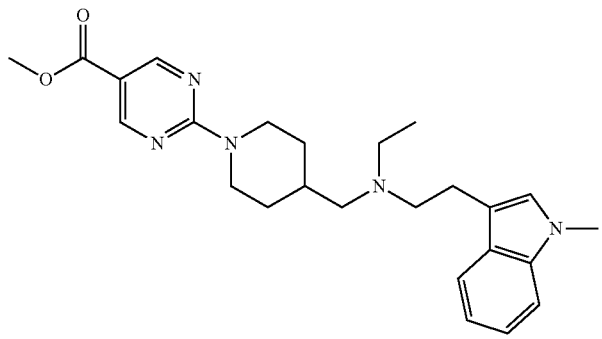
Interm. 146; Ex. [A7]
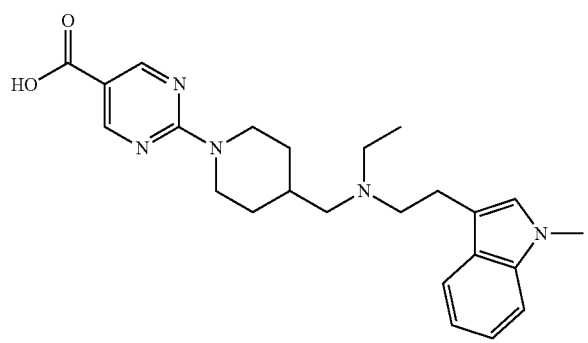 [SMILES: CCN(CCc1cn(C)c2ccccc12)CC1CCN(c2ncc(C(=O)O)cn2)CC1]
•Na; Interm. 147; Ex. [A7]; mp. >260° C.
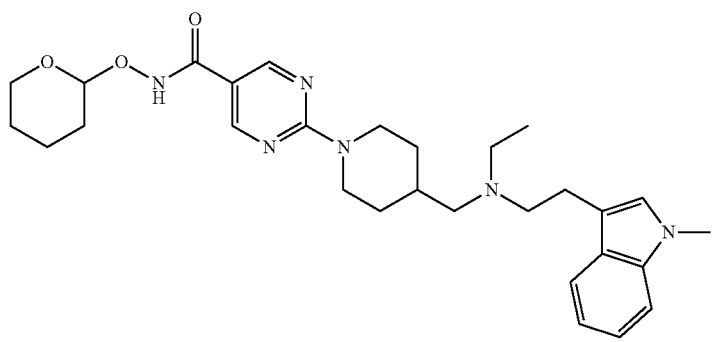 [SMILES: CCN(CCc1cn(C)c2ccccc12)CC1CCN(c2ncc(C(=O)NOC3CCCCO3)cn2)CC1]
Interm. 148; Ex. [A7]
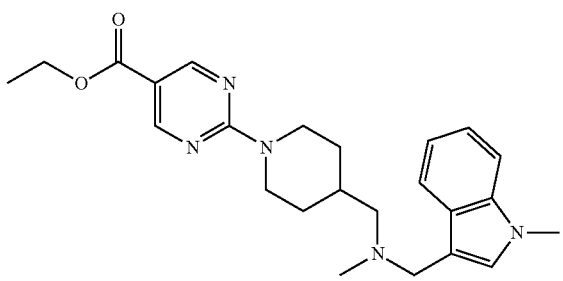 [SMILES: CCOC(=O)c1cnc(N2CCC(CN(C)Cc3cn(C)c4ccccc34)CC2)nc1]
Interm.. 149; Ex. [A7]

TABLE F-1-continued
(intermediates)
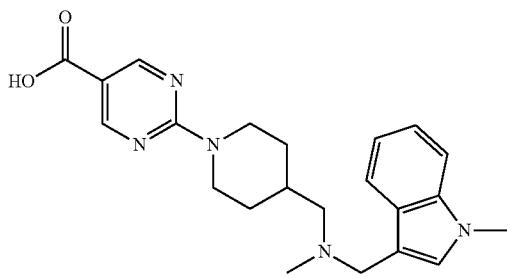 [SMILES: CN(Cc1cn(C)c2ccccc12)CC1CCN(c2ncc(C(=O)O)cn2)CC1]
•Na; Interm. 150; Ex. [A7]
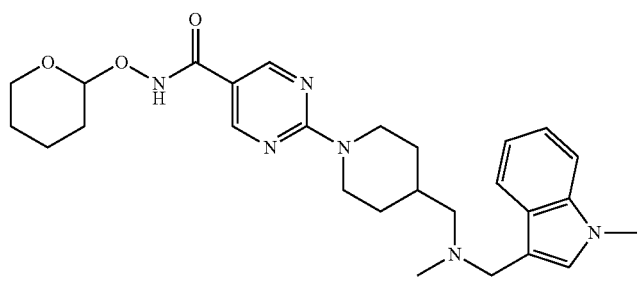 [SMILES: CN(Cc1cn(C)c2ccccc12)CC1CCN(c2ncc(C(=O)NOC3CCCCO3)cn2)CC1]
Interm. 151; Ex. [A7]
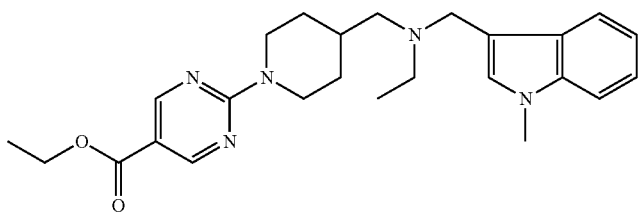 [SMILES: CCOC(=O)c1cnc(N2CCC(CN(CC)Cc3cn(C)c4ccccc34)CC2)nc1]
Interm. 152; Ex. [A7]
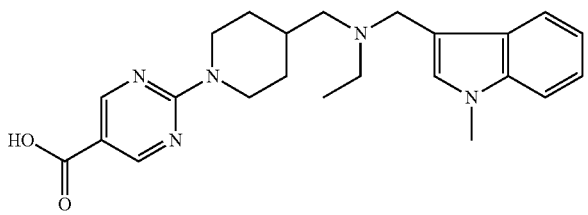 [SMILES: CCN(Cc1cn(C)c2ccccc12)CC1CCN(c2ncc(C(=O)O)cn2)CC1]
•Na; Interm. 153; Ex. [A7]
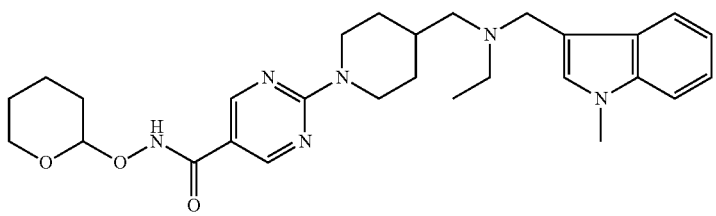 [SMILES: CCN(Cc1cn(C)c2ccccc12)CC1CCN(c2ncc(C(=O)NOC3CCCCO3)cn2)CC1]
Interm. 154; Ex. [A7]

TABLE F-1-continued
(intermediates)
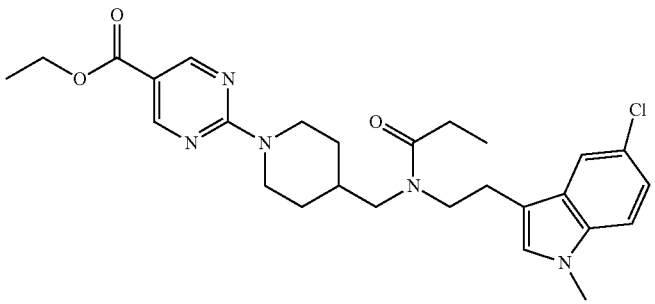 [SMILES: CCOC(=O)c1cnc(N2CCC(CN(CCc3cn(C)c4ccc(Cl)cc34)C(=O)CC)CC2)nc1]
Interm. 155; Ex. [A9]
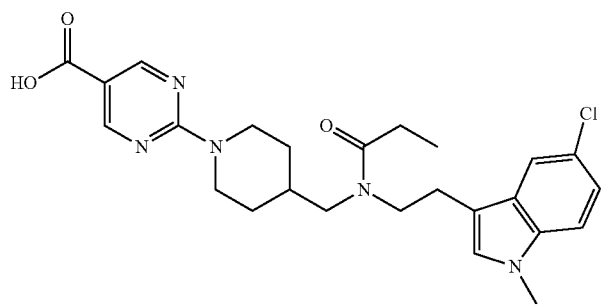 [SMILES: CCC(=O)N(CCc1cn(C)c2ccc(Cl)cc12)CC1CCN(c2ncc(C(=O)O)cn2)CC1]
•Na; Interm. 156; Ex. [A9]; mp. >260° C.
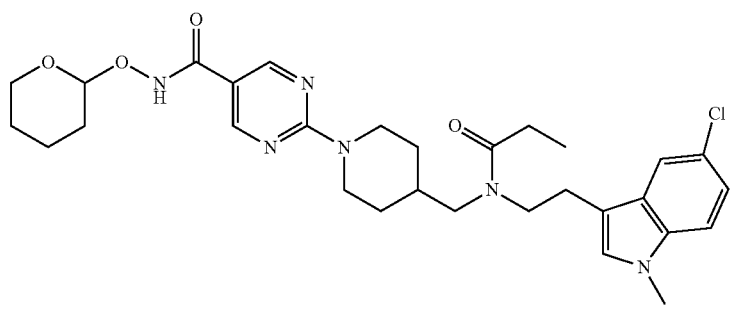 [SMILES: CCC(=O)N(CCc1cn(C)c2ccc(Cl)cc12)CC1CCN(c2ncc(C(=O)NOC3CCCCO3)cn2)CC1]
Interm. 157; Ex. [A9]
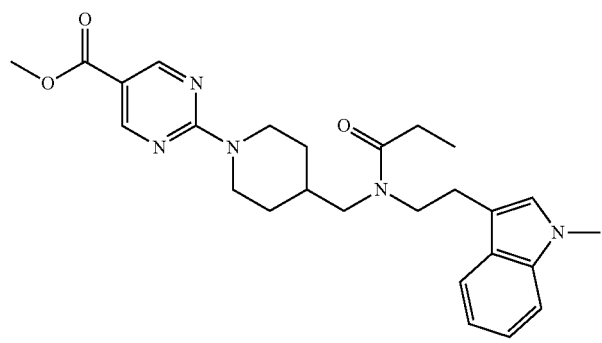
Interm. 158; Ex. [A9]

TABLE F-1-continued
(intermediates)
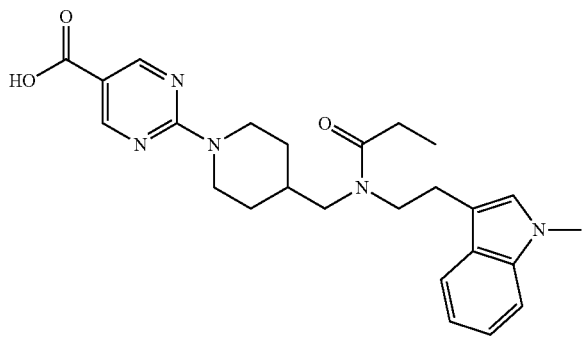 [SMILES: CCC(=O)N(CCc1cn(C)c2ccccc12)CC1CCN(c2ncc(C(=O)O)cn2)CC1]
•Na; Interm. 159; Ex. [A9]
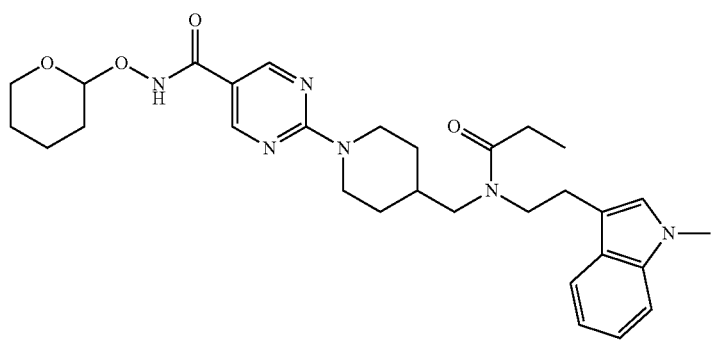 [SMILES: CCC(=O)N(CCc1cn(C)c2ccccc12)CC1CCN(c2ncc(C(=O)NOC3CCCCO3)cn2)CC1]
Interm.160 ; Ex. [A9]
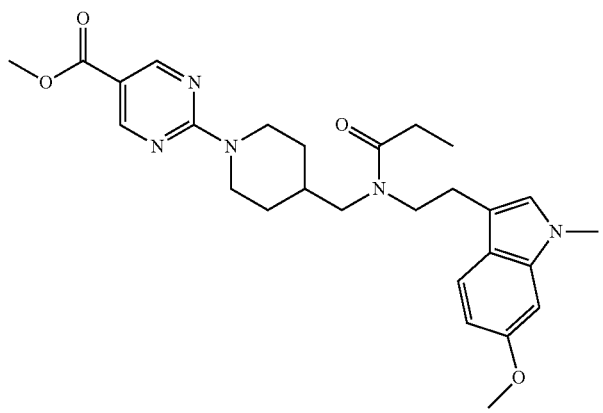
Interm. 161; Ex. [A9]
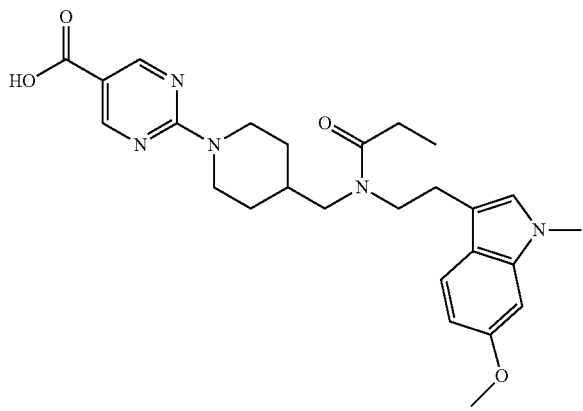 [SMILES: CCC(=O)N(CCc1cn(C)c2cc(OC)ccc12)CC1CCN(c2ncc(C(=O)O)cn2)CC1]
•Na; Interm. 162; Ex. [A9]; mp. >260° C.

TABLE F-1-continued
(intermediates)
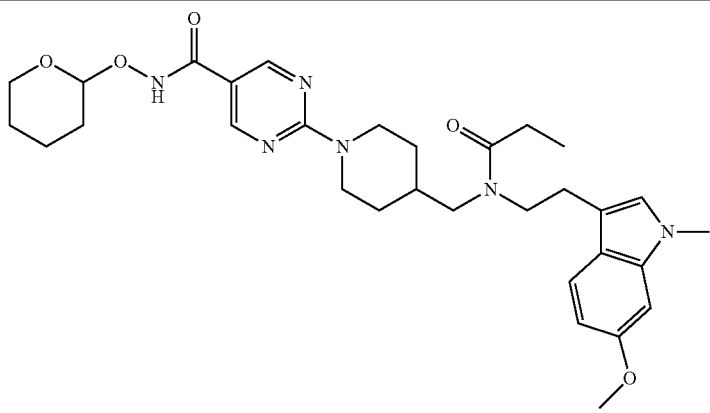
Interm. 163; Ex. [A9]
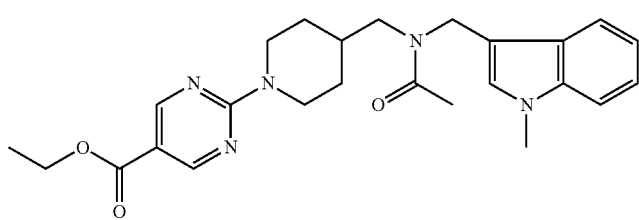 [SMILES: CCOC(=O)c1cnc(N2CCC(CN(Cc3cn(C)c4ccccc34)C(C)=O)CC2)nc1]
Interm. 164; Ex. [A9]
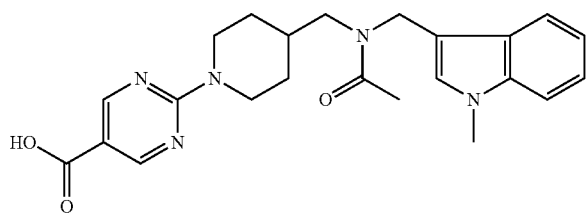 [SMILES: CC(=O)N(Cc1cn(C)c2ccccc12)CC1CCN(c2ncc(C(=O)O)cn2)CC1]
•Na; Interm. 165; Ex. [A9]
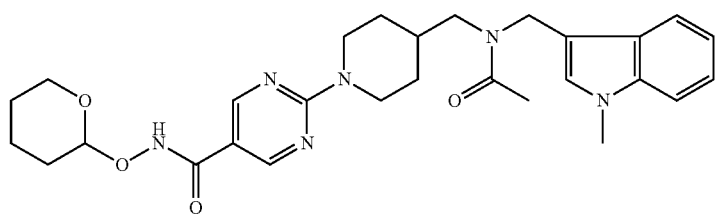 [SMILES: CC(=O)N(Cc1cn(C)c2ccccc12)CC1CCN(c2ncc(C(=O)NOC3CCCCO3)cn2)CC1]
Interm. 166; Ex. [A9]
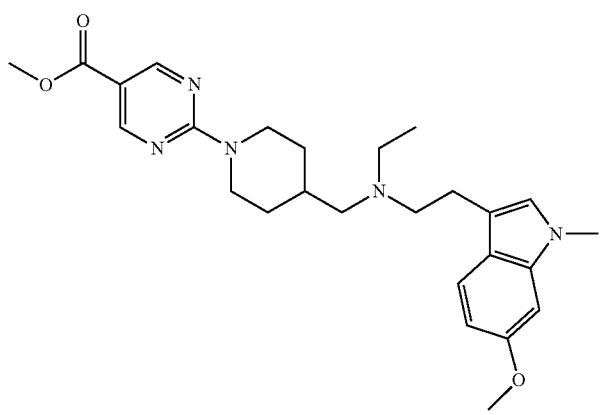
Interm. 167 Ex. [A12];

TABLE F-1-continued
(intermediates)
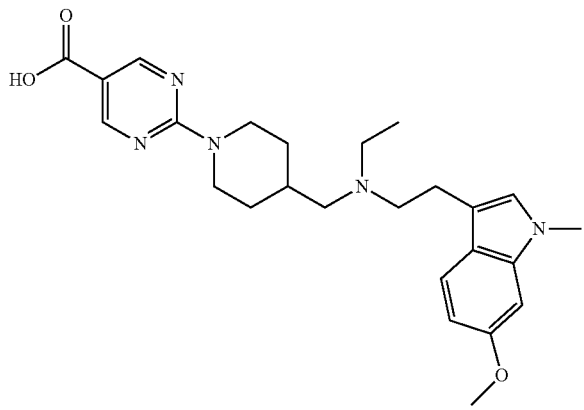 [SMILES: CCN(CCc1cn(C)c2cc(OC)ccc12)CC1CCN(c2ncc(C(=O)O)cn2)CC1]
•Na; Interm. 168; Ex. [A12]; mp. >260° C.
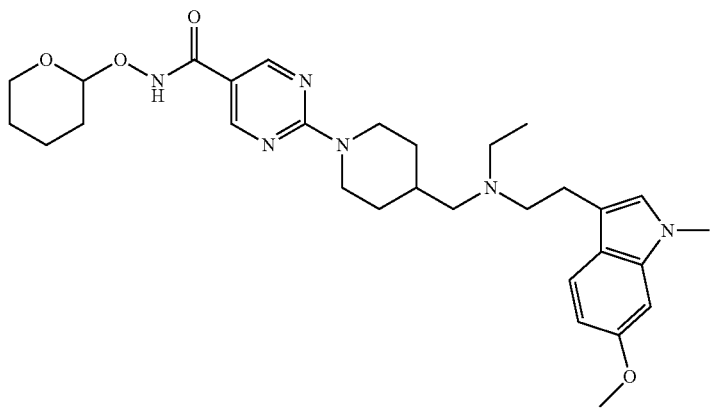 [SMILES: CCN(CCc1cn(C)c2cc(OC)ccc12)CC1CCN(c2ncc(C(=O)NOC3CCCCO3)cn2)CC1]
Interm. 169; Ex. [Al2]; mp. 80° C.
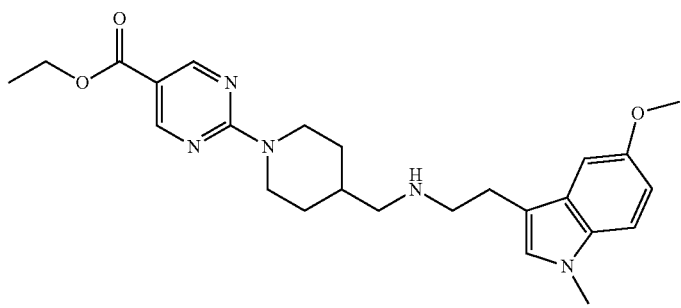 [SMILES: CCOC(=O)c1cnc(N2CCC(CNCCc3cn(C)c4ccc(OC)cc34)CC2)nc1]
Interm. 170; Ex. [A13]
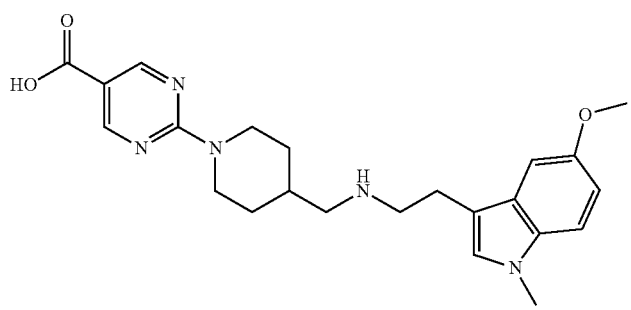 [SMILES: COc1ccc2c(c1)c(CCNCC1CCN(c3ncc(C(=O)O)cn3)CC1)cn2C]
•Na; Interm. 171; Ex. [A13]

TABLE F-1-continued
(intermediates)
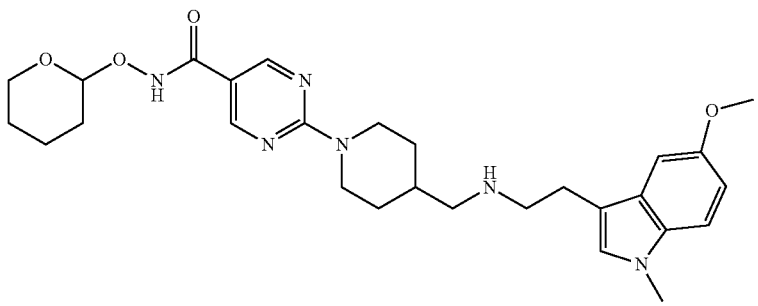 [SMILES: COc1ccc2c(c1)c(CCNCC1CCN(c3ncc(C(=O)NOC4CCCCO4)cn3)CC1)cn2C]
Interm. 172; Ex. [A13]
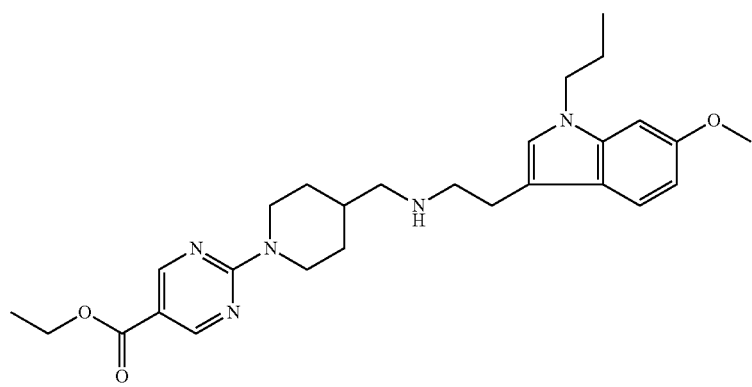 [SMILES: CCCn1cc(CCNCC2CCN(c3ncc(C(=O)OCC)cn3)CC2)c2ccc(OC)cc21]
Interm. 173; Ex. [A13]; mp. 173° C.
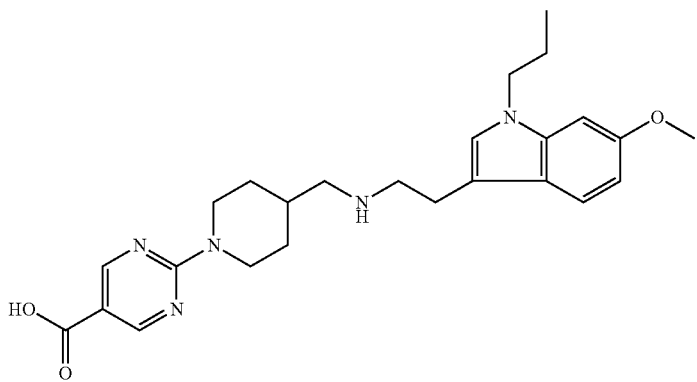 [SMILES: CCCn1cc(CCNCC2CCN(c3ncc(C(=O)O)cn3)CC2)c2ccc(OC)cc21]
•Na; Interm. 174; Ex. [A13]; mp. >260° C.
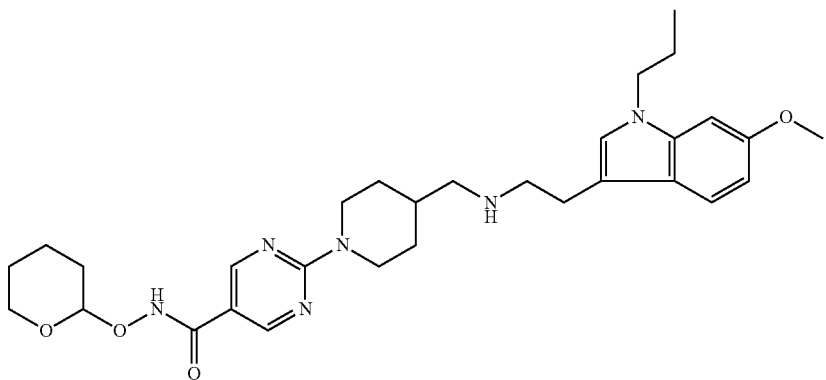 [SMILES: CCCn1cc(CCNCC2CCN(c3ncc(C(=O)NOC4CCCCO4)cn3)CC2)c2ccc(OC)cc21]
Interm. 175; Ex. [A13]

TABLE F-1-continued (intermediates)

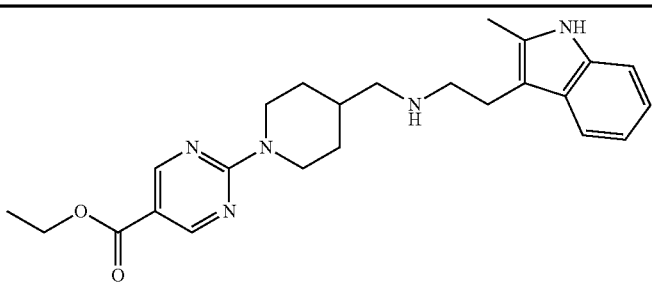

Interm. 176; Ex. [A17]

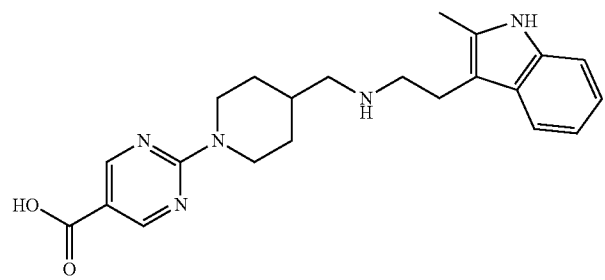 [SMILES: Cc1[nH]c2ccccc2c1CCNCC1CCN(c2ncc(C(=O)O)cn2)CC1]

•Na; Interm. 177; Ex. [A17]; mp. >260° C.

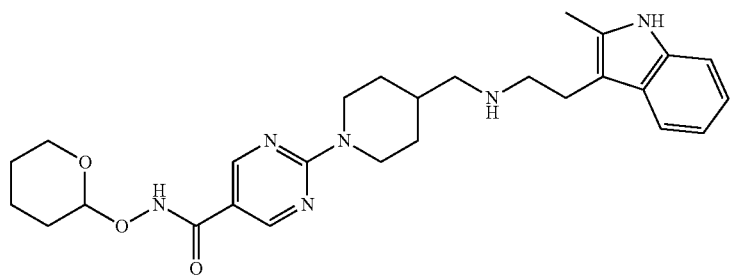 [SMILES: Cc1[nH]c2ccccc2c1CCNCC1CCN(c2ncc(C(=O)NOC3CCCCO3)cn2)CC1]

Interm.178 ; Ex. [A17]

B. Preparation of the Final Compounds

EXAMPLE B1

Preparation of compound 1a

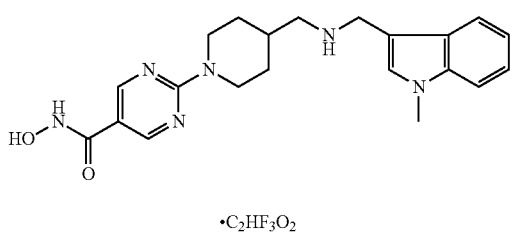

•C₂HF₃O₂

TFA (2 ml) was added to a mixture of intermediate 3 (0.0006 mol) in MeOH (40 ml). The mixture was stirred at room temperature for 30 hours. The solvent was evaporated. The residue was crystallized from EtOAc/diethyl ether. The precipitate was filtered off and dried, yielding 0.31 g (86%) of compound 1a, melting point 130° C.

Alternative Synthesis for Compound 1

Preparation of compound 1b

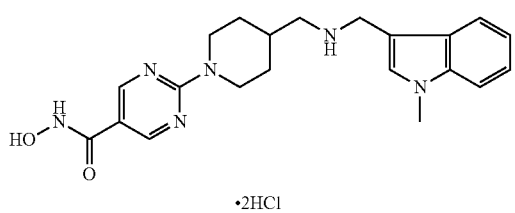 [SMILES: Cn1cc(CNCC2CCN(c3ncc(C(=O)NO)cn3)CC2)c2ccccc21 ; "·2HCl"]

•2HCl

Hydroxylamine (50% in water, 7.5 ml) and then NaOH 1N (15 ml) were added at 10° C. to a mixture of intermediate 1 (0.0098 mol) in MeOH (10 ml). The mixture was stirred at room temperature for 24 hours. The mixture was acidified to pH5-6 by adding a solution of HCl 1N. The precipitate was filtered off washed with diethylether and dried. The residue was (4.5 g) was purified by column chromatography over silica gel LiChroprep® NH2 (25-40 µm) (eluent: DCM/ MeOH/H₂O 90/10/1). The pure fractions were collected and the solvent was evaporated, yielding 3.1 g (80%). The HCl salt was prepared on a fraction (0.5 g) in EtOH and the precipitate was filtered off washed with diethylether and dried yielding 0.43 g of compound 1b, melting point 220° C.

EXAMPLE B2

Preparation of compound 2

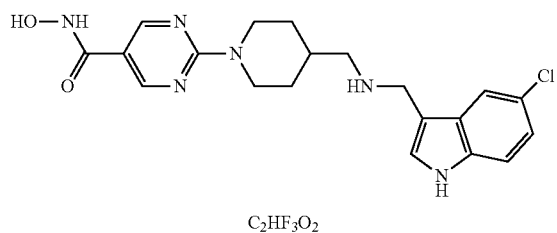 [SMILES: O=C(NO)c1cnc(N2CCC(CNCc3c[nH]c4ccc(Cl)cc34)CC2)nc1 ; "C2HF3O2"]

TFA (0.5 ml) was added to a mixture of intermediate 7 (0.0001 mol) in MeOH (10 ml) and the mixture was stirred at room temperature for 24 hours. The solvent was evaporated. The residue was crystallized from acetonitrile/diethyl ether. The precipitate was filtered off and dried, yielding 0.036 g (50%) of compound 2, melting point 205° C.

EXAMPLE B3

Preparation of compound 3

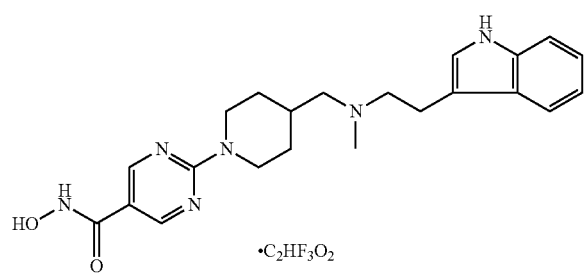

TFA (5 ml) was added at room temperature to a mixture of intermediate 12 (0.0014 mol) in MeOH (100 ml). The mixture was stirred at room temperature for 48 hours. The solvent was evaporated till dryness. The residue was crystallized from EtOAc/diethyl ether. The precipitate was filtered off and dried, yielding 0.545 g (74%) of compound 3, melting point 121° C.

EXAMPLE B4

Preparation of compound 4

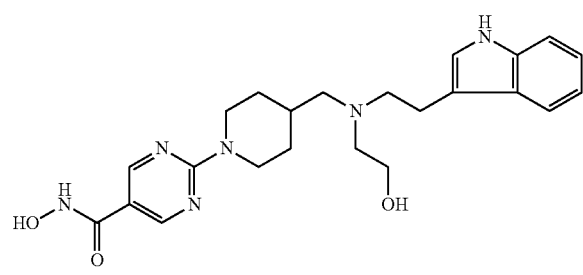

TFA (0.5 ml) was added to a mixture of intermediate 17 (0.0009 mol) in MeOH (80 ml). The mixture was stirred at room temperature for 4 days. The solvent was evaporated. The residue was crystallized from diethyl ether. The precipitate was filtered off and dried, yielding 0.19 g (32%) of compound 4, melting point 103° C.

EXAMPLE B5

Preparation of compound 18

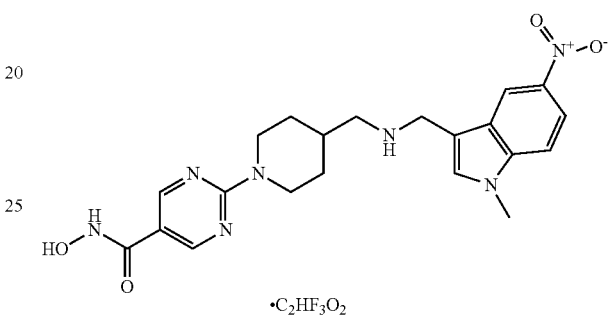

A mixture of intermediate 48 (0.0002 mol) in TFA (0.75 ml) and MeOH (15 ml) was stirred at room temperature for 24 hours. The solvent was evaporated. The residue was crystallized from diethyl ether. The precipitate was filtered off and dried, yielding 0.071 g (59%) of compound 18.

EXAMPLE B6

Preparation of compound 19

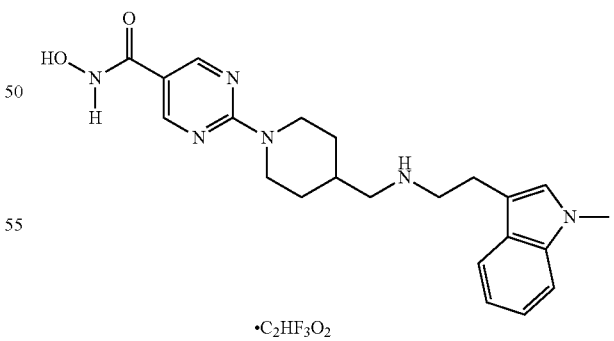

A mixture of intermediate 53 (0.0003 mol) in TFA (1 ml) and MeOH (20 ml) was stirred at room temperature for 24 hours. The solvent was evaporated till dryness. The residue was crystallized from MeOH/CH$_3$CN/diethyl ether. The precipitate was filtered off and dried, yielding 0.133 g (80%) of compound 19, melting point 174° C.

EXAMPLE B7

Preparation of compound 20

A mixture of intermediate 57 (0.00005 mol) in TFA (0.25 ml) and MeOH (10 ml) was stirred at room temperature for 24 hours. The solvent was evaporated. The residue (0.04 g) was crystallized from $CH_3CN$/diethyl ether. The precipitate was filtered off and dried. The residue (0.04 g) was purified by column chromatography over silica gel LiChroprep® $NH_2$ (25-40 μm) (eluent: DCM/MeOH/$H_2O$ 80/20/2). The pure fractions were collected and the solvent was evaporated, yielding 0.02 g (80%) of compound 20, melting point 90° C.

EXAMPLE B8

Preparation of compound 21

A mixture of intermediate 60 (0.0001 mol) in TFA (0.5 ml) and MeOH (10 ml) was stirred at room temperature overnight. The solvent was evaporated. The residue (0.15 g) was purified by column chromatography over silica gel LiChroprep® $NH_2$ (25-40 μm) (eluent: DCM/MeOH/$H_2O$ 80/20/2). The pure fractions were collected and the solvent was evaporated, yielding 0.064 g (78%) of compound 21, melting point 83° C.

EXAMPLE B9

Preparation of compound 22

A mixture of intermediate 65 (0.002 mol) in TFA (6 ml) and MeOH (120 ml) was stirred at room temperature for 24 hours. The solvent was evaporated till dryness. The residue was crystallized from $CH_3CN$/MeOH/diethyl ether. The precipitate was filtered off and dried, yielding 0.9 g (87%) of compound 22, melting point 183° C.

EXAMPLE B10

Preparation of compound 23

A mixture of intermediate 72 (0.0001 mol) in TFA (0.5 ml) and MeOH (10 ml) was stirred at room temperature for 48 hours. The solvent was evaporated. The residue was crystallized from diethyl ether. The precipitate was filtered off and dried, yielding 0.059 g (59%) of compound 23, melting point 182° C.

EXAMPLE B11

Preparation of compound 24

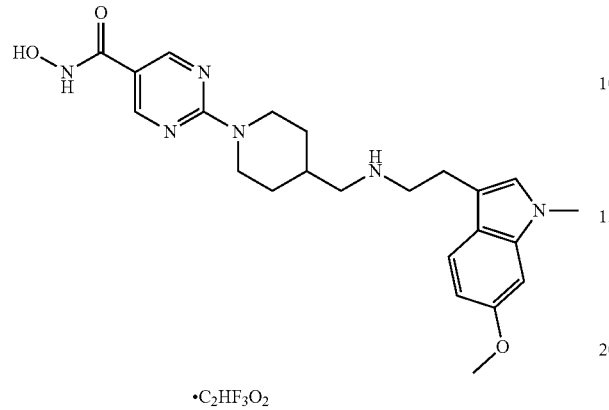

•C₂HF₃O₂

A mixture of intermediate 75 (0.0003 mol) in TFA (1 ml) and MeOH (20 ml) was stirred at room temperature for 24 hours. The solvent was evaporated till dryness. The residue was crystallized from MeOH/CH₃CN/diethyl ether. The precipitate was filtered off and dried, yielding 0.147 g (78%) of compound 24, melting point 160° C.

EXAMPLE B12

Preparation of compound 25

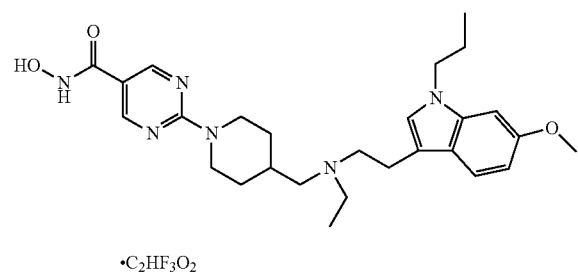 [SMILES: CCCn1cc(CCN(CC)CC2CCN(c3ncc(C(=O)NO)cn3)CC2)c2ccc(OC)cc21 ; "·C2HF3O2"]

•C₂HF₃O₂

A mixture of intermediate 82 (0.0009 mol) in TFA (2.5 ml) and MeOH (56 ml) was stirred at room temperature for 24 hours. The solvent was evaporated till dryness. The residue was purified by column chromatography over silica gel (25-40 μm) (eluent: DCM/MeOH/H₂O 90/10/1). The pure fractions were collected and the solvent was evaporated. The residue was crystallized from DIPE. The precipitate was filtered off and dried, yielding 0.286 g (53%) of compound 25, melting point 80° C.

EXAMPLE B13

Preparation of compound 26

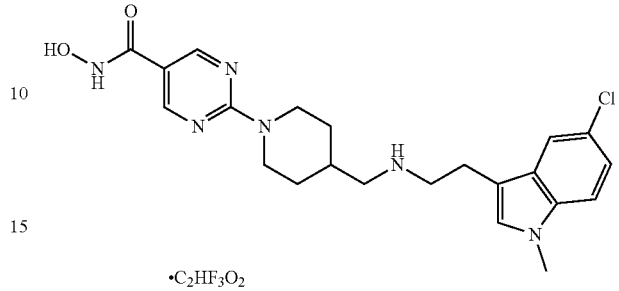

•C₂HF₃O₂

A mixture of intermediate 84 (0.0012 mol) in TFA (3 ml) and MeOH (60 ml) was stirred at room temperature for 24 hours. The solvent was evaporated till dryness. The residue was crystallized from DCM/MeOH. The precipitate was filtered off, washed with diethyl ether and dried, yielding 0.322 g (50%) of compound 26, melting point 188° C.

EXAMPLE B14

Preparation of compound 27

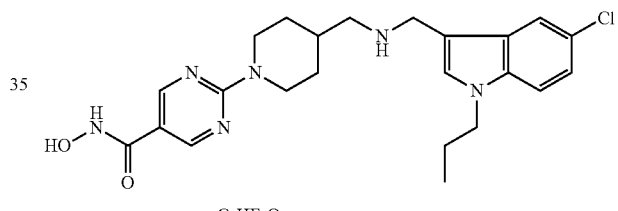

•C₂HF₃O₂

A mixture of intermediate 89 (0.001 mol) in TFA (2.5 ml) and MeOH (50 ml) was stirred at room temperature for 24 hours, then evaporated till dryness. The residue was crystallized from MeOH/CH₃CN/diethyl ether. The precipitate was filtered off, washed with water and dried, yielding 0.33 g (55%) of compound 27, melting point 171° C.

EXAMPLE B15

Preparation of compound 28

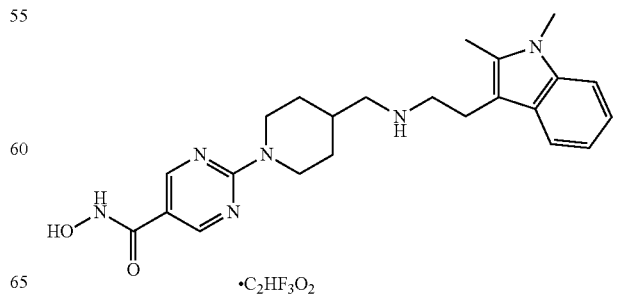

•C₂HF₃O₂

A mixture of intermediate 93 (0.00007 mol) in TFA (0.2 ml) and MeOH (4 ml) was stirred at room temperature for 3 days, then evaporated till dryness, yielding 0.041 g (100%) of compound 28, melting point 80° C.

Table F-2 lists the compounds that were prepared according to one of the above Examples. The following abbreviations were used in the tables: .C₂HF₃O₂ stands for the trifluoroacetate salt, mp. stands for melting point.

TABLE F-2

(final compounds)

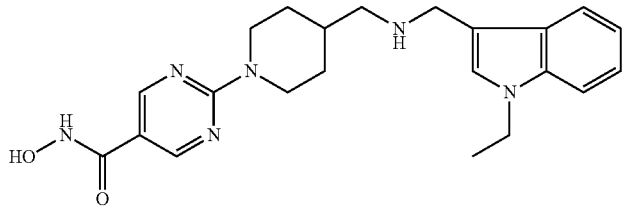 [SMILES: CCn1cc(CNCC2CCN(c3ncc(C(=O)NO)cn3)CC2)c2ccccc21]

C₂HF₃O₂, Co. No. 1a; Ex. [B1]; mp. 163° C.

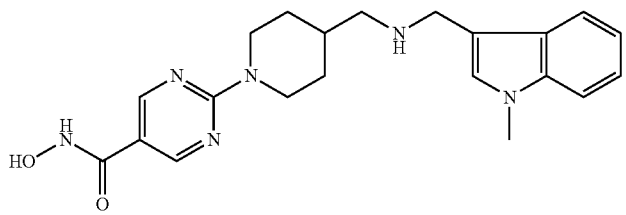 [SMILES: Cn1cc(CNCC2CCN(c3ncc(C(=O)NO)cn3)CC2)c2ccccc21]

•HCl; Co. No. 1b; Ex. [B1]; mp. 220° C.

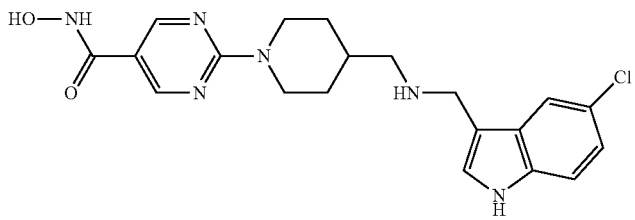 [SMILES: O=C(NO)c1cnc(N2CCC(CNCc3c[nH]c4ccc(Cl)cc34)CC2)nc1]

C₂HF₃O₂; Co. No. 2; Ex. [B2]; mp. 205° C.

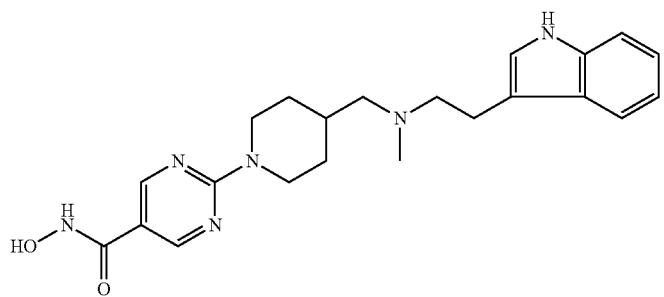 [SMILES: CN(CCc1c[nH]c2ccccc12)CC1CCN(c2ncc(C(=O)NO)cn2)CC1]

Co. No. 3; Ex. [B3]; mp. 121° C.

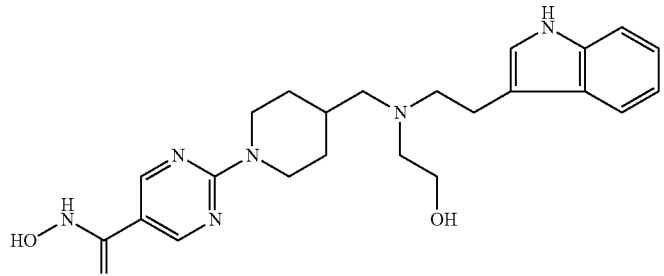

•C₂HF₃O₂, Co. No. 4; Ex. [B4]; mp. 103° C.

TABLE F-2-continued
(final compounds)
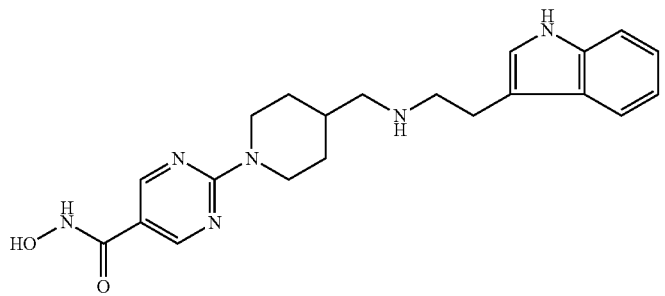 [SMILES: O=C(NO)c1cnc(N2CCC(CNCCc3c[nH]c4ccccc34)CC2)nc1]
•$C_2HF_3O_2$;Co. No. 5; Ex. [B1]; mp. 120° C.
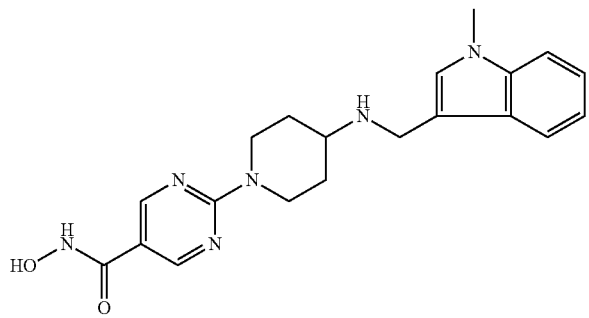 [SMILES: Cn1cc(CNC2CCN(c3ncc(C(=O)NO)cn3)CC2)c2ccccc21]
•$C_2HF_3O_2$; Co. No. 6; Ex. [B1]; mp. 132° C.
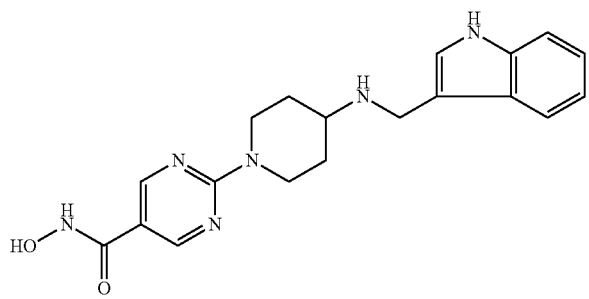 [SMILES: O=C(NO)c1cnc(N2CCC(NCc3c[nH]c4ccccc34)CC2)nc1]
$C_2HF_3O_2$; Co. No. 7; Ex. [B1] mp. 136° C.
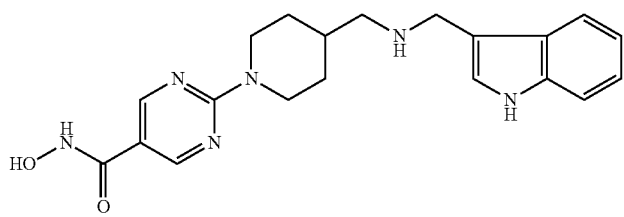 [SMILES: O=C(NO)c1cnc(N2CCC(CNCc3c[nH]c4ccccc34)CC2)nc1]
$C_2HF_3O_2$;Co. No. 8; Ex. [B1]; mp. 110° C.
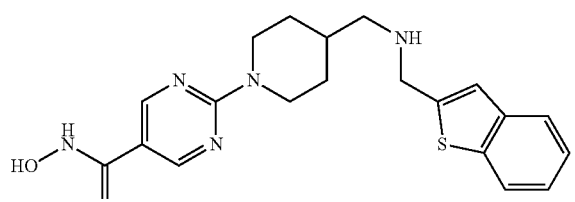
$C_2HF_3O_2$; Co. No. 9; Ex. [B1]; mp. 217° C.

TABLE F-2-continued
(final compounds)
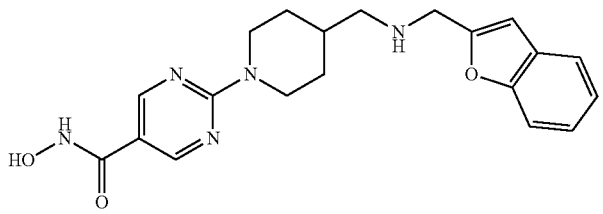 [SMILES: O=C(NO)c1cnc(N2CCC(CNCc3cc4ccccc4o3)CC2)nc1]
C₂HF₃O₂; Co. No. 10; Ex. [B1]; mp. 192° C.
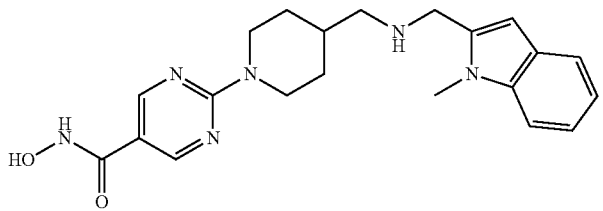 [SMILES: Cn1c(CNCC2CCN(c3ncc(C(=O)NO)cn3)CC2)cc2ccccc21]
C₂HF₃O₂; Co. No. 11; Ex. [B1]; mp. 186° C.
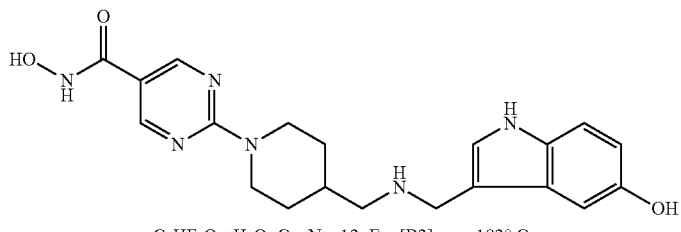
C₂HF₃O₂•H₂O; Co. No. 12; Ex. [B2]; mp. 192° C.
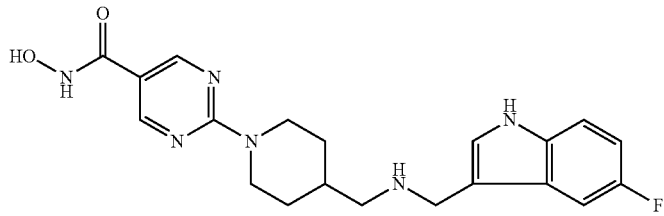 [SMILES: O=C(NO)c1cnc(N2CCC(CNCc3c[nH]c4ccc(F)cc34)CC2)nc1]
C₂HF₃O₂; Co. No. 13; Ex. [B2]; mp. 202° C.
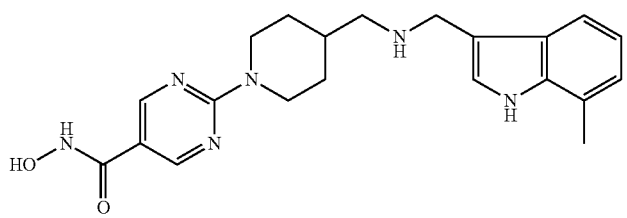
C₂HF₃O₂; Co. No. 14; Ex. [B2]; mp. 145° C.
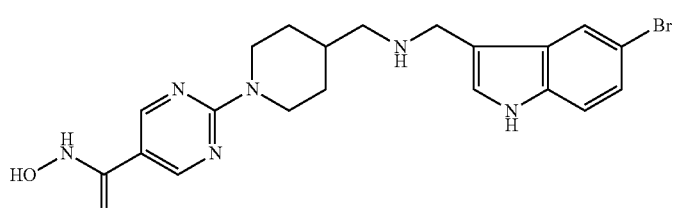
C₂HF₃O₂; Co. No. 15; Ex. [B2]; mp. >260° C.

TABLE F-2-continued
(final compounds)
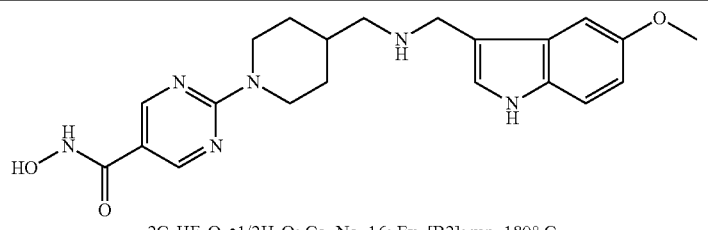
2C$_2$HF$_3$O$_2$•1/2H$_2$O; Co. No. 16; Ex. [B2]; mp. 180° C.
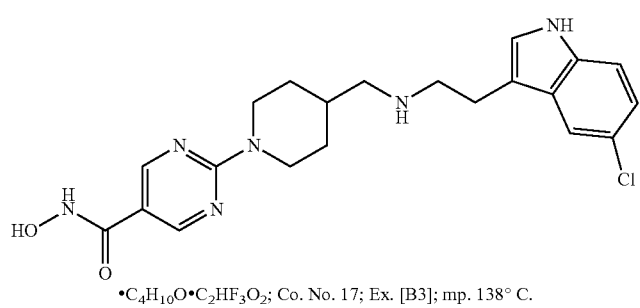
•C$_4$H$_{10}$O•C$_2$HF$_3$O$_2$; Co. No. 17; Ex. [B3]; mp. 138° C.
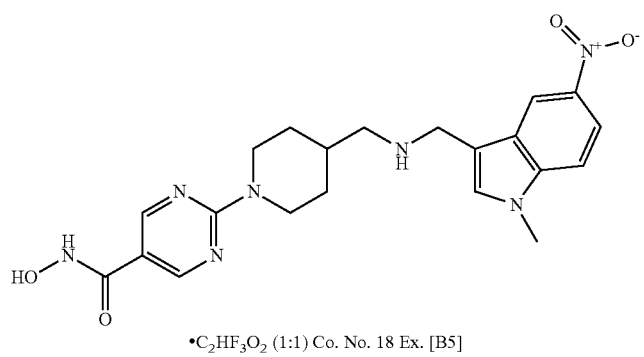
•C$_2$HF$_3$O$_2$ (1:1) Co. No. 18 Ex. [B5]
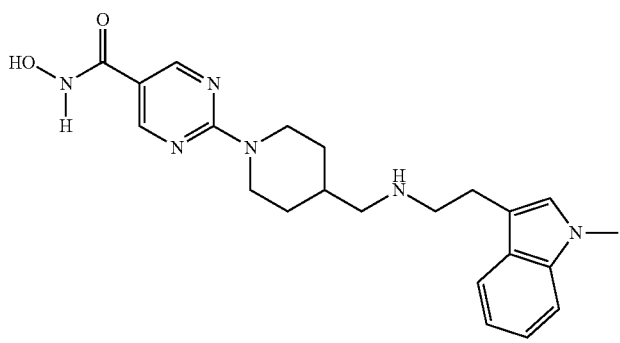 [SMILES: Cn1cc(CCNCC2CCN(c3ncc(C(=O)NO)cn3)CC2)c2ccccc21]
•C$_2$HF$_3$O$_2$ (1:1); Co. No. 19; Ex. [B6]; mp. 174° C.
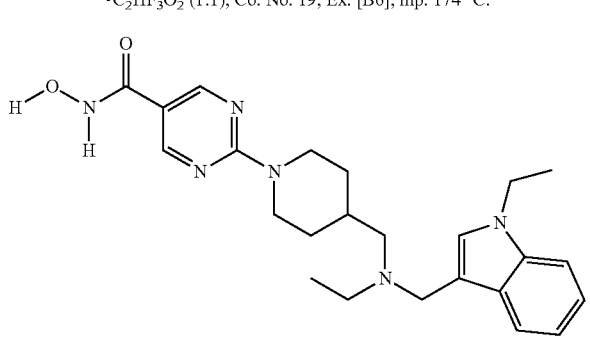
Co. No. 20; Ex. [B7]; mp. 90° C.

TABLE F-2-continued
(final compounds)
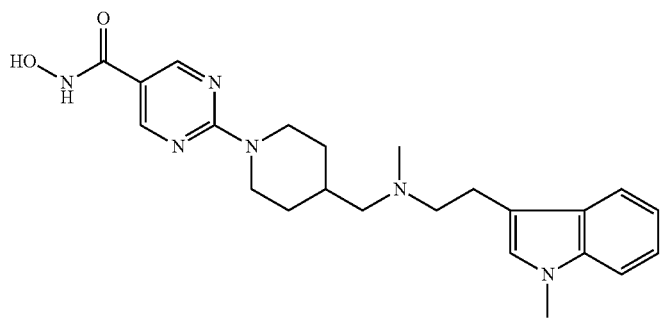 [SMILES: CN(CCc1cn(C)c2ccccc12)CC1CCN(c2ncc(C(=O)NO)cn2)CC1]
Co. No. 21; Ex. [B8]; mp. 83° C.
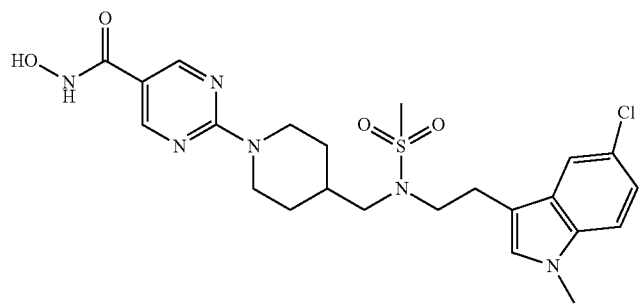 [SMILES: Cn1cc(CCN(CC2CCN(c3ncc(C(=O)NO)cn3)CC2)S(C)(=O)=O)c2cc(Cl)ccc21]
Co. No. 22; Ex. [B9]; mp. 183° C.
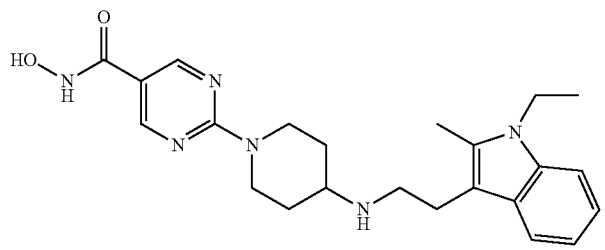 [SMILES: CCn1c(C)c(CCNC2CCN(c3ncc(C(=O)NO)cn3)CC2)c2ccccc21]
•C₂HF₃O₂ (1:1); Co. No. 23; Ex. [B10]; mp. 182° C.
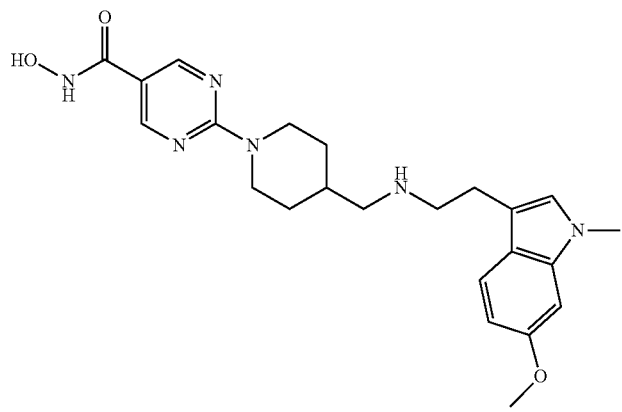 [SMILES: COc1ccc2c(CCNCC3CCN(c4ncc(C(=O)NO)cn4)CC3)cn(C)c2c1]
•C₂HF₃O₂ (1:1); Co. No. 24; Ex. [B11]; mp. 160° C.

TABLE F-2-continued
(final compounds)
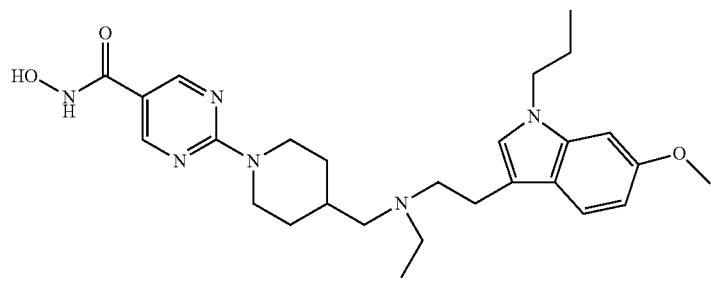 [SMILES: CCCn1cc(CCN(CC)CC2CCN(c3ncc(C(=O)NO)cn3)CC2)c2ccc(OC)cc21]
•C₂HF₃O₂ (1:1); Co. No. 25; Ex. [B12]; mp. 80° C.
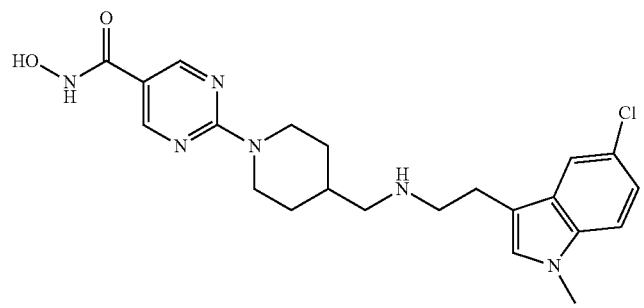 [SMILES: Cn1cc(CCNCC2CCN(c3ncc(C(=O)NO)cn3)CC2)c2cc(Cl)ccc21]
•C₂HF₃O₂ (1:1); Co. No. 26; Ex. [B13]; mp. 188° C.
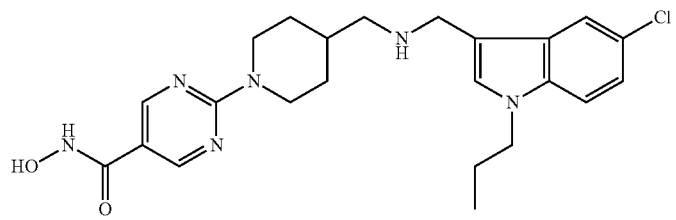 [SMILES: CCCn1cc(CNCC2CCN(c3ncc(C(=O)NO)cn3)CC2)c2cc(Cl)ccc21]
•C₂HF₃O₂ (1:1); Co. No. 27; Ex. [B14]; mp. 171° C.
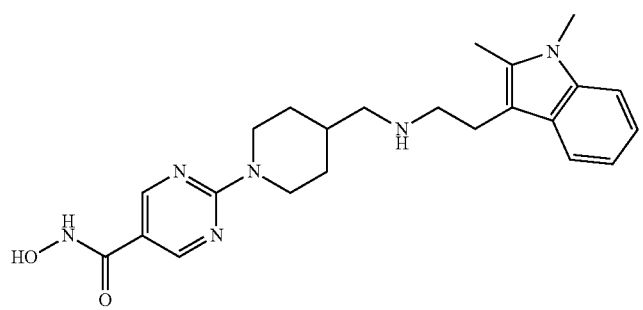 [SMILES: Cc1c(CCNCC2CCN(c3ncc(C(=O)NO)cn3)CC2)c2ccccc2n1C]
•C₂HF₃O₂ (1:1); Co. No. 28; Ex. [B15]; mp. 80° C.

TABLE F-2-continued
(final compounds)
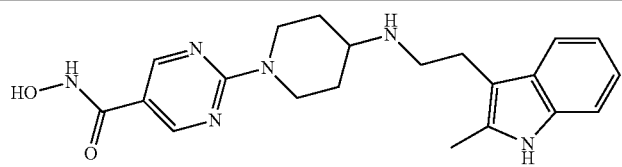 [SMILES: Cc1[nH]c2ccccc2c1CCNC1CCN(c2ncc(C(=O)NO)cn2)CC1]
•$C_2HF_3O_2$ (1:1); Co. No. 29; Ex. [B1]; mp. 173° C.
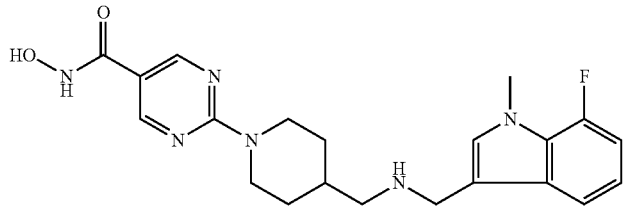 [SMILES: Cn1cc(CNCC2CCN(c3ncc(C(=O)NO)cn3)CC2)c2cccc(F)c21]
•$C_2HF_3O_2$ (1:1); Co. No.30 ; Ex. [B1]; mp. 197° C.
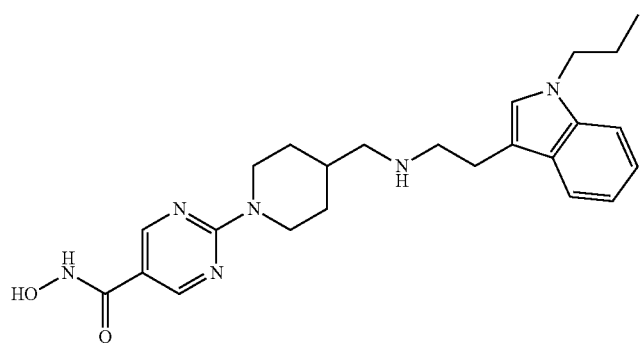 [SMILES: CCCn1cc(CCNCC2CCN(c3ncc(C(=O)NO)cn3)CC2)c2ccccc21]
•$C_2HF_3O_2$ (1:1); Co. No. 31; Ex. [B1]; mp. 160° C.
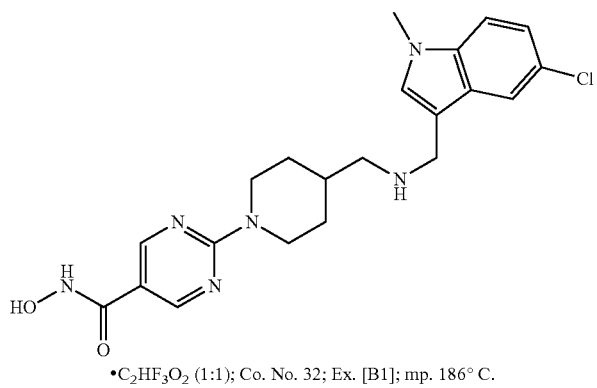
•$C_2HF_3O_2$ (1:1); Co. No. 32; Ex. [B1]; mp. 186° C.
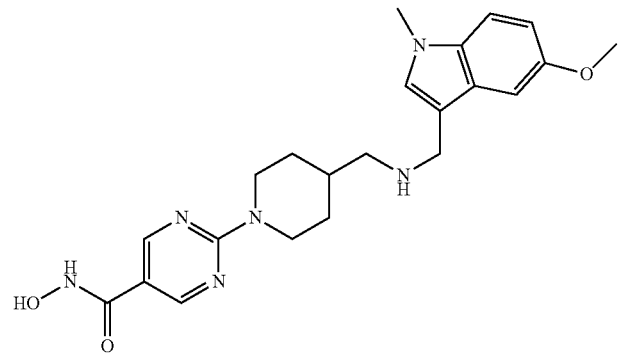 [SMILES: COc1ccc2c(c1)c(CNCC1CCN(c3ncc(C(=O)NO)cn3)CC1)cn2C]
•$C_2HF_3O_2$ (1:1); Co. No. 33; Ex. [B1]; mp. 196° C.

TABLE F-2-continued
(final compounds)
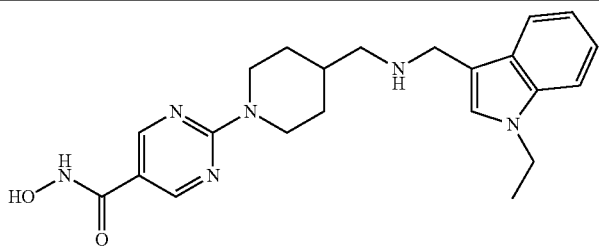
Co. No. 34; Ex. [B1]; mp. 287° C.
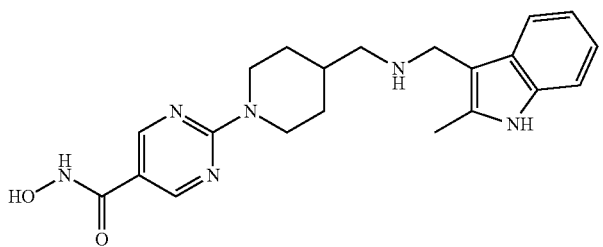 [SMILES: Cc1[nH]c2ccccc2c1CNCC1CCN(c2ncc(C(=O)NO)cn2)CC1]
Co. No. 35; Ex. [B1]
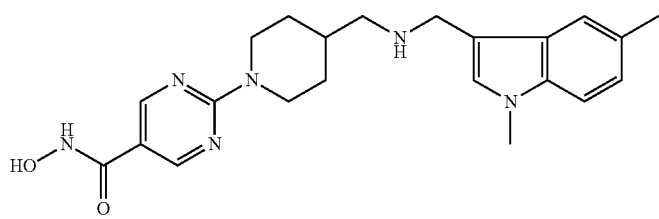 [SMILES: Cc1ccc2c(c1)c(CNCC1CCN(c3ncc(C(=O)NO)cn3)CC1)cn2C]
•$C_2HF_3O_2$ (1:1); Co. No. 36; Ex. [B2]; mp. >300° C.
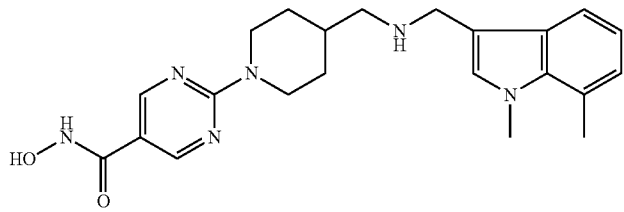 [SMILES: Cc1cccc2c(CNCC3CCN(c4ncc(C(=O)NO)cn4)CC3)cn(C)c12]
•$C_2HF_3O_2$ (1:1); Co. No. 37; Ex. [B2]; mp. 189° C.
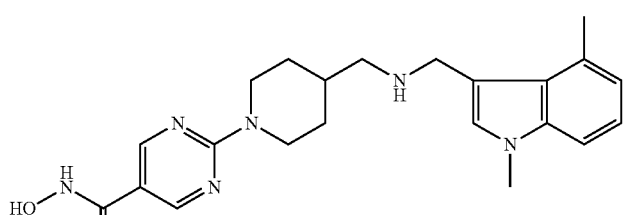
•$C_2HF_3O_2$ (1:1); Co. No. 38; Ex. [B2]; mp. 188° C.
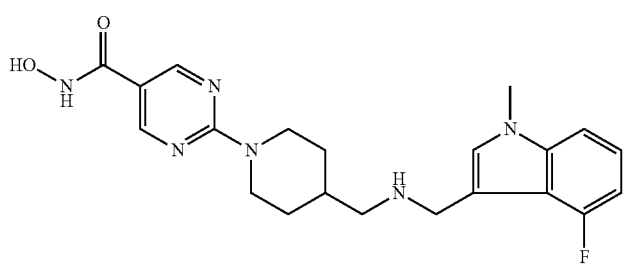 [SMILES: Cn1cc(CNCC2CCN(c3ncc(C(=O)NO)cn3)CC2)c2c(F)cccc21]
•$C_2HF_3O_2$ (1:1); Co. No. 39; Ex. [B2]; mp. 239° C.

TABLE F-2-continued
(final compounds)
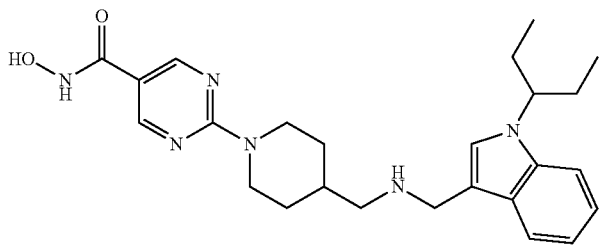 [SMILES: CCC(CC)n1cc(CNCC2CCN(c3ncc(C(=O)NO)cn3)CC2)c2ccccc21]
•$C_2HF_3O_2$ (1:1); Co. No.40; Ex. [B2]; mp. 183° C.
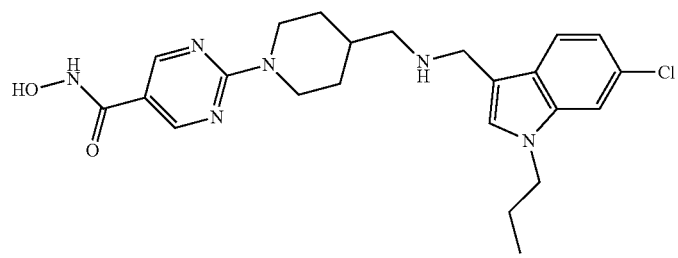 [SMILES: CCCn1cc(CNCC2CCN(c3ncc(C(=O)NO)cn3)CC2)c2ccc(Cl)cc21]
•$C_2HF_3O_2$ (1:1); Co. No. 41; Ex. [B2]; mp. 148° C.
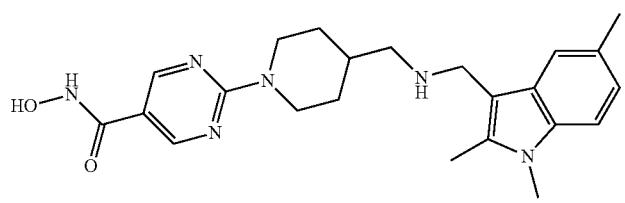 [SMILES: Cc1ccc2c(c1)c(CNCC1CCN(c3ncc(C(=O)NO)cn3)CC1)c(C)n2C]
•$C_2HF_3O_2$ (1:1); Co. No. 42; Ex. [B2]; mp. 134° C.
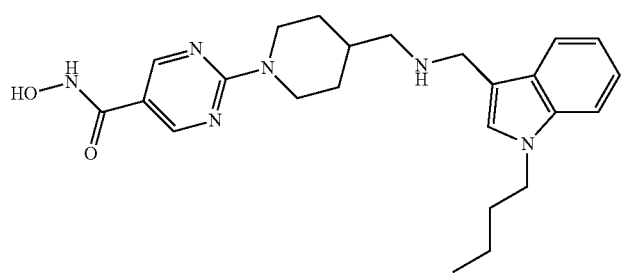 [SMILES: CCCCn1cc(CNCC2CCN(c3ncc(C(=O)NO)cn3)CC2)c2ccccc21]
•$C_2HF_3O_2$ (1:1); Co. No. 43; Ex. [B2]; mp. 143° C.
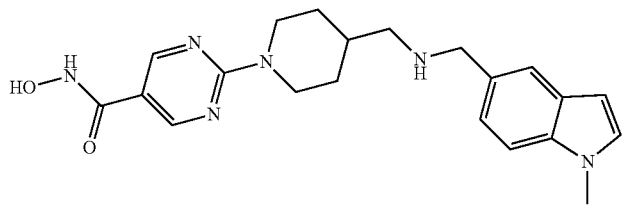 [SMILES: Cn1ccc2cc(CNCC3CCN(c4ncc(C(=O)NO)cn4)CC3)ccc21]
•$C_2HF_3O_2$ (1:1); Co. No. 44; Ex.[B2]; mp. 124° C.
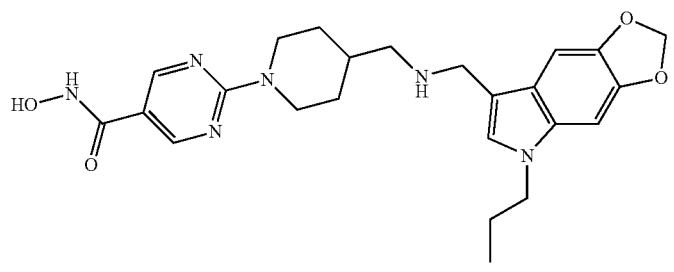 [SMILES: CCCn1cc(CNCC2CCN(c3ncc(C(=O)NO)cn3)CC2)c2cc3c(cc21)OCO3]
•$C_2HF_3O_2$ (1:1); Co. No. 45; Ex. [B2]; mp. 116° C.

TABLE F-2-continued
(final compounds)
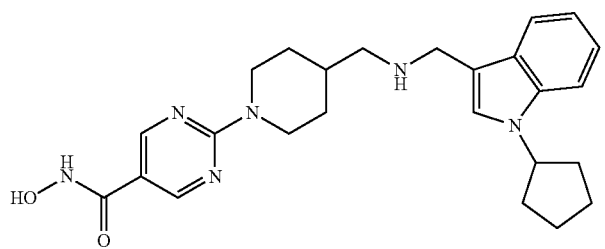 [SMILES: O=C(NO)c1cnc(N2CCC(CNCc3cn(C4CCCC4)c4ccccc34)CC2)nc1]
·C₂HF₃O₂ (1:1); Co. No. 46; Ex. [B2]; mp. 183° C.
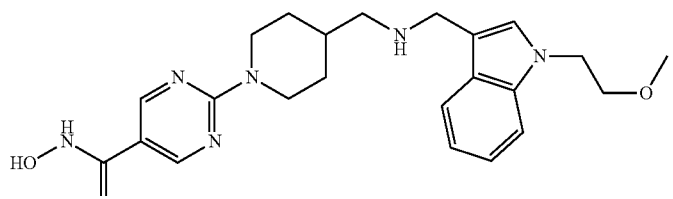
·C₂HF₃O₂ (1:1); Co. No. 47; Ex. [B2]; mp. 161° C.
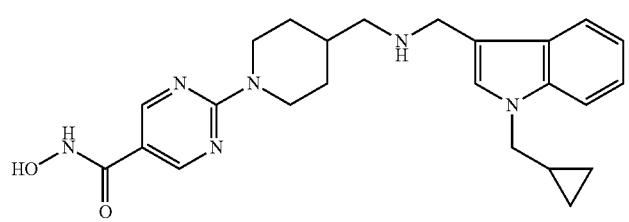 [SMILES: O=C(NO)c1cnc(N2CCC(CNCc3cn(CC4CC4)c4ccccc34)CC2)nc1]
C₂HF₃O₂ (1.1)° Co. No. 48; Ex. [B2]; mp. 181° C.
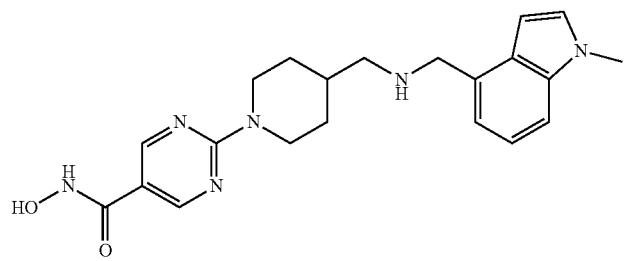 [SMILES: Cn1ccc2c(CNCC3CCN(c4ncc(C(=O)NO)cn4)CC3)cccc21]
Co. No. 49; Ex. [B2]; mp. 104° C.
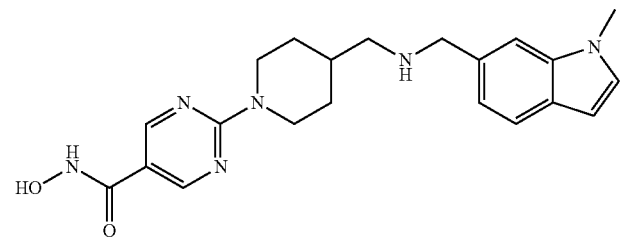 [SMILES: Cn1ccc2ccc(CNCC3CCN(c4ncc(C(=O)NO)cn4)CC3)cc21]
Co. No. 50; Ex. [B2]; mp. 114° C.
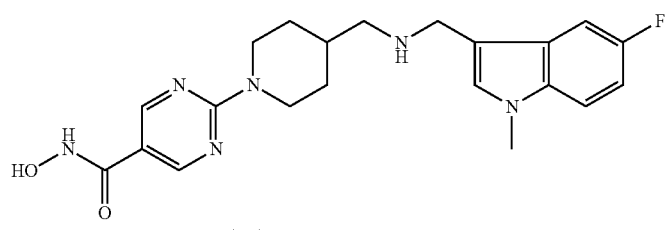 [SMILES: Cn1cc(CNCC2CCN(c3ncc(C(=O)NO)cn3)CC2)c2cc(F)ccc21]
C₂HF₃O₂ (1:1);Co. No. 51; Ex. [B2]; mp. 140° C.

TABLE F-2-continued
(final compounds)
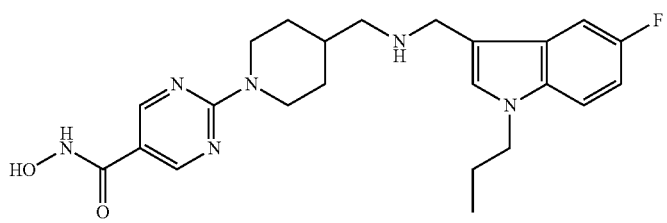 [SMILES: CCCn1cc(CNCC2CCN(c3ncc(C(=O)NO)cn3)CC2)c2cc(F)ccc21]
C₂HF₃O₂ (1:1); Co. No. 52; Ex. [B2]; mp. 114° C.
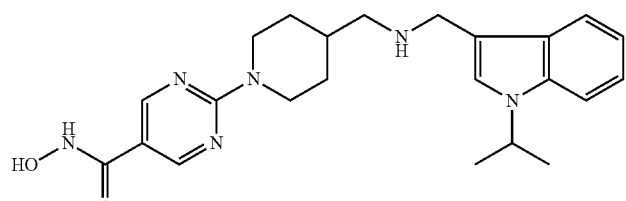
C₂HF₃O₂ (1:1); Co. No. 53; Ex. [B2]; mp. 178° C.
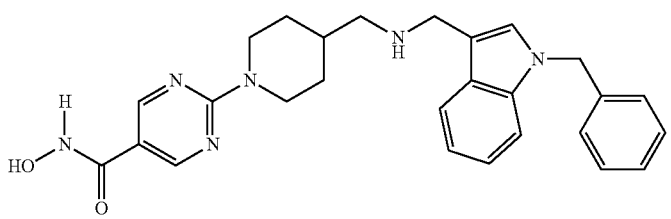 [SMILES: O=C(NO)c1cnc(N2CCC(CNCc3cn(Cc4ccccc4)c4ccccc34)CC2)nc1]
C₂HF₃O₂ (1:1); Co. No. 54; Ex. [B2]; mp. 159° C.
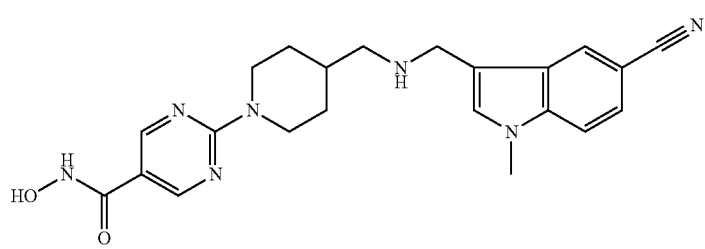 [SMILES: Cn1cc(CNCC2CCN(c3ncc(C(=O)NO)cn3)CC2)c2cc(C#N)ccc21]
C₂HF₃O₂ (1:1); Co. No. 55; Ex. [B2]; mp. 144° C.
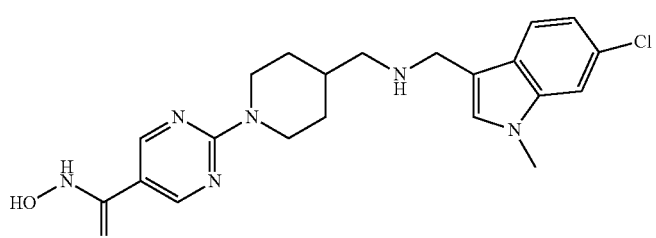
Co. No. 56; Ex. [B2]; mp. 145° C.
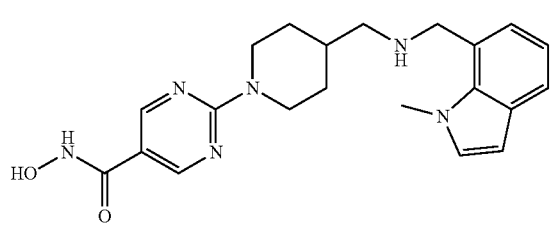 [SMILES: Cn1ccc2cccc(CNCC3CCN(c4ncc(C(=O)NO)cn4)CC3)c21]
Co. No. 57; Ex. [B2]; mp. 100° C.

TABLE F-2-continued
(final compounds)
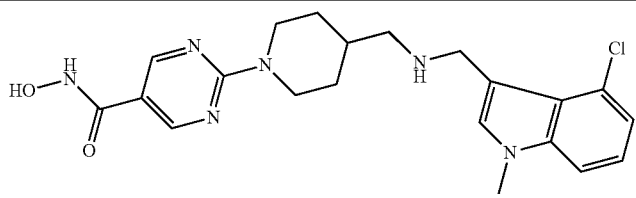
C₂HF₃O₂ (1:1); Co. No. 58; Ex. [B2]; mp. 130° C.
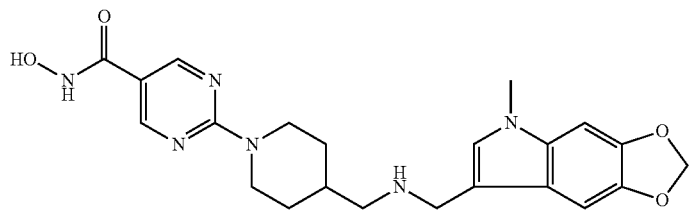 [SMILES: Cn1cc(CNCC2CCN(c3ncc(C(=O)NO)cn3)CC2)c2cc3c(cc21)OCO3]
Co. No. 59; Ex. [B2]; mp. 122° C.
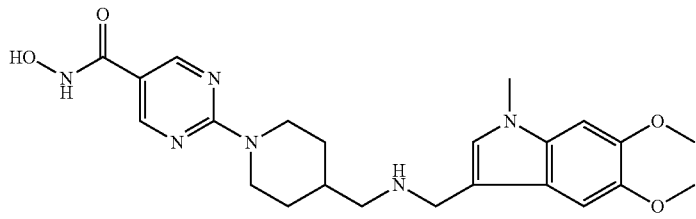 [SMILES: COc1cc2c(CNCC3CCN(c4ncc(C(=O)NO)cn4)CC3)cn(C)c2cc1OC]
Co. No. 60; Ex. [B2]; mp. 105° C.
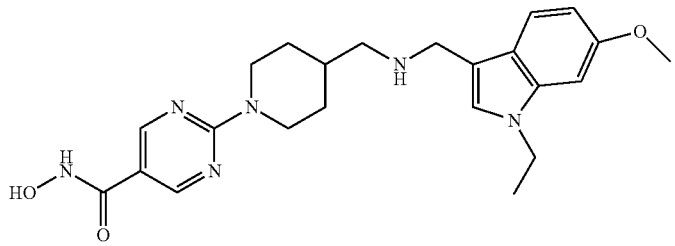 [SMILES: CCn1cc(CNCC2CCN(c3ncc(C(=O)NO)cn3)CC2)c2ccc(OC)cc21]
Co. No. 61; Ex. [B2]; mp. 117° C.
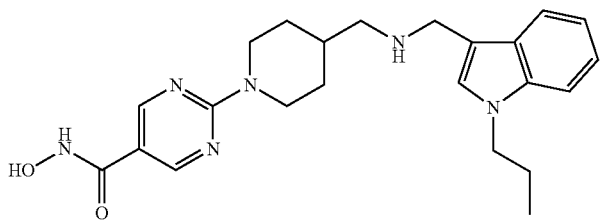 [SMILES: CCCn1cc(CNCC2CCN(c3ncc(C(=O)NO)cn3)CC2)c2ccccc21]
C₂HF₃O₂ (1:1); Co. No. 62; Ex. [B2]; mp. 162° C.
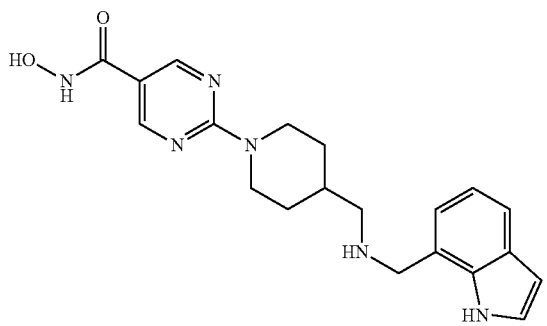 [SMILES: O=C(NO)c1cnc(N2CCC(CNCc3cccc4cc[nH]c34)CC2)nc1]
•C₂HF₃O₂ (1:1); Co. No. 63; Ex. [B2]; mp. 110° C.

TABLE F-2-continued
(final compounds)
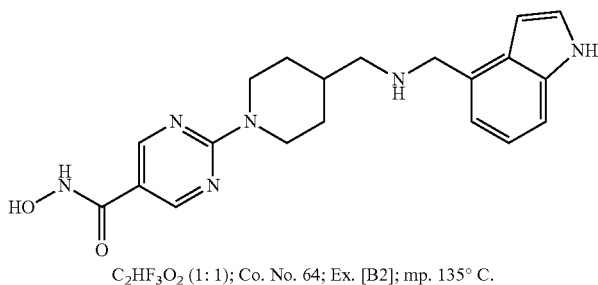
C₂HF₃O₂ (1:1); Co. No. 64; Ex. [B2]; mp. 135° C.
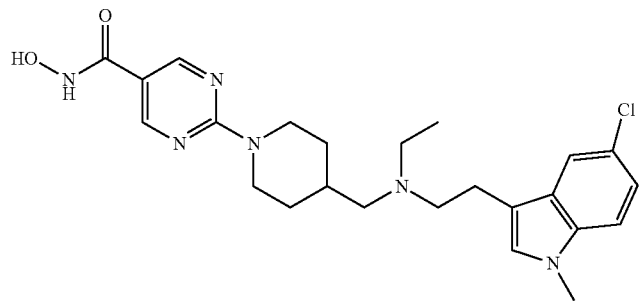 [SMILES: CCN(CCc1cn(C)c2ccc(Cl)cc12)CC1CCN(c2ncc(C(=O)NO)cn2)CC1]
•C₂HF₃O₂ (1:1); Co. No. 65; Ex. [B7]; mp. 111° C.
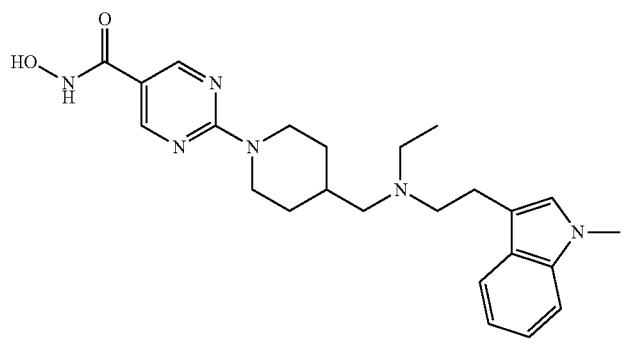 [SMILES: CCN(CCc1cn(C)c2ccccc12)CC1CCN(c2ncc(C(=O)NO)cn2)CC1]
Co. No. 66; Ex. [B7]; mp. 88° C.
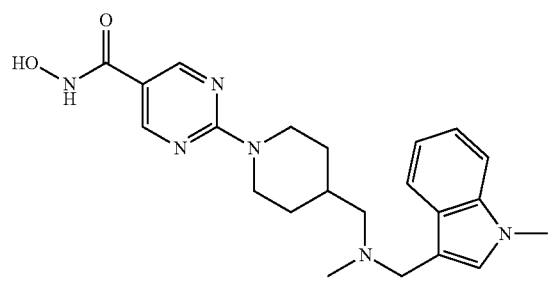 [SMILES: CN(Cc1cn(C)c2ccccc12)CC1CCN(c2ncc(C(=O)NO)cn2)CC1]
•C₂HF₃O₂ (1:1); Co. No. 67; Ex. [B7]; mp. 119° C.
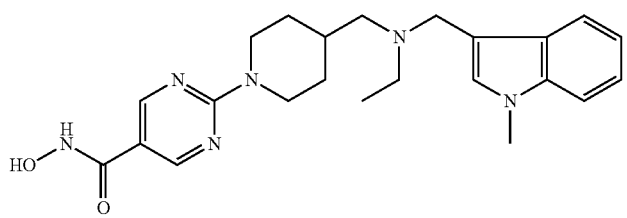 [SMILES: CCN(Cc1cn(C)c2ccccc12)CC1CCN(c2ncc(C(=O)NO)cn2)CC1]
Co. No. 68; Ex. [B7]; mp. 210° C.

TABLE F-2-continued
(final compounds)
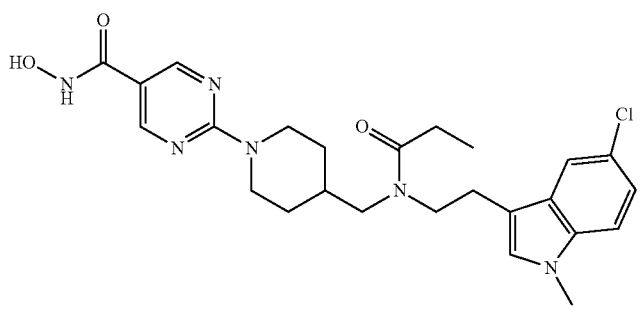 [SMILES: CCC(=O)N(CCc1cn(C)c2ccc(Cl)cc12)CC1CCN(c2ncc(C(=O)NO)cn2)CC1]
Co. No. 69; Ex. [B9]; mp. 110° C.
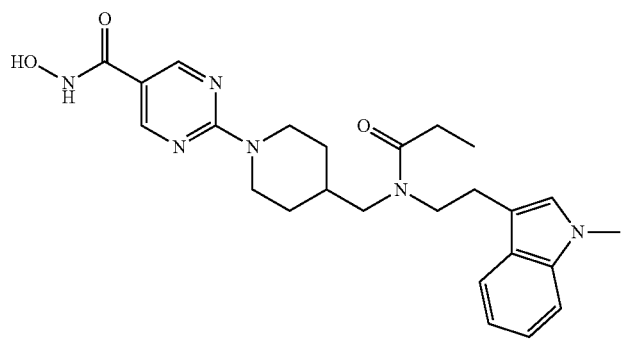 [SMILES: CCC(=O)N(CCc1cn(C)c2ccccc12)CC1CCN(c2ncc(C(=O)NO)cn2)CC1]
Co. No. 70; Ex. [B9]; mp. 80° C.
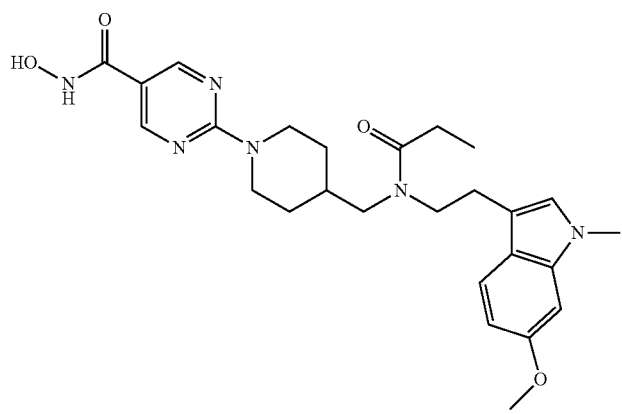 [SMILES: CCC(=O)N(CCc1cn(C)c2cc(OC)ccc12)CC1CCN(c2ncc(C(=O)NO)cn2)CC1]
Co. No. 71; Ex. [B9]; mp. 114° C.
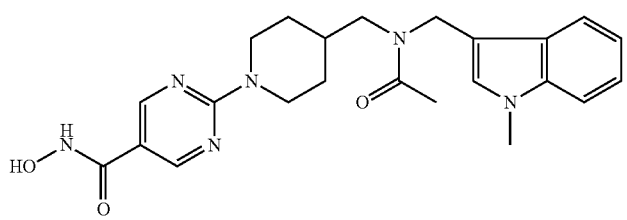 [SMILES: CC(=O)N(Cc1cn(C)c2ccccc12)CC1CCN(c2ncc(C(=O)NO)cn2)CC1]
Co. No. 72; Ex. [B9]; mp. 219° C.

TABLE F-2-continued
(final compounds)
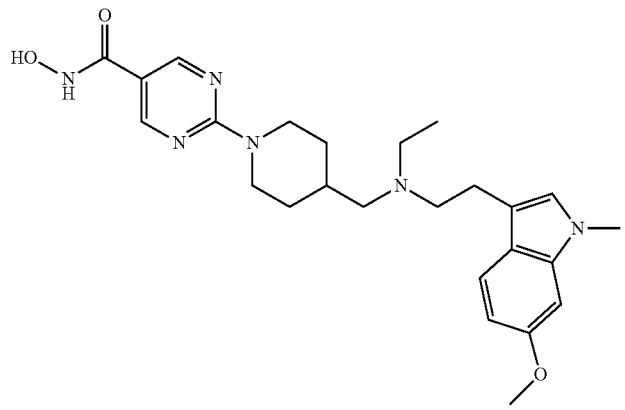 [SMILES: CCN(CCc1cn(C)c2cc(OC)ccc12)CC1CCN(c2ncc(C(=O)NO)cn2)CC1]
Co. No. 73; Ex. [B11]; mp. 98° C.
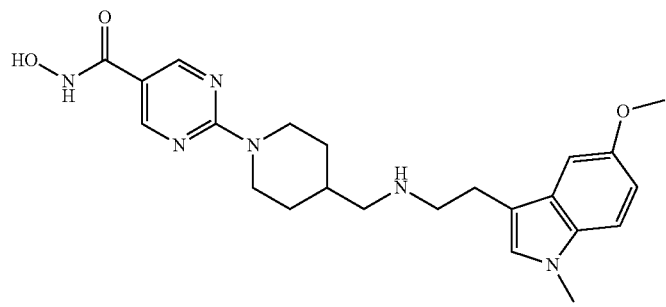 [SMILES: COc1ccc2c(c1)c(CCNCC1CCN(c3ncc(C(=O)NO)cn3)CC1)cn2C]
Co. No. 74; Ex. [B12]; mp. 149° C.
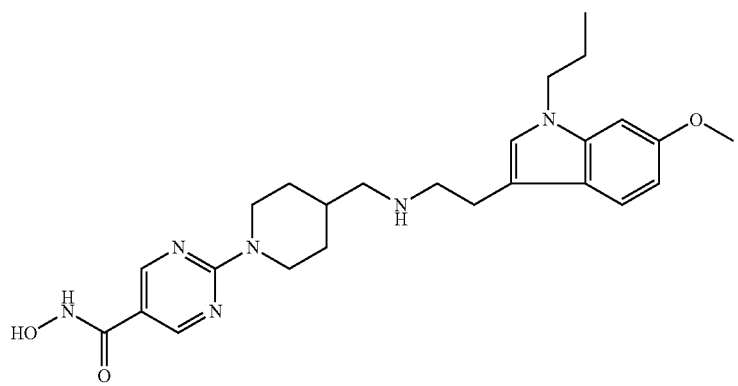 [SMILES: CCCn1cc(CCNCC2CCN(c3ncc(C(=O)NO)cn3)CC2)c2ccc(OC)cc21]
•$C_2HF_3O_2$ (1:1); Co. No. 75; Ex. [B12]; mp. 184° C.
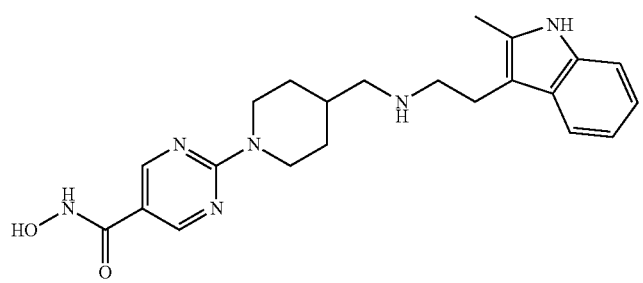 [SMILES: Cc1[nH]c2ccccc2c1CCNCC1CCN(c2ncc(C(=O)NO)cn2)CC1]
•$C_2HF_3O_2$ (1:1); Co. No. 76; Ex. [B15]; mp. 164° C.

TABLE F-2-continued (final compounds)

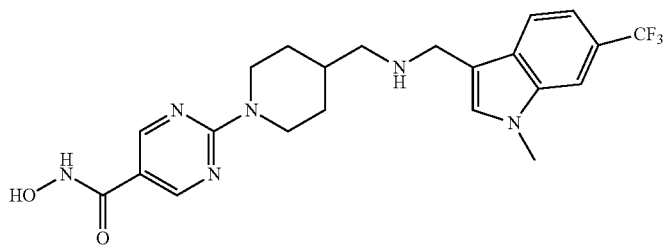 [SMILES: Cn1cc(CNCC2CCN(c3ncc(C(=O)NO)cn3)CC2)c2ccc(C(F)(F)F)cc21]

•$C_2HF_3O_2$ (1:1.4); Co. No. 77; Ex. [B5]; mp. 190° C.

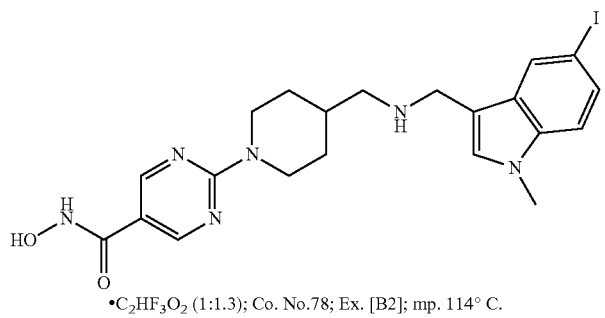

•$C_2HF_3O_2$ (1:1.3); Co. No.78; Ex. [B2]; mp. 114° C.

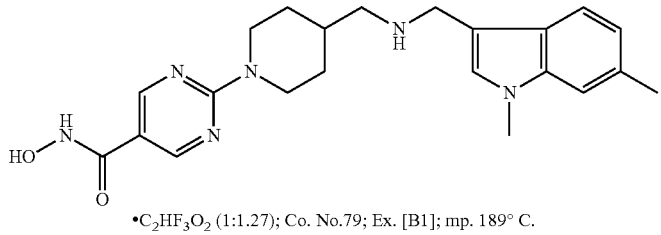

•$C_2HF_3O_2$ (1:1.27); Co. No.79; Ex. [B1]; mp. 189° C.

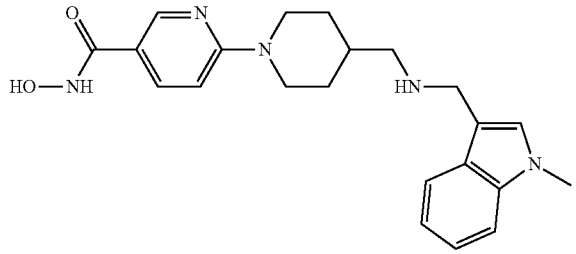 [SMILES: Cn1cc(CNCC2CCN(c3ccc(C(=O)NO)cn3)CC2)c2ccccc21]

•$C_2HF_3O_2$ (1:2.24); Co. No.80; Ex. [B1]; mp. 170° C.

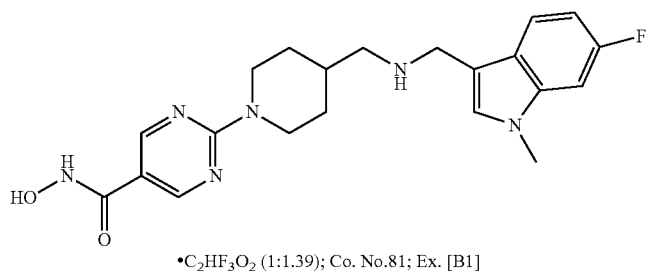

•$C_2HF_3O_2$ (1:1.39); Co. No.81; Ex. [B1]

C. Pharmacological Example

The in vitro assay for inhibition of histone deacetylase (see example C.1) measures the inhibition of HDAC enzymatic activity obtained with the compounds of formula (I).

Cellular activity of the compounds of formula (I) was determined on A2780 tumour cells using a colorimetric assay for cell toxicity or survival (Mosmann Tim, Journal of Immunological Methods 65: 55-63, 1983)(see example C.2).

The solubility of a compound measures the ability of a compound to stay in solution. In a first method the ability of a compound to stay in aqueous solution upon dilution (see example C.3.a) is measured. DMSO-stock solutions are diluted with a single aqueous buffer solvent in 3 consecutive steps. For every dilution turbidity is measured with a nephelometer.

In a second method the solubility of a compound at different pH's can be measured with the use of a Chemiluminescent Nitrogen Detector (see example C.3.b).

A drug's permeability expresses its ability to move from one medium into or through another. Specifically its ability to move through the intestinal membrane into the blood stream and/or from the blood stream into the target. Permeability (see example C.4) can be measured through the formation of a filter-immobilized artificial membrane phospholipid bilayer. In the filter-immobilized artificial membrane assay, a "sandwich" is formed with a 96-well microtitre plate and a 96-well filter plate, such that each composite well is divided into two chambers with a donor solution at the bottom and an acceptor solution at the top, separated by a 125 μm microfilter disc (0.45 μm pores), coated with 2% (wt/v) dodecane solution of dioleoylphosphatidyl-choline, under conditions that multi-lamellar bilayers form inside the filter channels when the system contacts an aqueous buffer solution. The permeability of compounds through this artificial membrane is measured in cm/s. The purpose is to look for the permeation of the drugs through a parallel artificial membrane at 2 different pH's: 4.0 and 7.4. Compound detection is done with UV-spectrometry at optimal wavelength between 250 and 500 nm.

Metabolism of drugs means that a lipid-soluble xenobiotic or endobiotic compound is enzymatically transformed into (a) polar, water-soluble, and excretable metabolite(s).

The major organ for drug metabolism is the liver. The metabolic products are often less active than the parent drug or inactive. However, some metabolites may have enhanced activity or toxic effects. Thus drug metabolism may include both "detoxication" and "toxication" processes. One of the major enzyme systems that determine the organism's capability of dealing with drugs and chemicals is represented by the cytochrome P450 monooxygenases, which are NADPH dependent enzymes. Metabolic stability of compounds can be determined in vitro with the use of subcellular human tissue (see example C.5.a.). Here metabolic stability of the compounds is expressed as % of drug metabolised after 15 minutes incubation of these compounds with microsomes. Quantitation of the compounds was determined by LC-MS analysis. Metabolic stability of compounds can also be determined by calculating the half live of compounds in rat hepatocyte cells (see example C.5.b.).

It has been shown that a wide variety of anti-tumoral agents activate the p21 protein, including DNA damaging agents and histone deacetylase inhibitors. DNA damaging agents activate the p21 gene through the tumour suppressor p53, while histone deacetylase inhibitors transcriptionally activates the p21 gene via the transcription factor Sp1. Thus, DNA damaging agents activate the p21 promoter through the p53 responsive element while histone deacetylase inhibitors activate the p21 promoter through spl sites (located at the −60 by to +40 by region relative to the TATA box) both leading to increased expression of the p21 protein. When the p21 promoter in a cells consists of a p21 1300 by promoter fragment that does not comprise the p53 responsive elements it is accordingly non-responsive to DNA damaging agents. The capacity of compounds to induce p21 can be evaluated in several ways. A first method is to treat tumour cells with the compound of interest and after lysis of the cells detects p21 induction with the p21 enzyme linked immunosorbent assay (WAF1 ELISA of Oncogene). The p21 assay is a "sandwich" enzyme immunoassay employing both mouse monoclonal and rabbit polyclonal antibodies. A rabbit polyclonal antibody, specific for the human p21 protein, has been immobilized onto the surface of the plastic wells provided in the kit. Any p21 present in the sample to be assayed will bind to the capture antibody. The biotinylated detector monoclonal antibody also recognizes human p21 protein, and will bind to any p21, which has been retained by the capture antibody. The detector antibody, in turn, is bound by horseradish peroxidase-conjugated streptavidin. The horseradish peroxidase catalyses the conversion of the chromogenic substrate tetramethylbenzidine from a colorless solution to a blue solution (or yellow after the addition of stopping reagent), the intensity of which is proportional to the amount of p21 protein bound to the plate. The colored reaction product is quantified using a spectrophotometer. Quantitation is achieved by the construction of a standard curve using known concentrations of p21 (provided lyophilised). This assay can measures p21 induction as the consequence of DNA damage or as the consequence of histone deacetylase inhibition (see example C.6.a.).

Another method tests the capacity of compounds to induce p21 as the consequence of HDAC inhibition at the cellular level. The cells can be stably transfected with an expression vector containing a p21 1300 bp promoter fragment that does not comprise the p53 responsive elements and wherein an increase of a reporter gene expression, compared to the control levels, identifies the compound as having p21 induction capacity. The reporter gene is a fluorescent protein and the expression of the reporter gene is measured as the amount of fluorescent light emitted (see example C.6.b.). The last method is an in vivo method wherein mice are used for screening the pharmaceutical activity of a compound. The above described stably transformed tumour cells can be administered to mice in an amount sufficient to effect production of a tumour. After the tumour cells had sufficient time to form a tumour, a potentially active compound can be administered to the animals and the effect of said compound on the tumour cells is evaluated by measuring the expression of the reporter gene. Incubation with pharmaceutical active compounds will result in an increase of reporter gene expression compared to the control levels (see example C.6.c.)

Specific HDAC inhibitors should not inhibit other enzymes like the abundant CYP P450 proteins. The CYP P450 (*E. coli* expressed) proteins 3A4, 2D6 en 2C9 convert their specific substrates into a fluorescent molecule. The CYP3A4 protein converts 7-benzyloxy-trifluoromethyl coumarin (BFC) into 7-hydroxy-trifluoromethyl coumarin.

The CYP2D6 protein converts 3-[2-(N,N-diethyl-N-methylamino)ethyl]-7-methoxy-4-methylcoumarin (AMMC) into 3-[2-(N,N-diethylamino)ethyl]-7-hydroxy-4-methylcoumarin hydrochloride and the CYP2C9 protein converts 7-Methoxy-4-trifluoromethyl coumarin (MFC) into 7-hydroxy-trifluoromethyl coumarin. Compounds inhibiting the enzymatic reaction will result in a decrease of fluoresent signal (see example C.7).

EXAMPLE C.1

In Vitro Assay for Inhibition of Histone Deacetylase

EXAMPLE C1A

In Vitro Assay with [$^3$H]-Labelled Substrate

HeLa nuclear extracts (supplier: Biomol) were incubated at 60 μg/ml with 75 μM of substrate. As a substrate for measuring HDAC activity a synthetic peptide, i.e. the amino acids 14-21 of histone H4, was used. The substrate is biotinylated at the $NH_2$-terminal part with a 6-aminohexanoic acid spacer, and is protected at the COOH-terminal part by an amide group and specifically [$^3$H]acetylated at lysine 16. The substrate, biotin-(6-aminohexanoic)Gly-Ala-([$^3$H]-acetyl-Lys-Arg-His-Arg-Lys-Val-$NH_2$), was added in a buffer containing 25 mM Hepes, 1 M sucrose, 0.1 mg/ml BSA and 0.01% Triton X-100 at pH 7.4. After 30 min the deacetylation reaction was terminated by the addition of HCl and acetic acid. (final concentration 0.035 mM and 3.8 mM respectively). After stopping the reaction, the free $^3$H-acetate was extracted with ethylacetate. After mixing and centrifugation, the radioactivity in an aliquot of the upper (organic) phase was counted in a β-counter.

For each experiment, controls (containing HeLa nuclear extract and DMSO without compound), a blank incubation (containing DMSO but no HeLa nuclear extract or compound) and samples (containing compound dissolved in DMSO and HeLa nuclear extract) were run in parallel. In first instance, compounds were tested at a concentration of $10^{-5}$M. When the compounds showed activity at $10^{-5}$M, a concentration-response curve was made wherein the compounds were tested at concentrations between $10^{-5}$M and $10^{-12}$M. In each test the blank value was substracted from both the control and the sample values. The control sample represented 100% of substrate deactylation. For each sample the radioactivity was expressed as a percentage of the mean value of the controls. When appropriate $IC_{50}$-values (concentration of the drug, needed to reduce the amount of metabolites to 50% of the control) were computed using probit analysis for graded data. Herein the effects of test compounds are expressed as $pIC_{50}$ (the negative log value of the $IC_{50}$-value) (see Table F-3).

EXAMPLE C.1.b

In Vitro Assay with Fluorescent-Labelled Substrate

The HDAC Fluorescent Activity Assay/Drug Discovery Kit of Biomol (cat.No: AK-500-0001) was used. The HDAC Fluorescent Activity Assay is based on the Fluor de Lys (Fluorogenic Histone deAcetylase Lysyl) substrate and developer combination. The Fluor de Lys substrate, comprises an acetylated lysine side chain. Deacetylation of the substrate sensitizes the substrate so that, in the second step, treatment with the Fluor de Lys developer produces a fluorophore. HeLa nuclear extracts (supplier: Biomol) were incubated at 60 μg/ml with 75 μM of substrate. The Fluor de Lys substrate was added in a buffer containing 25 mM Tris, 137 mM NaCl, 2.7 mM KCl and 1 mM $MgCl_2.6H_2O$ at pH 7.4. After 30 min, 1 volume of the developer was added. The fluorophore was excited with 355 nm light and the emitted light (450 nm) was be detected on a fluorometric plate reader. For each experiment, controls (containing HeLa nuclear extract and buffer), a blank incubation (containing buffer but no HeLa nuclear extract) and samples (containing compound dissolved in DMSO and further diluted in buffer and HeLa nuclear extract) were run in parallel. In first instance, compounds were tested at a concentration of $10^{-5}$M. When the compounds showed activity at $10^{-5}$M, a concentration-response curve was made wherein the compounds were tested at concentrations between $10^{-5}$M and $10^{-9}$M. All sample were tested 4 times. In each test the blank value was subtracted from both the control and the sample values. The control sample represented 100% of substrate deactylation. For each sample the fluorescence was expressed as a percentage of the mean value of the controls. When appropriate $IC_{50}$-values (concentration of the drug, needed to reduce the amount of metabolites to 50% of the control) were computed using probit analysis for graded data. Herein the effects of test compounds are expressed as $pIC_{50}$ (the negative log value of the $IC_{50}$-value) (see Table F-3).

EXAMPLE C.2

Determination of Antiproliferative Activity on A2780 Cells

All compounds tested were dissolved in DMSO and further dilutions were made in culture medium. Final DMSO concentrations never exceeded 0.1% (v/v) in cell proliferation assays. Controls contained A2780 cells and DMSO without compound and blanks contained DMSO but no cells. MTT was dissolved at 5 mg/ml in PBS. A glycine buffer comprised of 0.1 M glycine and 0.1 M NaCl buffered to pH 10.5 with NaOH (1 N) was prepared (all reagents were from Merck).

The human A2780 ovarian carcinoma cells (a kind gift from Dr. T. C. Hamilton [Fox Chase Cancer Centre, Pennsylvania, USA]) were cultured in RPMI 1640 medium supplemented with 2 mM L-glutamine, 50 μg/ml gentamicin and 10% fetal calf serum. Cells were routinely kept as monolayer cultures at 37° C. in a humidified 5% $CO_2$ atmosphere. Cells were passaged once a week using a trypsin/EDTA solution at a split ratio of 1:40. All media and supplements were obtained from Life Technologies. Cells were free of mycoplasma contamination as determined using the Gen-Probe *Mycoplasma* Tissue Culture kit (supplier: BioMérieux).

Cells were seeded in NUNC™ 96-well culture plates (Supplier: Life Technologies) and allowed to adhere to the plastic overnight. Densities used for plating were 1500 cells per well in a total volume of 200 μl medium. After cell adhesion to the plates, medium was changed and drugs and/or solvents were added to a final volume of 200 μl. Following four days of incubation, medium was replaced by 200 μl fresh medium and cell density and viability was assessed using an MTT-based assay. To each well, 25 μl MTT solution was added and the cells were further incubated for 2 hours at 37° C. The medium was then carefully aspirated and the blue MTT-formazan product was solubilized by addition of 25 μl glycine buffer followed by 100 μl of DMSO. The microtest plates were shaken for 10 min on a microplate shaker and the absorbance at 540 nm was measured using an Emax 96-well spectrophotometer (Supplier: Sopachem).

Within an experiment, the results for each experimental condition are the mean of 3 replicate wells. For initial screening purposes, compounds were tested at a single fixed concentration of $10^{-6}$ M. For active compounds, the experiments were repeated to establish full concentration-response curves. For each experiment, controls (containing no drug) and a blank incubation (containing no cells or drugs) were run in parallel. The blank value was subtracted from all control and sample values. For each sample, the mean value for cell growth (in absorbance units) was expressed as a percentage of the mean value for cell growth of the control. When appropriate, $IC_{50}$-values (concentration of the drug, needed to reduce cell growth to 50% of the control) were computed using probit analysis for graded data (Finney, D. J., Probit Analyses, $2^{nd}$ Ed. Chapter 10, Graded Responses, Cambridge University Press, Cambridge 1962). Herein the effects of test compounds are expressed as $pIC_{50}$ (the negative log value of the $IC_{50}$-value)(see Table F-3).

EXAMPLE C.3

Solubility/Stability

C.3.1. Solubility in Aqueas Media In the first dilution step, 10 µl of a concentrated stock-solution of the active compound, solubilized in DMSO (5 mM), was added to 100 µl phosphate citrate buffer pH 7.4 and mixed. In the second dilution step, an aliquot (20 µl) of the first dilution step was further dispensed in 100 µl phosphate citrate buffer pH 7.4 and mixed. Finally, in the third dilution step, a sample (20 µl) of the second dilution step was further diluted in 100 µl phosphate citrate buffer pH 7.4 and mixed. All dilutions were performed in 96-well plates Immediately after the last dilution step the turbidity of the three consecutive dilution steps were measured with a nephelometer. Dilution was done in triplicate for each compound to exclude occasional errors. Based on the turbidity measurements a ranking is performed into 3 classes. Compounds with high solubility obtained a score of 3 and for this compounds the first dilution is clear. Compounds with medium solubility obtained a score of 2. For these compounds the first dilution is unclear and the second dilution is clear. Compounds with low solubility obtained a score of 1 and for these compounds both the first and the second dilution are unclear (see Table F-3).

C.3.b. Solubility/Stability at Different pH's

The solubility of a compound, at different pH's, can also be measured with the use of a chemiluminescent nitrogen detector. (see Table F-3).

EXAMPLE C.4

Parallel Artificial Membrane Permeability Analysis

The stock samples (aliquots of 10 µl of a stock solution of 5 mM in 100% DMSO) were diluted in a deep-well or Premix plate containing 2 ml of an aqueous buffer system pH 4 or pH 7.4 (PSR4 System Solution Concentrate (pION)).

Before samples were added to the reference plate, 150 µl of buffer was added to wells and a blank UV-measurement was performed. Thereafter the buffer was discarded and the plate was used as reference plate. All measurements were done in UV-resistant plates (supplier: Costar or Greiner).

After the blank measurement of the reference plate, 150 µl of the diluted samples was added to the reference plate and 200 µl of the diluted samples was added to donorplate 1. An acceptor filter plate 1 (supplier: Millipore, type:MAIP N45) was coated with 4 µl of the artificial membrane-forming solution (1,2-Dioleoyl-sn-Glycer-3-Phosphocholine in Dodecane containing 0.1% 2,6-Di-tert-butyl-4-methylphenol and placed on top of donor plate 1 to form a "sandwich". Buffer (200 µl) was dispensed into the acceptor wells on the top. The sandwich was covered with a lid and stored for 18 h at room temperature in the dark.

A blank measurement of acceptor plate 2 was performed through the addition of 150 µl of buffer to the wells, followed by an UV-measurement. After the blank measurement of acceptor plate 2 the buffer was discarded and 150 µl of acceptor solution was transferred from the acceptor filter plate 1 to the acceptor plate 2. Then the acceptor filter plate 1 was removed form the sandwich. After the blank measurement of donor plate 2 (see above), 150 µl of the donor solution was transferred from donor plate 1 to donor plate 2. The UV spectra of the donor plate 2, acceptor plate 2 and reference plate wells were scanned (with a SpectraMAX 190). All the spectra were processed to calculate permeability with the PSR4p Command Software. All compounds were measured in triplo. Carbamazepine, griseofulvin, acycloguanisine, atenolol, furosemide, and chlorothiazide were used as standards in each experiment. Compounds were ranked in 3 categories as having a low permeability (mean effect $<0.5 \times 10^{-6}$ cm/s; score 1), a medium permeability ($1 \times 10^{-6}$ cm/s>mean effect $0.5 \times 10^{-6}$ cm/s; score 2) or a high permeability $1 \times 10^{-6}$ cm/s; score 3).

EXAMPLE C.5

Metabolic Stability

EXAMPLE C.5A

Sub-cellular tissue preparations were made according to Gorrod et al. (Xenobiotica 5: 453-462, 1975) by centrifugal separation after mechanical homogenization of tissue. Liver tissue was rinsed in ice-cold 0.1 M Tris-HCl (pH 7.4) buffer to wash excess blood. Tissue was then blotted dry, weighed and chopped coarsely using surgical scissors. The tissue pieces were homogenized in 3 volumes of ice-cold 0.1 M phosphate buffer (pH 7.4) using either a Potter-S (Braun, Italy) equipped with a Teflon pestle or a Sorvall Omni-Mix homogeniser, for 7×10 sec. In both cases, the vessel was kept in/on ice during the homogenization process.

Tissue homogenates were centrifuged at 9000×g for 20 minutes at 4° C. using a Sorvall centrifuge or Beckman Ultracentrifuge. The resulting supernatant was stored at −80° C. and is designated 'S9'.

The S9 fraction can be further centrifuged at 100.000×g for 60 minutes (4° C.) using a Beckman ultracentrifuge. The resulting supernatant was carefully aspirated, aliquoted and designated 'cytosol'. The pellet was re-suspended in 0.1 M phosphate buffer (pH 7.4) in a final volume of 1 ml per 0.5 g original tissue weight and designated 'microsomes'.

All sub-cellular fractions were aliquoted, immediately frozen in liquid nitrogen and stored at −80° C. until use.

For the samples to be tested, the incubation mixture contained PBS (0.1M), compound (5 µM), microsomes (1 mg/ml) and a NADPH-generating system (0.8 mM glucose-6-phosphate, 0.8 mM magnesium chloride and 0.8 Units of glucose-6-phosphate dehydrogenase). Control samples contained the same material but the microsomes were replaced by heat inactivated (10 min at 95 degrees Celsius) microsomes. Recovery of the compounds in the control samples was always 100%.

The mixtures were preincubated for 5 min at 37 degrees Celsius. The reaction was started at timepoint zero (t=0) by addition of 0.8 mM NADP and the samples were incubated for 15 min (t=15). The reaction was terminated by the addition of 2 volumes of DMSO. Then the samples were centrifuged for 10 min at 900×g and the supernatants were stored at room temperature for no longer as 24 h before analysis. All incubations were performed in duplo. Analysis of the supernatants was performed with LC-MS analysis. Elution of the samples was performed on a Xterra MS C18 (50×4.6 mm, 5 µm, Waters, US). An Alliance 2790 (Supplier: Waters, US) HPLC system was used. Elution was with buffer A (25 mM ammoniumacetate (pH 5.2) in $H_2O$/acetonitrile (95/5)), solvent B being acetonitrile and solvent C methanol at a flow rate of 2.4 ml/min. The gradient employed was increasing the organic phase concentration from 0% over 50% B and 50% C in 5 min up to 100% B in 1 min in a linear fashion and organic phase concentration was kept stationary for an additional 1.5 min. Total injection volume of the samples was 25 µl.

A Quattro (supplier: Micromass, Manchester, UK) triple quadrupole mass spectrometer fitted with and ESI source was used as detector. The source and the desolvation temperature were set at 120 and 350° C. respectively and nitrogen was used as nebuliser and drying gas. Data were acquired in positive scan mode (single ion reaction). Cone voltage was set at 10 V and the dwell time was 1 sec.

Metabolic stability was expressed as % metabolism of the compound after 15 min of incubation in the presence of active microsomes (E(act))

$$\left(\% \text{ metabolism} = 100\% - \left(\left(\frac{\text{Total Ion Current } (TIC) \text{ of } E(\text{act}) \text{ at } t = 15}{TIC \text{ of } E(\text{act}) \text{ at } t = 0}\right) \times 100\right)\right).$$

Compounds that had a percentage metabolism less than 20% were defined as highly metabolic stable. Compound that had a metabolism between 20 and 70% were defined as intermediately stable and compounds that showed a percentage metabolism higher than 70 were defined as low metabolic stable. Three reference compounds were always included whenever a metabolic stability screening was performed. Verapamil was included as a compound with low metabolic stability (% metabolism=73%). Cisapride was included as a compound with medium metabolic stability (% metabolism 45%) and propanol was included as a compound with intermediate to high metabolic stability (25% metabolism). These reference compounds were used to validate the metabolic stability assay.

C.5.b: Metabolic Stability with Rat Hepatocytes Cell Culture

Rat hepatocytes were isolated from male Sprague Dowley rats. The compounds were dissolved to a 5 mM stock solution in 100% DMSO and incubated at a final concentration of 5 µM for 0, 15, 30, 60 and 120 min with rat hepatocyte cell cultures (0.5 million viable cells/0.5 ml) using 24-well plates. Samples were prepared for LC-MS by addition of two volumes of DMSO. The samples were thoroughly shaken and subsequently centrifuged at 900 g for 10 min (room temperature). All experiments were performed in triplicate. Of the resulting supernatant 50 µl was analysed by LC-MS.

For LC-MS, elution of samples was performed on a Hypersil BDS C18 column (50×4.6 mm, 5 µm, Thermohypersil, UK). The HPLC system comprised a Surveyor delivery system (Surveyor Inc., San Jose, US) equipped with a Surveyor autosampler device. Elution was with buffer A (10 mM ammoniumacetate (pH 6.9) in $H_2O$/Acetonitrile (95:5)) and solvent B (acetonitrile) at a flow rate of 1.2 ml/min. The gradient employed was 0.5 min solvent A as start condition followed by increasing the organic phase concentration from 0% till 95% B over 2 min in a linear fashion. This phase was kept stationary for a further 2 min and reduced again to 0% B within 0.5 min.

Total injection volume of samples was 50 µL. Column oven temperature was kept at 40° C. The LC flow was splitted for MS detection and 0.1 ml let into the source.

An triple quadrupol mass spectrometer TSQ Quantum (Thermofinnigan, LaJolla, USA) mass spectrometer fitted with an ESI source was used for detection. Source voltage was set at 3800 volt, the capillary temperature at 300° C. The mass spectrometer was operated in positive ion mode in SIM adjusted to the mass of M+H with a scan width of 1 Da for quantification purposes. Instrument control, data acquisition and processing were performed using the Xcalibur software (ThermoFinnigan, San Jose, Calif., U.S.A). The metabolic stability of compounds in rat hepatocytes was expressed as in vitro half-lives.

As reference, compound R306465 (WO03/76422) was used (in vitro half-live: 8 min) Compound 1 and compound 5 were tested and had an in vitro half-live of 81 min. and 60 min. respectively.

EXAMPLE C.6 p21 Induction Capacity

EXAMPLE C.6.a p21 Enzyme Linked Immunosorbent Assay

The following protocol has been applied to determine the p21 protein expression level in human A2780 ovarian carcinoma cells. The A2780 cells (20000 cells/180 µl) were seeded in 96 microwell plates in RPMI 1640 medium supplemented with 2 mM L-glutamine, 50 µg/ml gentamicin and 10% fetal calf serum. 24 hours before the lysis of the cells, compounds were added at final concentrations of $10^{-5}$, $10^{-6}$, $10^{-7}$ and $10^{-8}$ M. All compounds tested were dissolved in DMSO and further dilutions were made in culture medium. 24 hours after the addition of the compound, the supernatants were removed from the cells. Cells were washed with 200 µl ice-cold PBS. The wells were aspirated and 30 µl of lysisbuffer (50 mM Tris.HCl (pH 7.6), 150 mM NaCl, 1%

Nonidet p40 and 10% glycerol) was added. The plates were incubated overnight at −70° C.

The appropriate number of microtiter wells were removed from the foil pouch and placed into an empty well holder. A working solution (1×) of the Wash Buffer (20× plate wash concentrate: 100 ml 20-fold concentrated solution of PBS and surfactant.

Contains 2% chloroacetamide) was prepared. The lyophilised p21WAF standard was reconstituted with distilled $H_2O$ and further diluted with sample diluent (provided in the kit)

The samples were prepared by diluting them 1:4 in sample diluent. The samples (100 µl) and the p21WAF1 standards (100 µl) were pipetted into the appropriate wells and incubated at room temperature for 2 hours. The wells were washed 3 times with 1× wash buffer and then 100 µl of detector antibody reagent (a solution of biotinylated monoclonal p21WAF1 antibody) was pipetted into each well. The wells were incubated at room temperature for 1 hour and then washed three times with 1× wash buffer. The 400× conjugate (peroxidase streptavidine conjugate: 400-fold concentrated solution) was diluted and 100 µA of the 1× solution was added to the wells. The wells were incubated at room temperature for 30 min and then washed 3 times with 1× wash buffer and 1 time with distilled $H_2O$, Substrate solution (chromogenic substrate)(100 µl) was added to the wells and the wells were incubated for 30 minutes in the dark at room temperature. Stop solution was added to each well in the same order as the previously added substrate solution. The absorbance in each well was measured using a spectrophotometric plate reader at dual wavelengths of 450/595 nm. For each experiment, controls (containing no drug) and a blank incubation (containing no cells or drugs) were run in parallel. The blank value was substracted from all control and sample values. For each sample, the value for p21WAF1 induction (in absorbance units) was expressed as the percentage of the value for p21WAF1 present in the control. Percentage induction higher than 130% was defined as significant induction. Nine compounds were tested and all showed significant induction at $10^{-6}$M.

EXAMPLE C.6.b

Cellular Method

A2780 cells (ATCC) were cultivated in RPMI 1640 medium supplemented with 10% FCS, 2 mM L-glutamine and gentamycine at 37° C. in a humidified incubator with 5% $CO_2$. All cell culture solutions are provided by Gibco-BRL (Gaithersburg, Md.). Other materials are provided by Nunc.

Genomic DNA was extracted from proliferating A2780 cells and used as template for nested PCR isolation of the p21 promoter. The first amplification was performed for 20 cycles at an annealing temperature of 55° C. using the oligonucleotide pair GAGGGCGCGGTGCTTGG (SEQ ID NO: 1) and TGC-CGCCGCTCTCTCACC (SEQ ID NO: 2) with the genomic DNA as template. The resulting 4.5 kb fragment containing the −4551 to +88 fragment relative to the TATA box was re-amplified with the oligonucleotides TCGGGTACCGAGGGCGCGGTGCTTGG (SEQ ID NO: 3) and ATACTCGAGTGCCGCCGCTCTCTCACC (SEQ ID NO: 4) for 20 cycles with annealing at 88° C. resulting in a 4.5 kb fragment and subsequently with the oligonucleotide pair TCGGGTACCGGTAGATGGGAGCGGATAGACACATC (SEQ ID NO: 5) and ATACTCGAGTGCCGCCGCTCTCTCACC (SEQ ID NO: 6) for 20 cycles with annealing at 88° C. resulting in a 1.3 kb fragment containing the −1300 to +88 fragment relative to the TATA box. The restriction sites XhoI and KpnI present in the oligonucleotides (underlined sequence) were used for subcloning.

The luciferase reporter was removed from the pGL3-basic and replaced by the ZsGreen reporter (from the pZsGreenl-N1 plasmid) at KpnI and XbaI restriction sites. pGL3-basic-ZsGreen-1300 was constructed via insertion of the above mentioned 1.3 kb fragment of the human p21 promoter region into pGL3-basic-ZsGreen at the XhoI and KpnI sites. All restriction enzymes are provided by Boehringer Manheim (Germany).

A2780 cells were plated into a 6-well plate at a density of $2\times10^5$ cells, incubated for 24 hours, and transfected with 2 ug of pGL3-basic-ZsGreen-1300 and 0.2 ug of pSV2 neo vector by using Lipofectamine 2000 (Invitrogen, Brussels, Belgium) as described by manufacturer. The transfected cells were selected for 10 days with G418 (Gibco-BRL, Gaithersburg, Md.) and single cell suspensions were grown. After three weeks, single clones were obtained.

The A2780 selected clones were expanded and seeded at 10000 cells per well into 96-well plates. 24 hours after seeding, the cells were treated for an additional 24 hours with compounds (affecting spl sites in the proximal p21 promoter region). Subsequently, cells were fixed with 4% PFA for 30' and counterstained with Hoechst dye. The p21 promoter activation leading to ZsGreen production and thus fluorescence, was monitored by the Ascent Fluoroskan (Thermo Labsystems, Brussels, Belgium).

For each experiment, controls (containing no drug) and a blank incubation (containing no cells or drugs) were run in parallel. The blank value was substracted from all control and sample values. For each sample, the value for p21 induction was expressed as the percentage of the value for p21 present in the control. Percentage induction higher than 130% was defined as significant induction.

Seventy one compounds were tested and all showed significant induction at $10^{-6}$M.

EXAMPLE C.6.c

In Vivo Method

A selected clone was injected subcutaneous ($10^7$ cells/200 μl) into the flank of nude mice and a calliper measurable tumour was obtained after 12 days. From day 12 on, animals were dosed, orally or intraveinally, daily during 6 days with solvent and 20-40 mpk compound (4-10 animals each). Tumours were evaluated for fluorescence by the in-house developed Automated Whole Body Imaging System (Fluorescent stereomicroscope type Olympus® SZX12 equipped with a GFP filter and coupled to a CCD camera type JAI® CV-M90 controlled by a software package based on the IMAQ Vision Software from National Instruments®). As reference, compound R306465 (WO03/76422) was used. Compounds were ranked as inactive (no fluorescence measurable), weaker, identical or better than R306465. Compound 1 was tested and was better than R306465.

EXAMPLE C.7

P450 Inhibiting Capacity

All compounds tested were dissolved in DMSO (5 mM) and a further dilution to 5 $10^{-4}$ M was made in acetonitrile. Further dilutions were made in assay buffer (0.1M NaK phosphate buffer pH 7.4) and the final solvent concentration was never higher than 2%. The assay for the CYP3A4 protein comprises per well 15 μmol P450/mg protein (in 0.01M NaK-phosphate buffer+1.15% KCl), an NADPH generating system (3.3 mM Glucose-6-phosphate, 0.4 U/ml Glucose-6-phosphate dehydrogenase, 1.3 mM NADP and 3.3 mM $MgCl_2.6H_2O$ in assay buffer) and compound in a total assay volume of 100 μl. After a 5 min pre-incubation at 37° C. the enzymatic reaction was started with the addition of 150 μM of the fluoresent probe substrate BFC in assay buffer. After an incubation of 30 minutes at room temperature the reaction was terminated after addition of 2 volumes of acetonitrile. Fluorescent determinations were carried out at an excitation wavelength of 405 nm and an emission wavelength of 535 nm. Ketoconazole ($IC_{50}$-value=$3\times10^{-8}$M) was included as reference compound in this experiment. The assay for the CYP2D6 protein comprises per well 6 μmol P450/mg protein (in 0.01M NaK-phosphate buffer+1.15% KCl), an NADPH generating system (0.41 mM Glucose-6-phosphate, 0.4 U/ml Glucose-6-phosphate dehydrogenase, 0.0082 mM NADP and 0.41 mM $MgCl_2.6H_2O$ in assay buffer) and compound in a total assay volume of 100 41. After a 5 min pre-incubation at 37° C. the enzymatic reaction was started with the addition of 3 μM of the fluoresent probe substrate AMMC in assay buffer. After an incubation of 45 minutes at room temperature the reaction was terminated after addition of 2 volumes of acetonitrile. Fluorescent determinations were carried out at an excitation wavelength of 405 nm and an emission wavelength of 460 nm. Quinidine ($IC_{50}$-value <$5\times10^{-8}$M) was included as reference compound in this experiment.

The assay for the CYP2C9 protein comprises per well 15 µmol P450/mg protein (in 0.01M NaKphosphate buffer+ 1.15% KCl), an NADPH generating system (3.3 mM Glucose-6-phosphate, 0.4 U/ml Glucose-6-phosphate dehydrogenase, 1.3 mM NADP and 3.3 mM $MgCl_2.6H_2O$ in assay buffer) and compound in a total assay volume of 100 µl. After a 5 min pre-incubation at 37° C. the enzymatic reaction was started with the addition of 200 µM of the fluoresent probe substrate MFC in assay buffer. After an incubation of 30 minutes at room temperature the reaction was terminated after addition of 2 volumes of acetonitrile. Fluorescent determinations were carried out at an excitation wavelength of 405 nm and an emission wavelength of 535 nm. Sulfaphenazole ($IC_{50}$-value=$6.8\times10^{-7}$M) was included as reference compound in this experiment.

For initial screening purposes, compounds were tested at a single fixed concentration of $1\times10^{-5}$ M. For active compounds, the experiments were repeated to establish full concentration-response curves. For each experiment, controls (containing no drug) and a blank incubation (containing no enzyme or drugs) were run in parallel. All compounds were assayed in quadruplicate. The blank value was subtracted from all control and sample values. For each sample, the mean value of P450 activity of the sample (in relative fluorescence units) was expressed as a percentage of the mean value of P450 activity of the control. Percentage inhibition was expressed as 100% minus the mean value of P450 activity of the sample. When appropriate, $IC_{50}$-values (concentration of the drug, needed to reduce P450 activity to 50% of the control) were calculated.

TABLE F-3 lists the results of the compounds that were tested according to example C.1.a., C.1.b, C.2, C.3.a. and C.3.b.

| Compound number | Enzymatic activity pIC50 C.1.a. | Enzymatic activity pIC50 C.1.b | Cellular activity pIC50 C.2 | Solubility C.3.a. | Solubility C.3.b. pH = 2.3 (mg/ml) |
|---|---|---|---|---|---|
| 5 | 8.6 | | 6.5 | | 2.0 |
| 1a | 8.8 | 9.2 | 8.2 | 3 | 1.4 |
| 6 | 8.2 | | 6.3 | | |
| 7 | 8.5 | | 6.1 | | |
| 3 | 8.5 | | 6.7 | | |
| 4 | 8.7 | | 7.0 | 3 | |
| 17 | | 7.8 | 6.8 | | |
| 8 | | 8.3 | 7.1 | | 2.4 |
| 9 | | 8.3 | 7.1 | | |
| 10 | | 8.1 | 7.5 | 3 | 3.7 |
| 16 | | 8.6 | 7.1 | 3 | |
| 11 | | 8.2 | 7.5 | 3 | 2.8 |
| 2 | | 8.4 | 7.5 | 3 | |
| 15 | | 8.5 | 7.5 | | |
| 14 | | 8.4 | 7.4 | | 1.7 |
| 13 | | 6.0 | 7.5 | 3 | |
| 12 | | 8.2 | 7.1 | 3 | |
| 35 | | 8.2 | 6.7 | | |
| 68 | | >9.0 | 7.2 | | 2.5 |
| 63 | | >9.0 | 7.5 | | |
| 67 | | 8.3 | 7.5 | | 1.9 |
| 76 | | 7.8 | 6.7 | | |
| 72 | | 7.9 | 6.8 | | |
| 80 | | 7.8 | 7.1 | | |
| 34 | | 8.4 | 7.5 | | |
| 33 | | 10.0 | 7.5 | | 1.6 |
| 32 | | 8.0 | 8.4 | | 1.5 |
| 21 | | 8.5 | 7.6 | | 1.9 |
| 49 | | 8.7 | 7.5 | | 3.3 |
| 53 | | 10.0 | 8.0 | | |
| 20 | | 9.5 | 8.1 | | 2.7 |
| 64 | | 8.9 | 7.8 | | |
| 62 | | 9.5 | 8.0 | | |
| 28 | | 8.1 | 7.1 | | |
| 61 | | 8.9 | 7.6 | | |
| 60 | | 8.7 | 6.9 | | 3.1 |
| 59 | | 9.0 | 7.7 | | |
| 58 | | 10.0 | 5.8 | | |
| 19 | | 8.0 | 7.1 | | |
| 24 | | 7.6 | 6.5 | | 1.6 |
| 57 | | 10.2 | 7.6 | | 2.8 |
| 56 | | 9.2 | 7.6 | | |
| 55 | | 10.1 | 7.8 | | 2.0 |
| 54 | | 10.2 | 7.9 | | |
| 52 | | 10.3 | 8.1 | | |
| 51 | | 9.8 | 8.0 | | |
| 50 | | 8.6 | 7.6 | | 2.4 |
| 48 | | >9.0 | 8.2 | | |
| 66 | | >9.0 | 7.4 | | 1.7 |
| 73 | | 7.9 | 7.1 | | |
| 47 | | 8.8 | 8.0 | | 4.0 |
| 74 | | 8.2 | 7.1 | | |
| 46 | | 9.0 | 8.0 | | |
| 31 | | 8.2 | 7.4 | | |
| 75 | | 7.3 | 7.1 | | |
| 27 | | >9.0 | 8.0 | | |
| 45 | | 9.0 | 6.7 | | 1.7 |
| 44 | | 8.2 | 7.4 | | 1.8 |
| 43 | | 8.5 | 7.8 | | 2.1 |
| 29 | | 7.9 | 6.9 | | |
| 42 | | 8.3 | 7.5 | | |
| 71 | | 7.5 | 6.5 | | |
| 70 | | 8.5 | 6.8 | | |
| 69 | | 7.6 | 6.7 | | |
| 25 | | 7.6 | 7.0 | | |
| 41 | | 8.4 | 5.8 | | |
| 40 | | 8.5 | 7.5 | | |
| 23 | | 8.4 | 7.5 | | |
| 22 | | 9.1 | 7.2 | | |
| 26 | | >9.0 | 7.5 | | |
| 65 | | >9.0 | 7.5 | | 1.6 |
| 39 | | 9.0 | 7.5 | | 2.0 |
| 30 | | 9.0 | 7.5 | | 2.1 |
| 38 | | >9.0 | 7.5 | | |
| 37 | | 8.6 | 7.5 | | |
| 36 | | 8.7 | 8.6 | | 2.5 |
| 79 | | 8.4 | 8.1 | | 2.7 |
| 18 | | 8.3 | 8.0 | | |
| 81 | | 8.9 | 7.5 | | |

D. Composition Example

Film-Coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A method of treating ovarian cancer in a subject in need thereof comprising administering to the subject a therapeutically effective amount of a compound of formula (I)

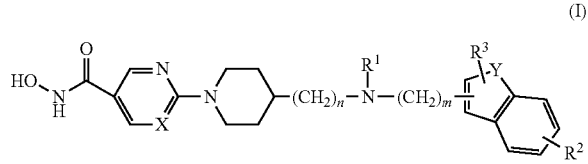

or an N-oxide form, pharmaceutically acceptable addition salt or stereo-chemically isomeric form thereof, wherein
n is an integer with value 0, 1 or 2 and when n is 0 then a direct bond is intended;
m is an integer with value 1 or 2;
X is independently N or CH;
Y is independently O, S, or $NR^4$; wherein
$R^4$ is hydrogen, $C_{1-6}$alkyl, $C_{1-6}$alkyloxy$C_{1-6}$alkyl, $C_{3-6}$cycloalkyl, $C_{3-6}$cycloalkylmethyl, phenyl$C_{1-6}$alkyl, —C(=O)—$CHR^5R^6$ or —S(=O)$_2$—N(CH$_3$)$_2$; wherein
each $R^5$ and $R^6$ is independently hydrogen, amino, $C_{1-6}$alkyl or amino$C_{1-6}$alkyl; and
when Y is $NR^4$ and $R^2$ is on the 7-position of the indolyl, then $R^2$ and $R^4$ together optionally form the bivalent radical —(CH$_2$)$_2$— (a-1), or —(CH$_2$)$_3$— (a-2);

$R^1$ is hydrogen, $C_{1-6}$alkyl, hydroxy$C_{1-6}$alkyl, $C_{1-6}$alkylsulfonyl, $C_{1-6}$alkylcarbonyl or mono- or di($C_{1-6}$alkyl)aminosulfonyl;
$R^2$ is hydrogen, hydroxy, amino, halo, $C_{1-6}$alkyl, cyano, $C_{2-6}$alkenyl, polyhalo$C_{1-6}$alkyl, nitro, phenyl, $C_{1-6}$alkylcarbonyl, hydroxycarbonyl, $C_{1-6}$alkylcarbonylamino, $C_{1-6}$alkyloxy, or mono- or di($C_{1-6}$alkyl)amino;
$R^3$ is hydrogen, $C_{1-6}$alkyl, or $C_{1-6}$alkyloxy; and
when $R^2$ and $R^3$ are on adjacent carbon atoms, they optionally form the bivalent radical

—O—CH$_2$—O—.

2. The method of claim 1 wherein in the compound of formula I
$R^4$ is hydrogen, $C_{1-6}$alkyl, $C_{3-6}$cycloalkyl, $C_{3-6}$cycloalkylmethyl, —C(=O)—$CHR^5R^6$ or —S(=O)$_2$—N(CH$_3$)$_2$;
$R^1$ is hydrogen, $C_{1-6}$alkyl, hydroxy$C_{1-6}$alkyl, $C_{1-6}$alkylsulfonyl, or mono- or di($C_{1-6}$alkyl)aminosulfonyl; and
$R^3$ is hydrogen.

3. The method of claim 1 wherein in the compound of formula I
n is an integer with value 0 or 1;
X is independently N;
$R^4$ is hydrogen or $C_{1-6}$alkyl;
$R^1$ is hydrogen, $C_{1-6}$alkyl or hydroxy$C_{1-6}$alkyl; and
$R^2$ is hydrogen, halo, $C_{1-6}$alkyl or $C_{1-6}$alkyloxy.

4. The method of claim 1 wherein in the compound of formula I
n is an integer with value 0 or 1;
$R^4$ is hydrogen, $C_{1-6}$alkyl, $C_{1-6}$alkyloxy$C_{1-6}$alkyl, $C_{3-6}$cycloalkyl or phenyl$C_{1-6}$alkyl;
$R^1$ is hydrogen, $C_{1-6}$alkyl, hydroxy$C_{1-6}$alkyl, $C_{1-6}$alkylcarbonyl or $C_{1-6}$alkylsulfonyl; and $R^2$ is hydrogen, halo, $C_{1-6}$alkyl, cyano, nitro or $C_{1-6}$alkyloxy.

5. The method of claim 1 wherein in the compound of formula I
n is an integer with value 1;
m is an integer with value 1;
X is independently N;
Y is independently $NR^4$;
$R^4$ is $C_{1-6}$alkyl;
$R^1$ is hydrogen;
$R^2$ is hydrogen or halo; and
$R^3$ is hydrogen.

6. The method of claim 1 wherein in the compound of formula I
n is an integer with value 0 or 1;
$R^4$ is hydrogen, $C_{1-6}$alkyl, $C_{1-6}$alkyloxy$C_{1-6}$alkyl, $C_{3-6}$cycloalkyl or phenyl$C_{1-6}$alkyl;
$R^1$ is hydrogen, $C_{1-6}$alkyl, hydroxy$C_{1-6}$alkyl, $C_{1-6}$alkylcarbonyl or $C_{1-6}$alkylsulfonyl; and
$R^2$ is hydrogen, halo, $C_{1-6}$alkyl, cyano, nitro, polyhalo $C_{1-6}$alkyl or $C_{1-6}$alkyloxy.

7. The method of claim 1 wherein in the compound of formula I
n is an integer with value 1;
m is an integer with value 1;
X is independently N;
Y is independently $NR^4$;
$R^4$ is $C_{1-6}$alkyl;
$R^1$ is hydrogen;
$R^2$ is hydrogen or halo; and
$R^3$ is hydrogen.

8. The method of claim 7, wherein the compound of formula I is selected from the group consisting of

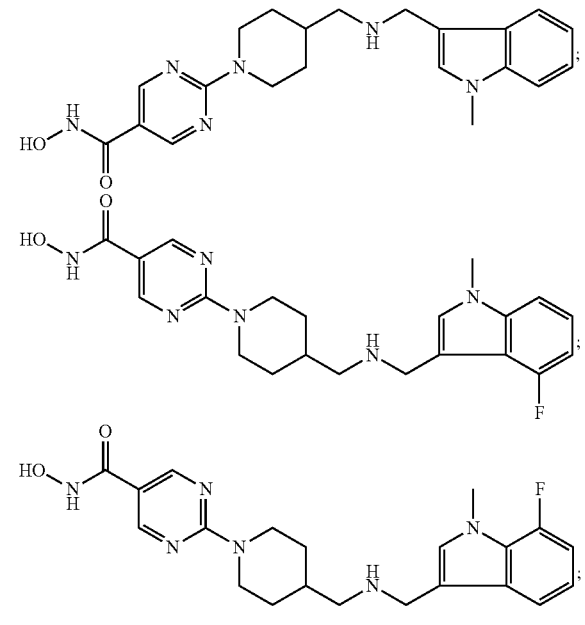

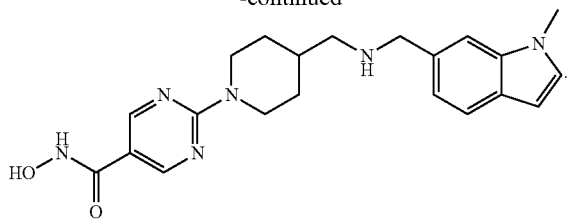

9. The method of claim 8, wherein the compound of formula I is

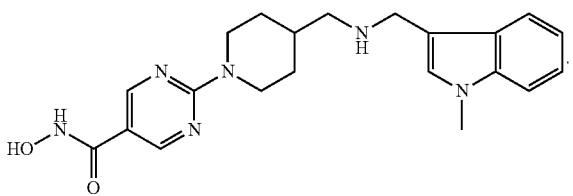 [SMILES: Cn1cc(CNCC2CCN(c3ncc(C(=O)NO)cn3)CC2)c2ccccc21]

10. A method of inhibiting tumor cell growth in a subject having ovarian cancer comprising administering to the subject a therapeutically effective amount of the compound of formula (I),

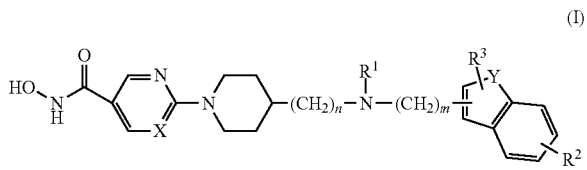

an N-oxide form, pharmaceutically acceptable addition salt or stereo-chemically isomeric form thereof, wherein
each n is an integer with value 0, 1 or 2 and when n is 0 then a direct bond is intended;
each m is an integer with value 1 or 2;
each X is independently N or CH;
each Y is independently O, S, or $NR^4$; wherein
each $R^4$ is hydrogen, $C_{1-6}$alkyl, $C_{1-6}$alkyloxy$C_{1-6}$alkyl, $C_{3-6}$cycloalkyl, $C_{3-6}$cycloalkylmethyl, phenyl$C_{1-6}$alkyl, —C(=O)—CHR$^5$R$^6$ or —S(=O)$_2$—N(CH$_3$)$_2$; wherein
each $R^5$ and $R^6$ is independently hydrogen, amino, $C_{1-6}$alkyl or amino$C_{1-6}$alkyl; and
when Y is $NR^4$ and $R^2$ is on the 7-position of the indolyl, then $R^2$ and $R^4$ together optionally form the bivalent radical —(CH$_2$)$_2$— (a-1), or —(CH$_2$)$_3$— (a-2);

R is hydrogen, $C_{1-6}$alkyl, hydroxy$C_{1-6}$alkyl, $C_{1-6}$alkylsulfonyl, $C_{1-6}$alkylcarbonyl or mono- or di($C_{1-6}$alkyl)aminosulfonyl;
$R^2$ is hydrogen, hydroxy, amino, halo, $C_{1-6}$alkyl, cyano, $C_{2-6}$alkenyl, polyhalo$C_{1-6}$alkyl, nitro, phenyl, $C_{1-6}$alkylcarbonyl, hydroxycarbonyl, $C_{1-6}$alkylcarbonylamino, $C_{1-6}$alkyloxy, or mono- or di($C_{1-6}$alkyl)amino;
$R^3$ is hydrogen, $C_{1-6}$alkyl, or $C_{1-6}$alkyloxy; and
when $R^2$ and $R^3$ are on adjacent carbon atoms, they optionally form the bivalent radical

—O—CH$_2$—O—.

11. The method of claim 10 wherein in the compound of formula I $R^4$ is hydrogen, $C_{1-6}$alkyl, $C_{3-6}$cycloalkyl, $C_{3-6}$cycloalkylmethyl, —C(=O)13 CHR$^5$R$^6$ or —S(=O)$_2$-N(CH$_3$)$_2$;
$R^1$ is hydrogen, $C_{1-6}$alkyl, hydroxy$C_{1-6}$alkyl, $C_{1-6}$alkylsulfonyl, or mono- or di($C_{1-6}$alkyl)aminosulfonyl; and
$R^3$ is hydrogen.

12. The method of claim 10 wherein in the compound of formula I
n is an integer with value 0 or 1;
X is independently N;
$R^4$ is hydrogen or $C_{1-6}$alkyl;
$R^1$ is hydrogen, $C_{1-6}$alkyl or hydroxy$C_{1-6}$alkyl; and
$R^2$ is hydrogen, halo, $C_{1-6}$alkyl or $C_{1-6}$alkyloxy.

13. The method of claim 10 wherein in the compound of formula I
n is an integer with value 0 or 1;
$R^4$ is hydrogen, $C_{1-6}$alkyl, $C_{1-6}$alkyloxy$C_{1-6}$alkyl, $C_{3-6}$cycloalkyl or phenyl$C_{1-6}$alkyl;
$R^1$ is hydrogen, $C_{1-6}$alkyl, hydroxy$C_{1-6}$alkyl, $C_{1-6}$alkylcarbonyl or $C_{1-6}$alkylsulfonyl; and
$R^2$ is hydrogen, halo, $C_{1-6}$alkyl, cyano, nitro or $C_{1-6}$alkyloxy.

14. The method of claim 10 wherein in the compound of formula I
n is an integer with value 1;
m is an integer with value 1;
X is independently N;
Y is independently $NR^4$;
$R^4$ is $C_{1-6}$alkyl;
$R^1$ is hydrogen;
$R^2$ is hydrogen or halo; and
$R^3$ is hydrogen.

15. The method of claim 10 wherein in the compound of formula I
n is an integer with value 0 or 1;
$R^4$ is hydrogen, $C_{1-6}$alkyl, $C_{1-6}$alkyloxy$C_{1-6}$alkyl, $C_{3-6}$cycloalkyl or phenyl$C_{1-6}$alkyl;
$R^1$ is hydrogen, $C_{1-6}$alkyl, hydroxy$C_{1-6}$alkyl, $C_{1-6}$alkylcarbonyl or $C_{1-6}$alkylsulfonyl; and
$R^2$ is hydrogen, halo, $C_{1-6}$alkyl, cyano, nitro, polyhalo $C_{1-6}$alkyl or $C_{1-6}$alkyloxy.

16. The method of claim 10 wherein in the compound of formula I
n is an integer with value 1;
m is an integer with value 1;
X is independently N;
Y is independently $NR^4$;
$R^4$ is $C_{1-6}$alkyl;
$R^1$ is hydrogen;
$R^2$ is hydrogen or halo; and
$R^3$ is hydrogen.

17. The method of claim 16, wherein the compound of formula I is selected from the group consisting of
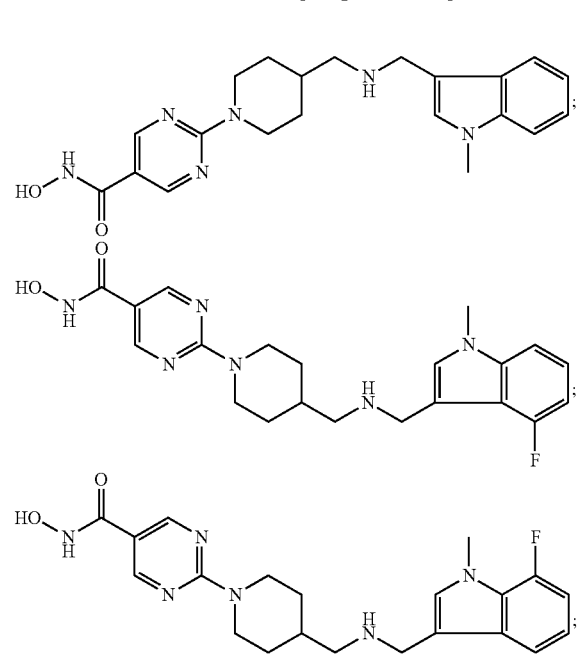
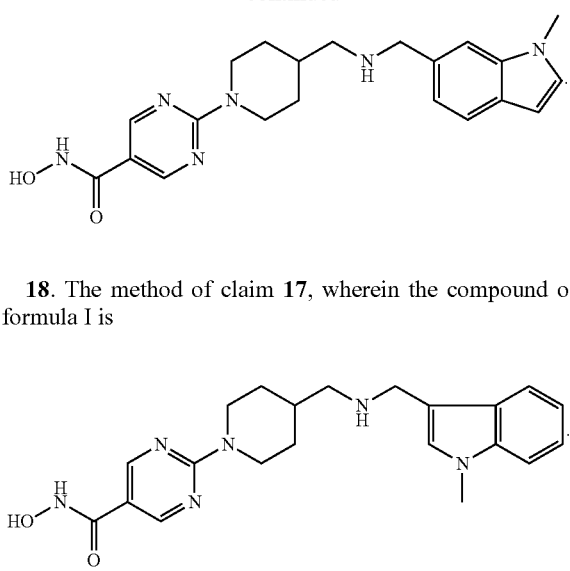
18. The method of claim 17, wherein the compound of formula I is
19. The method of claim 10, wherein the tumor cell growth is caused by histone deacetylase (HDAC) activity.
* * * * *